US007892793B2

(12) United States Patent
Xu

(10) Patent No.: US 7,892,793 B2
(45) Date of Patent: Feb. 22, 2011

(54) ALLELE-SPECIFIC RNA INTERFERENCE

(75) Inventor: Zuoshang Xu, North Grafton, MA (US)

(73) Assignee: University of Massachusetts, Boston, MA (US)

( * ) Notice: Subject to any disclaimer, the term of this patent is extended or adjusted under 35 U.S.C. 154(b) by 801 days.

(21) Appl. No.: 11/241,873

(22) Filed: Sep. 30, 2005

(65) Prior Publication Data

US 2006/0128650 A1 Jun. 15, 2006

(51) Int. Cl.
  *C07H 21/02* (2006.01)
  *C07H 21/04* (2006.01)
  *A61K 31/70* (2006.01)
  *C12Q 1/68* (2006.01)

(52) U.S. Cl. .................... 435/91.1; 435/6; 536/23.1; 536/24.1; 536/24.5; 514/44 A

(58) Field of Classification Search .................. None
See application file for complete search history.

(56) References Cited

U.S. PATENT DOCUMENTS

| | | | |
|---|---|---|---|
| 6,506,559 B1 | 1/2003 | Fire et al. | |
| 7,459,547 B2 * | 12/2008 | Zamore et al. | 536/24.5 |
| 2002/0086356 A1 | 7/2002 | Tuschl et al. | |
| 2003/0108923 A1 | 6/2003 | Tuschl et al. | |
| 2004/0096843 A1 | 5/2004 | Rossi et al. | |
| 2004/0175703 A1 | 9/2004 | Kreutzer et al. | |
| 2004/0180351 A1 | 9/2004 | Giese et al. | |
| 2004/0192629 A1 | 9/2004 | Xu et al. | |
| 2004/0203145 A1 | 10/2004 | Zamore et al. | |
| 2004/0214198 A1 | 10/2004 | Rana | |
| 2004/0229266 A1 | 11/2004 | Tuschl et al. | |
| 2004/0248299 A1 | 12/2004 | Jayasena et al. | |
| 2004/0259247 A1 | 12/2004 | Tuschl et al. | |
| 2004/0259248 A1 | 12/2004 | Tuschl et al. | |
| 2005/0020521 A1 | 1/2005 | Rana | |
| 2005/0026278 A1 | 2/2005 | Tuschl et al. | |
| 2005/0037988 A1 | 2/2005 | Zamore et al. | |
| 2005/0059005 A1 | 3/2005 | Tuschl et al. | |
| 2005/0106731 A1 * | 5/2005 | Davidson et al. | 435/456 |
| 2005/0181382 A1 * | 8/2005 | Zamore et al. | 435/6 |
| 2005/0182005 A1 | 8/2005 | Tuschl et al. | |
| 2005/0186586 A1 | 8/2005 | Zamore et al. | |
| 2005/0227256 A1 | 10/2005 | Hutvagner et al. | |
| 2005/0227940 A1 | 10/2005 | Rossi et al. | |
| 2005/0234007 A1 | 10/2005 | Tuschl et al. | |
| 2005/0244858 A1 | 11/2005 | Rossi et al. | |
| 2005/0246794 A1 | 11/2005 | Khvorova et al. | |
| 2005/0256072 A1 | 11/2005 | Aronin et al. | |
| 2005/0273868 A1 | 12/2005 | Rana | |
| 2005/0277610 A1 | 12/2005 | Rossi et al. | |
| 2006/0009402 A1 | 1/2006 | Zamore et al. | |
| 2006/0069050 A1 | 3/2006 | Rana | |
| 2006/0128650 A1 | 6/2006 | Xu | |
| 2006/0134787 A1 | 6/2006 | Zamore et al. | |
| 2006/0166910 A1 | 7/2006 | Tuschl et al. | |
| 2006/0178334 A1 | 8/2006 | Rossi et al. | |
| 2006/0212950 A1 | 9/2006 | Tuschl et al. | |
| 2007/0003960 A1 | 1/2007 | Tuschl et al. | |
| 2007/0003961 A1 | 1/2007 | Tuschl et al. | |
| 2007/0003962 A1 | 1/2007 | Tuschl et al. | |
| 2007/0003963 A1 | 1/2007 | Tuschl et al. | |
| 2007/0031844 A1 | 2/2007 | Khvorova et al. | |
| 2007/0039072 A1 | 2/2007 | Khvorova et al. | |
| 2007/0093445 A1 | 4/2007 | Tuschl et al. | |
| 2007/0104688 A1 | 5/2007 | Rossi et al. | |
| 2007/0111228 A1 | 5/2007 | Jayasena et al. | |
| 2007/0207974 A1 | 9/2007 | Khvorova et al. | |
| 2007/0265220 A1 | 11/2007 | Rossi et al. | |

FOREIGN PATENT DOCUMENTS

| | | |
|---|---|---|
| CA | 2432341 A1 | 7/2002 |
| CA | 2432350 A1 | 7/2002 |

(Continued)

OTHER PUBLICATIONS

European Office Action for Application No. 06836174.0, dated Dec. 10, 2008.
Bohnsack, M.T. et al., "Exportin 5 is a RanGTP-dependent dsRNA-binding protein that mediates nuclear export of pre-miRNAs," RNA, vol. 10:185-191 (2004).
Bracht, J et al., "Trans-splicing and polyadenylation of let-7 microRNA primary transcripts," RNA, vol. 10:1586-1594 (2004).
Brown, KM et al., "Target accessibility dictates the potency of human RISC," Nature Structural & Molecular Biology, vol. 12(5):469-470 (2005).
Cai, X et al., "Human microRNAs are processed from capped, polyadenylated transcripts that can also function as mRNAs," RNA, vol. 10:1957-1966 (2004).
Chalk, A.M. et al., "siRNAdb: a database of siRNA sequences," Nucleic Acids Research, vol. 33:D131-D134 (2005).

(Continued)

*Primary Examiner*—Sean R McGarry
(74) *Attorney, Agent, or Firm*—Nelson Mullins Riley & Scarborough, LLP; Debra J. Milasincic, Esq.; James H. Velema, Esq.

(57) ABSTRACT

Human diseases caused by dominant, gain-of-function mutations develop in heterozygotes bearing one mutant and one wild-type copy of a gene. Because the wild-type gene often performs important functions, whereas the mutant gene is toxic, any therapeutic strategy must selectively inhibit the mutant while retaining wild-type gene expression. The present invention includes methods of specifically inhibiting the expression of a mutant allele, while preserving the expression of a co-expressed wild-type allele using RNAi, a therapeutic strategy for treating genetic disorders associated with dominant, gain-of-function gene mutations. The invention also includes small interfering RNAs (siRNAs) and small hairpin RNAs (shRNAs) that selectively suppress mutant, but not wild-type, expression of copper zinc superoxide dismutase (SOD1), which causes inherited amyotrophic lateral sclerosis (ALS). The present invention further provides asysmmetric siRNAs and shRNAs with enhanced efficacy and specificity and mediating RNAi.

10 Claims, 15 Drawing Sheets

FOREIGN PATENT DOCUMENTS

| | | |
|---|---|---|
| DE | 10160151 A1 | 6/2003 |
| EP | 1389637 A1 | 2/2004 |
| EP | 1527176 B1 | 5/2005 |
| EP | 1857547 A2 | 11/2007 |
| WO | WO 94/19493 * | 9/1994 |
| WO | WO-02/44321 A2 | 6/2002 |
| WO | WO-02/055692 A2 | 7/2002 |
| WO | WO-02/055693 A2 | 7/2002 |
| WO | WO-03/020931 A2 | 3/2003 |
| WO | WO-03/035869 A1 | 5/2003 |
| WO | WO-03/068797 A1 | 8/2003 |
| WO | WO-2004/015107 A2 | 2/2004 |
| WO | WO-2004/029212 A2 | 4/2004 |
| WO | WO-2004042027 | 5/2004 |
| WO | WO-2004/045543 A2 | 6/2004 |
| WO | WO-2004/046324 A2 | 6/2004 |
| WO | WO-2004/111191 A2 | 12/2004 |
| WO | WO-2005001043 | 1/2005 |
| WO | WO-2005062937 | 7/2005 |
| WO | WO-2005/069987 A2 | 8/2005 |
| WO | WO-2005/079532 A2 | 9/2005 |
| WO | WO-2005/079533 A2 | 9/2005 |
| WO | WO-2005/089287 A2 | 9/2005 |
| WO | WO-2006015389 | 2/2006 |

OTHER PUBLICATIONS

Denli, A.M. et al., "Processing of primary microRNAs by the Microprocessor complex," Nature, vol. 432(11):231-235 (2004).
Ding, H. et al., "Selective silencing by RNAi of a dominant allele that causes amyotrophic lateral sclerosis," Agin Cell, vol. 2:209-217 (2003).
Förstemann, K. et al., "Normal microRNA maturation and germ-line stem cell maintenance requires loquacious, a double-stranded RNA-binding domain protein," PLOS Biology, vol. 3(7):1-15 (2005).
Griffiths-Jones, S., "The MicroRNA registry," Nucleic Acids Research, vol. 32:D109-D111 (2004).
Grishok, A. et al.,"Genes and Mechanisms related to RNA interference regulate expression of the small temporal RNAs that control *C. elegans* developmental timing," Cell, vol. 106:23-34 (2001).
Haley, B. et al.,"Kinetic analysis of the RNAi enzyme complex," Nature Structural & Molecular Biology, vol. 11(7):599-606 (2004).
Heale, B.S. et al.,"siRNA target site secondary structure predictions using local stable substructures," Nucleic Acids Research, vol. 33(3):e30/1-10 (2005).
Hohjoh, H. et al.,"Enhancement of RNAi activity by improved siRNA duplexes," FEBS Letters, vol. 557:193-198 (2004).
Hsieh, A.C. et al.,"A library of siRNA duplexes targeting the phosphoinositide 3-kinase pathway: determinants of gene silencing for use in cell-based screens," Nucleic Acids Research, vol. 32(3):893-901 (2004).
Hutvagner. G. et al.,"A cellular function for the RNA-interference enzyme dicer in the maturation of the let-7 small temporal RNA," Science, vol. 293:834-838 (2001).
Jackson, A.L. et al.,"Expression profiling reveals off-target gene regulation by RNAi," Nature Biotechnology, vol. 21(6):635-638 (2003).
Ketting, R.F. et al.,"Dicer functions in RNA interference and in sythesis of small RNA involved in developmental timing in *C. elegans*," Genes & Development, vol. 15:2654-2659 (2001).
Khvorova, A. et al.,"Functional siRNAs and miRNAs exhibit strand bias," Cell, vol. 115:209-216 (2003).
Kim, V.N. et al.,"MicroRNA Biogenesis: Coordinated cropping and dicing," Nature Reviews, vol. 6:376-385 (2005).
Lee, Y. et al.,"MicroRNA genes are transcribed by RNA polymerase II," The EMBO Journal, vol. 23(20):4051-4060 (2004).
Lee, Y. et al.,"The nuclear RNase III Drosha initiates microRNA processing," Nature, vol. 425:415-419 (2003).
Lund, E. et al.,"Nuclear export of MicroRNA Precursors," Science, vol. 303:95-98 (2004).

Miller, V.M. et al.,"Allele-specific silencing of dominant disease genes," PNAS, vol. 100(12):7195-7200 (2003).
Reynolds, A. et al.,"Rational siRNA design for RNA interference," Nature Biotechnology, vol. 22(3):326-330 (2004).
Schwarz, D.S. et al.,"Asymmetry in the assembly of the RNAi enzyme complex," Cell, vol. 115:199-208 (2003).
Shi, Yang,"Mammalian RNAi for the masses," Trends in Genetics, vol. 19(1):9-12 (2003).
Tomari, Y. et al.,"A protein sensor for siRNA asymmetry," Science, vol. 306:1377-1380 (2004).
Tomari, Y. et al.,"Perspective: machines for RNAi," Genes & Development, vol. 19:517-529 (2005).
Xia, H. et al.,"siRNA-mediated gene silencing in vitro and in vivo," Nature Biotechnology, vol. 20:1006-1010 (2002).
Yi, R. et al.,"Exportin-5 mediates the nuclear export of pre-microRNAs and short hairpin RNAs," Genes & Development, vol. 17:3011-3016 (2003).
Zeng, Y. et al., "Sequence requirements for micro RNA processing and function in human cells," RNA, vol. 9:112-123 (2003).
Zeng, Y. et al.,"Structural requirements for pre-microRNA binding and nuclear export by exportin 5," Nucleic Acids Research, vol. 32(16):4776-4785 (2004).
Zhou, H. et al.,"An RNA polymerase II construct synthesizes short-hairpin RNA with a quantitative indicator and mediates highly efficient RNAi," Nucleic Acids Research, vol. 33(6):e62/1-8 (2005).
Office Action mailed Jun. 4, 2008 for U.S. Appl. No. 10/859,321 (Inventor: Phillip D. Zamore et al.).
Office Action mailed Aug. 22, 2007 for U.S. Appl. No. 10/859,321 (Inventor: Phillip D. Zamore et al.).
Office Action mailed Sep. 14, 2007 for U.S. Appl. No. 10/912,440 (Inventor: Phillip D. Zamore et al.).
Office Action mailed Jul. 2, 2008 for U.S. Appl. No. 10/912,440 (Inventor: Phillip D. Zamore et al.).
Office Action mailed Jan. 25, 2007 for U.S. Appl. No. 10/859,337 (Inventor: Phillip D. Zamore et al.).
Office Action mailed May 30, 2006 for U.S. Appl. No. 10/859,337 (Inventor: Phillip D. Zamore et al.).
Office Action mailed Mar. 27, 2008 for U.S. Appl. No. 11/022,055 (Inventor: Phillip D. Zamore et al.).
Office Action mailed Aug. 17, 2007 for U.S. Appl. No. 11/022,055 (Inventor: Phillip D. Zamore et al.).
International Preliminary Report on Patentability mailed Apr. 2, 2008 for PCT/US2006/03874 (Inventor: Zuoshang Xu).
Akhtar, S et al., "Nonviral delivery of synthetic siRNAs in vivo", The Journal of Clinical Investigation. 117(12):3623-3632 (2007).
Amarzguioui, Mohammed et al., "Rational design and in vitro and in vivo delivery of Dicer substrate siRNA," Nature Protocols, vol. 1(2):508-517 (2006).
Amarzguioui, Mohammed et al., "Tolerance for mutations and chemical modifications in a siRNA," Nucleic Acids Research, vol. 31(2):589-595 (2003).
Ambros, Victor et al., "MicroRNAs and Other Tiny Endogenous RNAs in *C. elegans*," Current Biology, vol. 13:807-818 (2003).
Aravin, Alexei A. et al., "The Small RNA Profile during *Drosophila melanogaster* Development," Development Cell, vol. 5:337-350 (2003).
Bailly, Christian et al., "The use of diaminopurine to investigate structural properties of nucleic acids and molecular recognition between ligands and DNA," Nucleic Acids Research, vol. 26(19):4309-4314 (1998).
Bartel DP. MicroRNAs: genomics, biogenesis, mechanism, and function. Cell. Jan. 23, 2004;116(2):281-97.
Behndig, Anders et al., "In Vitro Photochemical Cataract in Mice Lacking Copper-zinc Superoxide Dismutase," Free Radical Biology & Medicine, vol. 31(6):738-744 (2001).
Bernstein, Emily et al., "Role for a bidentate ribonuclease in the initiation step of RNA interference," Nature, 409:363-366 (2001).
Boden D, Pusch O, Lee F, Tucker L, Ramratnam B. Efficient gene transfer of HIV-1-specific short hairpin RNA into human lymphocytic cells using recombinant adeno-associated virus vectors. Mol Ther. Mar. 2004;9(3):396-402.

Boden D, Pusch O, Silbermann R, Lee F, Tucker L, Ramratnam B. Enhanced gene silencing of HIV-1 specific siRNA using microRNA designed hairpins. Nucleic Acids Res. Feb. 13, 2004;32(3):1154-8.

Bonnet E, Wuyts J, Rouze P, Van De Peer Y. Evidence that microRNA precursors, unlike other non-coding RNAs, have lower folding free energies than random sequences. Bioinformatics. Jun. 24, 2004.

Boutla, Alexandra et al., "Development defects by antisense-mediated inactivation of micro-RNAs 2 and 13 in *Drosophila* and the identification of putative target genes," *Nucleic Acids Research*, vol. 31(17):4973-4980 (2003).

Boutla, Alexandra et al., "Short 5'-phosphorylated double-stranded RNAs induce RNA interference in *Drosophila*," *Current Biology*, vol. 11:1776-1780 (2001).

Brennecke, Julius et al., "*bantam* Encodes a Developmentally Regulated microRNA that Controls Cell Proliferation and Regulates the Proapoptotic Gene *hid* in *Drosophila*," *Cell*, vol. 113:25-36 (2003).

Brennecke, Julius et al., "Towards a complete description of the microRNA complement of animal genomes," *Genome Biology*, vol. 4:228-228.3 (2003).

Brummelkamp, Thijn R. et al., "A System for Stable Expression of Short Interfering RNAs in Mammalian Cells," www.scienceexpress.org, (2002).

Brummelkamp, Thijn R. et al., "Stable suppression of tumorigenicity by virus-mediated RNA interference," *Cancer Cell*, vol. 2:243-247 (2002).

Bumcrot, David et al., "RNAi therapeutics: a potential new class of pharmaceutical drugs", Nature Chemical Biology. 2(12): 711-719 (2006).

Caccone, Adalgisa et al., "Calibration of the Change in Thermal Stability of DNA Duplexes and Degree of Base Air Pair Mismatch," *Journal of Molecular Evolution*, vol. 27:212-216 (1988).

Caplen, Natasha J. et al., "dsRNA-mediated gene silencing in the cultured *Drosophila* cells: a tissue culture model for the analysis of RNA interference," *Gene*, vol. 252:95-105 (2000).

Caplen, Natasha J. et al., "Rescue of polyglutamine-mediated cytotoxicity by double-stranded RNA-mediated RNA interference," *Human Molecular Genetics*, vol. 11(2):175-184 (2002).

Caplen, Natasha J. et al., "Specific inhibition of gene expression by small double-stranded RNAs in invertebrate and vertebrate systems," *PNAS*, vol. 98(17):9742-9747 (2001).

Carthew, Richard W., "Gene silencing by double-stranded RNA," *Current Opinion in Cell Biology*, vol. 13:244-248 (2001).

Catalanotto, Caterina et al., "Gene silencing in worms and fungi," *Nature*, vol. 404:245 (2000).

Catalanotto, Caterina et al., "Involvement of small RNAs and role of the *qde* genes in the gene silencing pathway in *Neurospora*," *Genes & Development*, vol. 16:790-795 (2002).

Caudy, Amy A. et al., "Fragile X-related protein and VIG associate with the RNA interference machinery," *Genes & Development*, vol. 16:2491-2496 (2002).

Chi JT, Chang HY, Wang NN, Chang DS, Dunphy N, Brown PO. Genomewide view of gene silencing by small interfering RNAs. Proc Natl Acad Sci U S A. May 27, 2003;100(11):6343-6.

Chiu, Ya-Lin et al., "RNAi in Human Cells: Basic Structural and Functional Features of Small Interfering RNA," *Molecular Cell*, vol. 10:549-561 (2002).

Chiu, Ya-Lin et al., "siRNA function in RNAi: A chemical modification analysis," *RNA*, vol. 9:1034-1048 (2003).

Cleveland, Don W. et al., "From Charcot to Lou Gehrig: Deciphering Selective Motor Neuron Death in ALS," *Nature Reviews Neuro.*, vol. 2:806-819 (2001).

Cogoni, Carlo et al., "Gene silencing in *Neurospora crassa* requires a protein homologous to RNA-dependent RNA polymerase," *Nature*, vol. 399:166-168 (1999).

Cogoni, Carlo et al., "Isolation of quelling-defective (*qde*) mutants impaired in posttranscriptional transgene-induced gene silencing in *Neurospora crassa*," *Proc. Natl. Acad. Sci. USA*, vol. 94:10233-10238 (1997).

Cogoni, Carlo et al., "Posttranscriptional Gene Silencing in *Neurospora* by a RecQ DNA Helicase," *Science*, vol. 286:2342-2344 (1999).

Conte, Darryl Jr. et al., "RNA Interference in *Caenorhabditis elegans*," *Current Protocols in Molecular Biology*, F.M. Asubel et al., eds., John Wiley & Sons, pp. 26.3.1-26.3.20 (2003).

Corey, David R. et al., "Chemical modification: the key to clinical application of RNA interference?" The Journal of Clinical Investigation. 117(12): 3615-3622 (2007).

Czauderna, Frank et al., "Structural variations and stabilising modifications of synthetic siRNAs in mammalian cells," *Nucleic Acids Research*, vol. 31(11):2705-2716 (2003).

Dalmay, Tamas et al., "An RNA-Dependent RNA Polymerase Gene in *Arabidopsis* Is Required for Posttranscriptional Gene Silencing Mediated by a Transgene but Not by a Virus," *Cell*, vol. 101:543-553 (2000).

Dalmay, Tamas et al., "*SDE3* encodes an RNA helicase required for posttranscriptional gene silencing in *Arabidopsis*," *The EMBO Journal*, vol. 20(8):2069-2077 (2001).

Denli, Ahmet M. et al., "Processing of primary microRNAs by the Microprocessor complex," *Nature*, vol. 432:231-235 (2004).

Devroe, Eric et al., "Retrovirus-delivered siRNA," *BMC Biotechnology*, vol. 2(15) (2002).

Dharmacon RNA Technologies. On-Target siRNA. Company Brochure.

Dharmacon RNA Technologies. Products for RNA Interference. Company brochure.

Doench JG, Petersen CP, Sharp PA. siRNAs can function as miRNAs. Genes Dev. Feb. 15, 2003;17(4):438-42.

Doench, John G. et al., "Specificity of microRNA target selection in translational repression," *Genes & Development*, 2004:504-511 (2004).

Dostie, Josée et al., "Numerous microRNPs in neuronal cells containing novel microRNAs," *RNA*, vol. 9:180-186 (2003).

Elbashir, Sayda M. et al., "Duplexes of 21-nucleotide RNAs mediated RNA interference in cultured mammalian cells," *Nature*, vol. 411:494-498 (2001).

Elbashir, Sayda M. et al., "Functional anatomy of siRNAs for mediating efficient RNAi in *Drosophila melanogaster* embryo lysate," *The EMBO Journal*, vol. 20(23):6877-6888 (2001).

Elbashir, Sayda M. et al., "RNA interference is mediated by 21- and 22-nucleotide RNAs," *Genes & Development*, vol. 15:188-200 (2001).

Enright, Anton J. et al., "MicroRNA targets in *Drosophila*," *Genome Biology*, vol. 5:R1 (2003).

Fagard, Mathilde et al., "AG01, QDE-2, and RDE-1 are related proteins required for post-transcriptional gene silencing in plants, quelling ni fungi, and RNA interference in animals," *PNAS*, vol. 97(21):11650-11654 (2000).

Fire, Andrew et al., "Potent and specific genetic interference by double-stranded RNA in *Caenorhabditis elegans*," *Nature*, vol. 391:806-811 (1998).

Flood, Dorothy G. et al., "Hindlimb Motor Neurons Require Cu/Zn Superoxide Dismutase for Maintenance of Neuromuscular Junctions," *American Journal of Pathology*, vol. 155(2):663-672 (1999).

Förstemann, Klaus et al., "Normal microRNA Maturation and Germ-Line Stem Cell Maintenance Requires Loquacious, a Double-Stranded RNA-Binding Domain Protein," *PLoS Biology*, vol. 3(7):e236 (2005).

Gerwitz, Alan M. "On future's doorstep: RNA interference and the pharmacopeia of tomorrow", The Journal of Clinical Investigation. 117(12): 3612-3614 (2007).

Grimm D and Kay MA. "Therapeutic application of RNAi: is mRNA targeting finally ready for prime time?" *The Journal of Clinical Investigation*. 117(12): 3633-3641 (2007).

Grishok, Alla et al., "Genetic Requirements for Inheritance of RNAi in *C. elegans*," *Science*, vol. 287:2494-2497 (2000).

Grishok, Alla et al., "RNAi (Nematodes *Caenorhabditis elegans*)," *Advances in Genetics*, vol. 46:339-360 (2002).

Grzelinski, Marius et al, "RNA Interference-Mediated Gene Silencing of Pleiotrophin Through Polyethylenimine-Complexed Small Interfering RNAs In Vivo Exerts Antitumoral Effects in Glioblastoma Xenografts," *Human Gene Therapy*, 17:751-766 (2006).

Ha, Ilho et al., "A bulged *lin-4/lin-14* RNA duplex is sufficient for *Caenorhabditis elegans lin-14* temporal gradient formation," *Genes & Development*, vol. 10:3041-3050 (1996).

Haley, Benjamin et al., "In vitro analysis of RNA interference in *Drosophila melanogaster,*" *Methods*, vol. 30:330-336 (2003).

Hamilton, Andrew J. et al., "A Species of Small Antisense RNA in Posttranscriptional Gene Silencing in Plants," *Science*, vol. 286:950-952 (1999).

Hammond, Scott M. et al., "An RNA-directed nuclease mediates post-transcriptional gene silencing in *Drosophila* cells," *Nature*, vol. 404:293-296 (2000).

Hammond, Scott M. et al., "Argonaute2, a Link Between Genetic and Biochemical Analyses of RNAi," *Science*, vol. 293:1146-1150 (2001).

Hammond, Scott M. et al., "Post-Transcriptional Gene Silencing by Double-Stranded RNA," *Nature*, vol. 2:110-119 (2001).

Hannon, Gregory J., "RNA interference," *Nature*, vol. 418:244-251 (2002).

Hannon, Gregory J. et al., "Unlocking the potential of the human genome with RNA interference," *Nature*, vol. 431:371-378 (2004).

Heale, Bret S.E. et al., "siRNA target site secondary structure predictions using local stable substructures," *Nucleic Acids Research*, vol. 33(3):1-10 (2005).

Holen T, Amarzguioui M, Babaie E, Prydz H. Similar behaviour of single-strand and double-strand siRNAs suggests they act through a common RNAi pathway. Nucleic Acids Res. May 1, 2003;31(9):2401-7.

Hu-Lieskovan, Siwen et al, "Sequence-Specific Knockdown of EWS-FLI1 by Targeted, Nonrival Delivery of Small Interfering RNA Inhibits Tumor Growth in a Murine Model of Metastatic Ewing's Sarcoma," *Cancer Research*, 65:(19) 8984-8992 (2005).

Hutvágner, György et al., "A microRNA in a Multiple-Turnover RNAi Enzyme Complex," *Science*, vol. 297:2056-2060 (2002).

Hutvágner, György et al., "RNAi: nature abhors a double-strand," *Current Opinion in Genetics & Development*, vol. 12:225-232 (2002).

Jacque, Jean-Marc et al., "Modulation of HIV-1 replication by RNA interference," *Nature*, vol. 418:435-438 (2002).

KAwase, Makoto et al., "Exacerbation of Delayed Cell Injury After Transient Global Ischemia in Mutant Mice With CuZn Superoxide Dismutase Deficiency," *Stroke*, vol. 30:1962-1968 (1999).

Ketting, René F. et a., "A genetic link between co-suppression and RNA interference ni *C. elegans,*" *Nature*, vol. 404:296-298 (2000).

Ketting, René F. et a., "*mut-7* of *C. elegans*, Required for Transposon Silencing and RNA Interference, Is a Homolog of Werner Syndrome Helicase and RNaseD," *Cell*, vol. 99:133-141 (1999).

Kim, Daniel H. et al., "Strategies for silencing human disease using RNA interference," *Nature Reviews Genetics*, vol. 8:173-184 (2007).

Kim, Dong-Ho et al., "Synthetic dsRNA Dicer substrates enhances RNAi potency and efficacy," *Nature Biotechnology*, vol. 23(2):222-226 (2005).

Knight, Scott W. et al., "A Role for the RNase III Enzyme DCR-1 in RNA Interference and Germ Line Development in *Caenorhabditis elegans,*" *Science*, vol. 293:2269-2271 (2001).

Kondo, Takeo et al., "Reduction of CuZn-Superoxide Dismutase Activity Exacerbates Neuronal Cell Injury and Edema Formation after Transient Focal Cerebral Ischemia," *The Journal of Neuroscience*, vol. 17(11):4180-4189 (1997).

Krol J, Sobczak K, Wilczynska U, Drath M, Jasinska A, Kaczynska D, Krzyzosiak WJ. Structural Features of MicroRNA (miRNA) Precursors and Their Relevance to miRNA Biogenesis and Small Interfering RNA/Short Hairpin RNA Design. J Biol Chem. Oct. 1, 2004;279(40):42230-9. Epub Aug. 2, 2004.

Lagos-Quintana, Mariana et al., "Identification of Tissue-Specific MicroRNAs from Mouse," *Current Biology*, vol. 12:735-739 (2002).

Lagos-Quintana, Mariana et al., "Identification of Novel Genes Coding for Small Expressed RNAs," *Science*, vol. 294:853-858 (2001).

Lagos-Quintana, Mariana et al., "New microRNAs from mouse and human," *RNA*, vol. 9:175-179 (2003).

Lai EC. Micro RNAs are complementary to 3' UTR sequence motifs that mediate negative post-transcriptional regulation. Nat Genet. Apr. 2002;30(4):363-4.

Lau, Nelson C. et al., "An Abundant Class of Tiny RNAs with Probable Regulatory Roles in *Caenorhabditis elegans,*" *Science*, vol. 294:858-862 (2001).

Lee, Rosalind C. et al., "An Extensive Class of Small RNAs in *Caenorhabditis elegans,*" *Science*, vol. 294:862-864 (2001).

Lee, Nan Sook et al., "Expression of small interfering RNAs targeted against HIV-1 *rev* transcripts in human cells," *Nature Biotechnology*, vol. 19:500-505 (2002).

Lee, Rosalind C. et al., "The *C. elegans* Heterochronic Gene *lin-4* Encodes Small RNAs with Antisense Complementarity to *lin-14,*" *Cell*, vol. 75:843-854 (1993).

Lewis, Benjamin P. et al., "Prediction of Mammalian MicroRNA Targets," *Cell*, vol. 115:787-798 (2003).

Li, Bao-jian et al, "Using siRNA in Pophylactic and Therapeutic Regimens Against SARS Coronavirus in Rhesus Macaque," *Nature Medicine*, vol. 11:9, 944-951 (2005).

Liang, Xue-hai et al., "Small nuclear RNA interference induced by antisense or double-stranded RNA in trypanosomatids," *PNAS*, vol. 100(13):7521-7526 (2003).

Lieberman, Judy et al., "Interfering with disease: opportunities and roadblocks to harnessing RNA interference," *Trends in Molecular Medicine*, vol. 9(9):397-403 (2003).

Lim, Lee P. et al., "The microRNAs of *Caenorhabditis elegans,*" *Genes & Development*, vol. 17:991-1008 (2003).

Lim, Lee P. et al., "Vertebrate MicroRNA Genes," *Science*, vol. 299:1540 (2003).

Lipardi, Concetta et al., "RNAi as Random Degradative PCR: siRNA Primers Convert mRNA into dsRNAs that Are Degraded to Generate New siRNAs," *Cell*, vol. 107:297-307 (2001).

Liu, Qinghua et al., "R2D2, a Bridge Between the Initiation and Effector Steps of the *Drosophila* RNAi Pathway," *Science*, vol. 301:1921-1925 (2003).

Mallory AC, Reinhart BJ, Jones-Rhoades MW, Tang G, Zamore PD, Barton MK, Bartel DP. MicroRNA control of PHABULOSA in leaf development: importance of pairing to the microRNA 5' region. EMBO J. Aug. 18, 2004;23(16):3356-64. Epub Jul. 29, 2004.

Martinez J, Patkaniowska A, Urlaub H, Luhrmann R, Tuschl T. Single-stranded antisense siRNAs guide target RNA cleavage in RNAi. Cell. Sep. 6, 2002;110(5):563-74.

Matz, Paul G. et al., "Cell Death After Exposure to Subarachnoid Hemolysate Correlates Inversely With Expression of CuZn-Superoxide Dismutase," *Stroke*, vol. 31:2450-2458 (2000).

Matzuk, Martin M. et al., "Ovarian Function in Superoxide Dismutase 1 and 2 Knockout Mice," *Endocrinology*, vol. 139(9):4008-4011 (1998).

McCaffrey, Anton P. et al., "RNA interference in adult mice," *Nature*, vol. 418:38-39 (2002).

McFadden, Sandra L. et al., "Anatomical, Metabolic and Genetic Aspects of Age-related Hearing Loss in Mice," *Audiology*, vol. 40:313-321 (2001).

McManus, Michael T. et al., "Gene Silencing in Mammals by Small Interfering RNAs," *Nature Reviews Genetics*, vol. 3:737-747 (2002).

McManus MT, Petersen CP, Haines BB, Chen J, Sharp PA. Gene silencing using micro-RNA designed hairpins. RNA. Jun. 2002;8(6):842-50.

Meister G, Landthaler M, Dorsett Y, Tuschl T. Sequence-specific inhibition of microRNA- and siRNA-induced RNA silencing. RNA. Mar. 2004;10(3):544-50.

Merriam-Webster online, "engineer," retrieved online at http://www.merriam-webster.com/dictonary (2008).

Merriam-Webster online, "pharmaceutical," retrieved online at http://www.merriam-webster.com/dictonary (2009).

Miyagishi, Makoto et al., "U6 promoter—driven siRNAs with four uridine 3' overhangs efficiently suppress targeted gene expression in mammalian cells," *Nature Biotechnology*, vol. 19:497-500 (2002).

Molecular Biology of the Cell, Fourth Edition, "DNA Replication Mechanisms," retrieved online at http://www.ncbi.nlm.nih.gov/books/bv.fcgi?highlight=DNA&rid=mboc4.section.754 (2008).

Molecular Biology of the Cell, Fourth Edition, "Figure 4-4," retrieved online at http://www.ncbi.nlm.nih.gov/books/bv.fcgi?rid=mboc4.figgrp (2008).

Molecular Biology of the Cell, Fourth Edition, "The Chemical Composition of a Cell," retrieved online at http://www.ncbi.nlm.nih.gov/books/bv.fcgi?highlight=hydrogen,dna,bond&rid=mboc4.section165 (2008).

Molecular Biology of the Cell, Fourth Edition, "Wobble base-pairing between codons and anticodons," retrieved online at http://www.ncbi.nlm.nih.gov/books/bv.fcgi?highlight=inosine&rid=mboc4.figgrp.1058 (2008).

Moss, Eric G. et al., "The Cold Shock Domain Protein LIN-28 Controls Developmental Timing in *C. elegans* and Is Regulated by the *lin-4* RNA," *Cell*, vol. 88:637-646 (1997).

Mourelatos, Zissimos et al., "miRNPs: a novel class of ribonucleoproteins containing numerous microRNAs," *Genes & Development*, vol. 16:720-728 (2002).

Mourrain, Philippe et al., "*Arabidopsis SGS2* and *SGS3* Genes Are Required for Posttranscriptional Gene Silencing and Natural Virus Resistance," *Cell*, vol. 101:533-542 (2000).

Murchison EP, Hannon GJ. miRNAs on the move: miRNA biogenesis and the RNAi machinery. Curr Opin Cell Biol. Jun. 2004;16(3):223-9.

Nykanen A, Haley B, Zamore PD. ATP requirements and small interfering RNA structure in the RNA interference pathway. Cell. Nov. 2, 2001;107(3):309-21.

Olsen, Philip H. et al., "The *lin-4* Regulatory RNA Controls Developmental Timing in *Caenorhabditis elegans* by Blocking LIN-14 Protein Synthesis after the Initiation of Translation," *Developmental Biology*, vol. 216:671-680 (1999).

Opalinska, Joanna B. et al., "Nucleic Acid Therapeutic for Hematologic Malignancies—Theoretical Considerations," *Ann. N.Y. Acad. Sci.*, vol. 1082:124-136 (2006).

Opalinska, Joanna B. et al., "Nucleic-Acid Therapeutics: Basic Principles and Recent Applications," *Nature Reviews, Drug Discovery*, vol. 1:503-514 (2002).

Paddison, Patrick J. et al., "Short hairpin RNAs (shRNAs) induce sequence-specific silencing in mammalian cells," *Genes & Development*, vol. 16:948-958 (2002).

Parrish, Susan et al., "Functional Anatomy of a dsRNA Trigger: Differential Requirement for the Two Trigger Strands in RNA Interference," *Molecular Cell*, vol. 6:1077-1087 (2000).

Paul, Cynthia P. et al., "Effective expression of small interfering RNA in human cells," *Nature Biotechnology*, vol. 29:505-508 (2002).

Persengiev, Stephan P. et al., "Nonspecific, concentration-dependent stimulation and repression of mammalian gene expression by small interfering RNAs (siRNAs)," *RNA*, vol. 10:12-18 (2004).

Poy, Matthew N. et al., "A pancreatic islet-specific microRNA regulates insulin secretion," *Nature*, vol. 432:226-230 (2004).

Pusch O, Boden D, Silbermann R, Lee F, Tucker L, Ramratnam B. Nucleotide sequence homology requirements of HIV-1-specific short hairpin RNA. Nucleic Acids Res. Nov. 15, 2003;31(22):6444-9.

Reich, Samuel J. et al, "Small Interfering RNA (siRNA) targeting VEGF Effectively Inhibits Ocular Neovascularization in a Mouse Model," *Molecular Vision*, vol. 9, 210-216 (2003).

Reinhart, Brenda J. et al., "MicroRNAs in plants," *Genes & Development*, vol. 16:1616-1626 (2002).

Reinhart, Brenda J. et al., "The 21-nucleotide let-7 RNA regulates developmental timing in *Caenorhabditis elegans*," *Nature*, vol. 403:901-906 (2000).

Rose, Scott D. et al., "Functional polarity is introduced by Dicer processing of short substrate RNAs," *Nucleic Acids Research*, vol. 33(13):4140-4156 (2005).

Saxena, Sandeep et al., "Small RNAs with Imperfect Match to Endogenous mRNA Repress Translation," *The Journal of Biological Chemistry*, vol. 278(45):44312-44319 (2003).

Scadden, A.D.J. et al., "RANi is antagonized by A→I hyper-editing," *EMBO reports*, vol. 2(12):1109-1111 (2001).

Scherer, Lisa J. et al., "Approaches for the sequence-specific knockdown of mRNA," *Nature Biotechnology*, vol. 21(12):1457-1465 (2003).

Scherer, Lisa J. et al., "Rapid Assessment of Anti-HIV siRNA Efficacy Using PCR-Derived Pol III shRNA Cassettes," *Molecular Therapy*, vol. 10(3):597-603 (2004).

Scherer, Lisa J. et al., "Recent Applications of RNAi in Mammalian Systems," *Current Pharmaceutical Biotechnology*, vol. 5:355-360 (2004).

Scherer, Lisa et al., "Therapeutic Applications of RNA Interference: Recent Advances in siRNA Design," *Advances in Genetics*, vol. 52:1-21 (2004).

Schmidt, Charlie, "Negotiating the RNAi patent thicket," *Nature Biotechnology*, vol. 25(3):273-275 (2007).

Schwarz, Dianne S. et al., "Evidence that siRNAs Function as Guides, Not Primers, in the *Drosophila* and Human RNAi Pathways," *Molecular Cell*, vol. 10:537-548 (2002).

Schwarz DS, Tomari Y, Zamore PD. The RNA-induced silencing complex is a Mg2+-dependent endonuclease. Curr Biol. May 4, 2004;14(9):787-91.

Schwarz DS, Zamore PD. Why do miRNAs live in the miRNP? Genes Dev. May 1, 2002;16(9):1025-31.

Seggerson, Kathy et al., "Two Genetic Circuits Repress the *Caenorhabditis elegans* Heterochronic Gene *lin-28* after Translation Initiation," *Developmental Biology*, vol. 243:215-225 (2002).

Semizarov D, Frost L, Sarthy A, Kroeger P, Halbert DN, Fesik SW. Specificity of short interfering RNA determined through gene expression signatures. Proc Natl Acad Sci U S A. May 27, 2003;100(11):6347-52.

Shefner, J.M. et al., "Mice lacking cytosolic copper/zinc superoxide dismutase display a distinctive motor axonopathy," *Neurology*, vol. 53:1239-1246 (1999).

Slack, Frank J. et al., "The *lin-41* RBCC Gene Acts in the *C. elegans* Heterochronic Pathway between the *let-7* Regulatory RNA and the LIN-29 Transcription Factor," *Molecular Cell*, vol. 5:659-669 (2000).

Sledz, Carol A. et al., "Activation of the interferon system by short-interfering RNAs," *Nature Cell Biology*, vol. 5(9):834-838 (2003).

Snøve, Ola Jr. et al., "Chemical Modifications Rescue Off-Target Effects of RNAi," *ACS Chemical Biology*, vol. 1(5):274-276 (2006).

Song, E. et al., "Intrahepatic Gene Silencing by RNA Interference," *Gastroenterology*, vol. 126(1):356-358 (2004).

Song, Erwei et al., "RNA interference targeting Fas protects mice from fulminant hepatitis," *Nature Medicine*, vol. 9(3):347-351 (2003).

Soutschek, Jurgen et al, "Therapeutic Silencing of an Endogenous Gene by Systemic Administration of Modified si RNAs," *Nature Publishing Group*, vol. 432, 173-178 (2004).

Stark, Alexander et al., "Identification of *Drosophila* MicroRNA Targets," *PLOS Biology*, vol. 1(3):397-409 (2003).

Sui, Guangchao et al., "A DNA vector-based RNAi technology to suppress gene expression in mammalian cells," *PNAS*, vol. 99(8):5515-5520 (2002).

Sundaralingam, Muttaiya et al., "Hydrogen and hydration of DNA and RNA oligonucleotides," *Biophysical Chemistry*, vol. 95:273-282 (2002).

Tabara, Hiroaki et al., "The dsRNA Binding Protein RDE-4 Interacts with RDE-1, DCR-1, and a DExH-Box Helicase to Direct RNAi in *C. elegans*," *Cell*, vol. 109:861-871 (2002).

Tabara, Hiroaki et al., "The *rde-1* Gene, RNA Interference and Transposon Silencing in *C. elegans*," *Cell*, vol. 99:123-132 (1999).

Tan, P. H. et al, "Gene Knockdown with Intrathecal siRNA of NMDA Receptor NR2B Subunit Reduces Formalin-induced Nociception in the Rat," *Gene Therapy*, vol. 12, 59-66 (2005).

Tang, Guiliang et al., "A biochemical framework for RNA silencing in plants," *Genes & Development*, vol. 17:49-63 (2003).

Tang G, Zamore PD. Biochemical dissection of RNA silencing in plants. Methods Mol Biol. 2004;257:223-44.

Taylor, J. Paul et al., "Toxic Proteins in Neurodegenerative Disease," *Science*, vol. 296:1991-1995 (2002).

Thakker, Deepak R. et al, "Neurochemical and Behavioral Consequences of Widespred Gene Knockdown in the Adult Mouse Brain by Using Nonrival Interference," *PNAS*, vol. 101:49, 17270-17275 (2004).

Tijsterman, Marcel et al., "PPW-1, a PAZ/PIWI Protein Required for Efficient Germline RNAi, Is Defective in a Natural Isolate of *C. elegans*," *Current Biology*, vol. 12:1535-1540 (2002).

Tijsterman, Marcel et al., "RNA Helicase MUT-14-Dependent Gene Silencing Triggered in *C. elegans* by Short Antisense RNAs," *Science*, Vo. 295:694-697 (2002).

Tomari Y, Du T, Haley B, Schwarz DS, Bennett R, Cook HA, Koppetsch BS, Theurkauf WE, Zamore PD. RISC assembly defects in the *Drosophila* RNAi mutant armitage. Cell. Mar. 19, 2004;116(6):831-41.

Tuschl, Thomas et al., "siRNAs and miRNAs," *Keystone Symposia, Abstract Book* (2004).

Tuschl, Thomas et al., "Targeted mRNA degradation by double-stranded RNA in vitro," *Genes & Development*, vol. 13:3191-3197 (1999).

Vargason JM, Szittya G, Burgyan J, Tanaka Hall TM. Size selective recognition of siRNA by an RNA silencing suppressor. Cell. Dec. 26, 2003;115(7):799-811.

Vella, Monica C. et al., "The *C. elegans* microRNA *let-7* binds to imperfect *let-7* complementary sites from the *lin-41* 3'UTR," *Genes & Development*, vol. 18:132-137 (2004).

Wang, J. et al., "Fas siRNA Reduces Apoptotic Cell Death of Allogeneic-Transplanted Hepatocytes in Mouse Spleen," *Transplantation Proceedings*, Vo. 35:1594-1595 (2003).

Wightman, Bruce et al., "Posttranscriptional Regulation of the Heterochronic Gene *lin-14* by *lin-4* Mediates Temporal Pattern Formation in *C. elegans*," *Cell*, vol. 75:855-862 (1993).

Wu-Sharf, Dancia et al., "Transgene and Transposon Silencing in *Chlamydomonas reinhardtii* by a DEAH-Box RNA Helicase," *Science*, vol. 290:1159-1162 (2000).

Xu, Peizhang et al., "The *Drosophila* MicroRNA Mir-14 Suppresses Cell Death and Is Required for Normal Fat Metabolism," *Current Biology*, vol. 13:790-795 (2003).

Yu, Jenn-Yah et al., "RNA interference by expression of short-interfering RNAs and hairpin RNAs in mammalian cells," *PNAS*, vol. 99(9):6047-6052 (2002).

Zamore, Phillip D. et al., "RNAi: Double-Stranded RNA Directs the ATP-Dependent Cleavage of mRNA at 21 to 23 Nucleotide Intervals," *Cell*, vol. 101:25-33 (2000).

Zamore, Phillip D. et al., "siRNAs knock down hepatitis," *Nature Medicine*, vol. 9(3):266-267 (2003).

Zeng, Yan et al., "Both Natural and Designed Micro RNAs Can Inhibit the Expression of Cognate mRNAs When Expressed in Human Cells," *Molecular Cell*, vol. 9:1327-1333 (2002).

Zeng, Yan et al., "MicroRNAs and small interfering RNAs can inhibit mRNA expression by similar mechanisms," *PNAS*, vol. 100(17):9779-9784 (2003).

Zhang, Yingjie et al, "Engineering Mucosal RNA Interference in Vivo," *Molecular Therapy*, vol. 14:3, 336-342 (2006).

Zhang, Haidi et al., "Human Dicer preferentially cleaves dsRNAs at their termini without a requirement for ATP," *The EMBO Journal*, vol. 21(21):5875-5885 (2002).

Zimmermann, Tracy S. et al, "RNAi-mediated Gene Silencing in Non-human Primates," *Nature*, vol. 441, 111-114 (2006).

European Search Report for Application No. 04753972.1—2402, dated Oct. 31, 2006.

International Search Report for Application No. PCT/US2005/029011, dated Apr. 13, 2006.

Invitation to Pay Additional Fees for Application No. PCT/US2005/029011, dated Feb. 20, 2006.

Written Opinion for Application No. PCT/US2005/029011, dated Apr. 13, 2006.

* cited by examiner

```
mutant siRNA p9        5'-UGGAGACUUGCGCAAUGUGdTdT-3' Sense,(Seq ID No.:1)
                       3'-dTdTACCUCUGAACGCGUUACAC-5' Antisense,(Seq ID No.:2)

p10           5'-GGAGACUUGCGCAAUGUGAdTdT-3' Sense,(Seq ID No.:3)
                       3'-dTdTCCUCUGAACGCGUUACACU-5' Antisense,(Seq ID No.:4)

p11           5'-GAGACUUGCGCAAUGUGACdTdT-3' Sense,(Seq ID No.:5)
                       3'-dTdTCUCUGAACGCGUUACACUG-5' Antisense,(Seq ID No.:6)

sod1 wild type  5'-...GAGAGGCAUGUUGGAGACUUGGGCAAUGUGACUGCUGACAAAGAUGGU...-3'(Seq ID No.:7)
sod1 mutant     5'-...GAGAGGCAUGUUGGAGACUUGCGCAAUGUGACUGCUGACAAAGAUGGU...-3'(Seq ID No.:8)

wild-type siRNA p11    5'-GAGACUUGGGCAAUGUGACdTdT-3' Sense,(Seq ID No.: 9)
                       3'-dTdTCUCUGAACCCGUUACACUG-5' Antisense,(Seq ID No.:10)

p10           5'-GGAGACUUGGGCAAUGUGAdTdT-3' Sense,(Seq ID No.:11)
                       3'-dTdTCCUCUGAACCCGUUACACU-5' Antisense,(Seq ID No.:12)

p9            5'-UGGAGACUUGGGCAAUGUGdTdT-3' Sense,(Seq ID No.:13)
                       3'-dTdTACCUCUGAACCCGUUACAC-5' Antisense,(Seq ID No.:14)
```

*Fig. 1A*

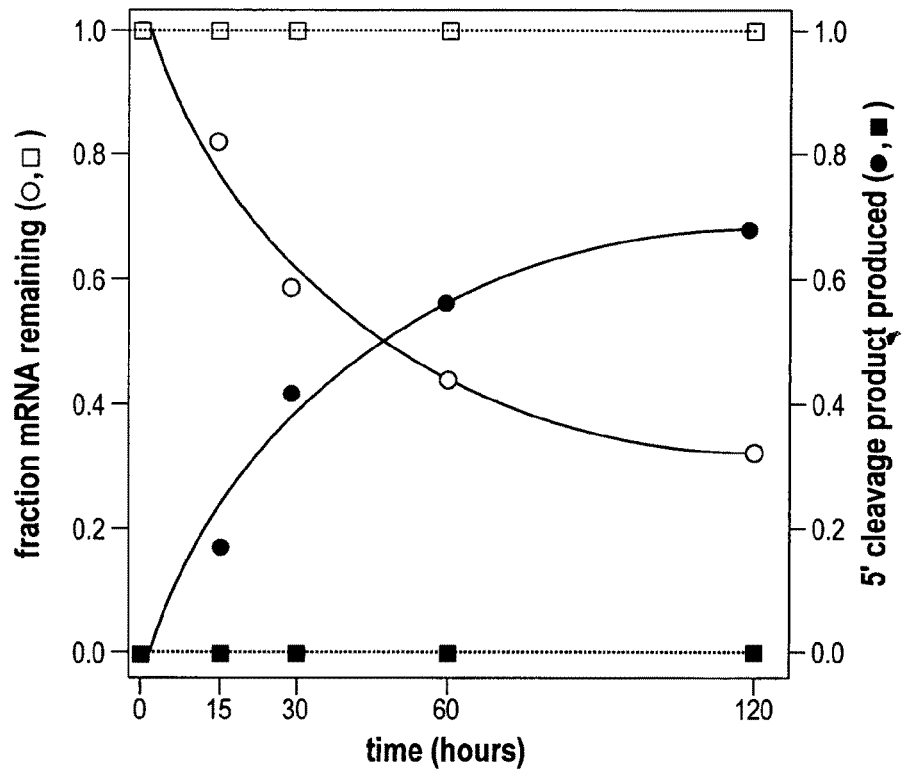

*Fig. 1B*

Wild type SOD1

5'- ...ACTGCTGACAAAGATGGTGTGGCCGATGTGTCTAT...-3' (SEQ ID NO.:15)

G93AshRNA    GACAAAGAUGCUGUGGCCGAU<sup>AA</sup>G   (SEQ ID NO.:16)
             UUUUCUGUUUCUACGACACCGGCUA<sub>UU</sub>C atkavcvlk gdgpvqgiin feqkesngpv kvwgsikglt eglhgfhvhe fgdntagcts
agphfnplsr khggpkdeer hvgdlgnvta dkdgvadvsi edsvislsgd hciigrtlvv
hekaddlgkg gneestktgn agsrlacgvi giaq

```
gcgacgaagg ccgtgtgcgt gctgaagggc gacggcccag tgcagggcat catcaatttc gagcagaagg
aaagtaatgg accagtgaag gtgtggggaa gcattaaagg actgactgaa ggcctgcatg gattccatgt
tcatgagttt ggagataata cagcaggctg taccagtgca ggtcctcact ttaatcctct atccagaaaa
cacggtgggc caaaggatga agagaggcat gttggagact tgggcaatgt gactgctgac aaagatggtg
tggccgatgt gtctattgaa gattctgtga tctcactctc aggagaccat tgcatcattg gccgcacact
ggtggtccat gaaaaagcag atgacttggg caaggtgggg aatgaagaaa gtacaaagac aggaaacgct
ggaagtcgtt tggcttgtgg tgtaattggg atcgcccaa
```

*Fig. 8*

```
gtaccctgtttacatcattttgccattttcgcgtcgtactgcaaccggcggggcccacgccgtgaaaagaaggttgttttctccacagtttcgggttctggacg    [-193]
tttccggctgcgggggctgcggggagtctccggcgcacgggagtcctccggcgcccttggcccgcgaccgcactcgcgccactcgcccggcccgacccgaggctgccgagggggc    [-93]
gggctgagcgcgtgcgaggccattggtttgggccagatgggcgaggcgcgaggacctcgcagtagtcgcggagacgagttcgcggcctataaagtagtcgcggagacgggtgctgttttgcgt    [8]
cgtagtctcctgcaggtctgggtttccgttgcagtcctgcagttcgagcagcaggaacctcggcgtggcctagcgagttatggcgacgaaggccgtgtcgtgctga    [108]
agggcgacggccagtgcaggcatcatcaatttcgagcaggacgttcgagcgccagggctaagcagcttgctggaggttcactggctggcagaaagtgtcagcctggattgc    [208]
ccccgcgacccttgcatgacgggtcgccgcccaggctagagcgtaagcagttcactgtgggagttcactgggagttaaatcagctgtttttcttgttcagaaactctctcaac    [308]
atggacggatttttccactcccaagtctgcgtgctcttttacttcactgtgaggtaaagcattaaaaggactgactgaaggcctgtttttcatgaggagcttcatgttcatgagtttg    [408]
tttgcactttttcttaaaggaaagtaatgaccagtaatgaccactgtgggagaagcattaaaaggactgactgaaggcctgcagtcatgagttctcattaatcctcttaatcctctatccagaaa    [508]
gagataataacagcaggtggtcataattagctcttttctttcttataagctgcagtcctcacttaatctctatactactactgtaaat    [678]
acacgtgggccaaaggatgaagaggtaacaagatgcttaactcttgtaatcaatggcgatacgtttctgagttcatatgctatactgctttacttcctg    [778]
atgtgcctaagataattccgtgtttcccccaccttttgcttttgaactgctttttgtagcattgtttttgtagcattgattgaatatacaagtgccaaaggggaactaatacag    [878]
ggcttaaaggaattgacaaatggcacttaaaacgattggtttttgtagcattgattgaattgtgagcatccaaatcattgatgtcttccatataggcatgttgggacttgggcaatgtgactgctga    [978]
gaaatgttcatgaacagtactgtcaaccactagtcaaatcattgatctctcactctgaattgtgttcatctgaagatttcataaa    [1078]
caaagatgtgtgccgatgtgtctattgaagattctgatctcactctgaattgtgttcatctgaagatttcataaa    [1178]
ggatatgcataaaacttcttctaacagtacagtcatgtatcttcactgtatatcagccttgatggcgagatccagataaaactgtgttctgctttt    [1278]
aaactactaaatattagtatatctctactaggattatctttcttaaaattttctaatattatgaggttctaaacatctttggtattgttgggaggagta    [1378]
gtgattacttgacagcccaaagtcgttggtttgctgttgtaaccactgtaaaatgggatgatgctttaacacatctttggtattgttgggaggagta    [1478]
acaggaaacgctggaagtcgttggtttgctgttgtgtaatttggatgcgccaataaacattccctttgatgtagtctgaggccccttaactcatctgttatc    [1578]
ctgctagctgtagaaatgtatcctgataaatgtaatccctcgattaaaaaaaggtgtgtgacttttcagagttgcttttaagtacctgtagtg    [1678]
agaaactgatttatgatcacttgagaatttcttttgtcattcaagcttcaatgactgtcgtttcaatgactgtcaatgactgtcgtttcaatgacctgtatttgccagacttaaaatcaca    [1778]
gatggtattaactgctctgatacttatttatataaacagcttagtaatacagatttagtaatacagttagtaatacagatcattttatttgaaagtgttttgaga    [1878]
aactaaattagctctgatacttatttatataaacagttagtaatacagttagtaatacagttagtaatacaacacaactctgctagacaaataggctgtcccttgaagctt.........    [1978]
ccatcaaaatgcatactttaaaacagctgtctttagctttagcttagctaaaacagttagtaatacaacacaactctgctagacaaataggctgtcccttgaagctt.........    [2066]
```

Scrambled siRNA (SEQ ID NO.:42)
5'-GAGuCUaGGcCAuUGaGAC$^{UUC}$A
　　 * * * * * * * * * * * * * * * * * A
3'-UUCUCaGAuCCgGUaACuCUG$_{AGA}$G A1-19 (SEQ ID NO.:43)
5'-GAGACUUGGGCAAUGUGAC$^{UUC}$A
　　 * * * * * * * * * * * * * * * * * A
3'-UU$\underline{A}$UCUGAACCCGUUACACUG$_{AGA}$G A2-19 (SEQ ID NO.:44)
5'-GAGACUUGGGCAAUGUGAC$^{UUC}$A
　　 *　* * * * * * * * * * * * * * * * A
3'-UUC$\underline{A}$CUGAACCCGUUACACUG$_{AGA}$G A3-19 (SEQ ID NO.:45)
5'-GAGACUUGGGCAAUGUGAC$^{UUC}$A
　　 * *　* * * * * * * * * * * * * * A
3'-UUCU$\underline{A}$UGAACCCGUUACACUG$_{AGA}$G A4-19 (SEQ ID NO.:46)
5'-GAGACUUGGGCAAUGUGAC$^{UUC}$A
　　 * * *　* * * * * * * * * * * * * A
3'-UUCUC$\underline{A}$GAACCCGUUACACUG$_{AGA}$G P11-19 (SEQ ID NO.:47)
5'-GAGACUUGGGCAAUGUGAC$^{UUC}$A
　　 * * * * * * * * * * * * * * * * * A
3'-UUCUCUGAACCCGUUACACUG$_{AGA}$G S1-19 (SEQ ID NO.:48)
5'-GAGACUUGGGCAAUGUGA$\underline{A}$$^{UUC}$A
　　 * * * * * * * * * * * * * * * * * A
3'-UUCUCUGAACCCGUUACACUG$_{AGA}$G S2-19 (SEQ ID NO.:49)
5'-GAGACUUGGGCAAUGUGU$\underline{C}$$^{UUC}$A
　　 * * * * * * * * * * * * * * * * * A
3'-UUCUCUGAACCCGUUACACUG$_{AGA}$G S3-19 (SEQ ID NO.:50)
5'-GAGACUUGGGCAAUGU$\underline{A}$AC$^{UUC}$A
　　 * * * * * * * * * * * * * * * * * A
3'-UUCUCUGAACCCGUUACACUG$_{AGA}$G S4-19 (SEQ ID NO.:51)
5'-GAGACUUGGGCAAUG$\underline{A}$GAC$^{UUC}$A
　　 * * * * * * * * * * * * * * * * * A
3'-UUCUCUGAACCCGUUACACUG$_{AGA}$G

B

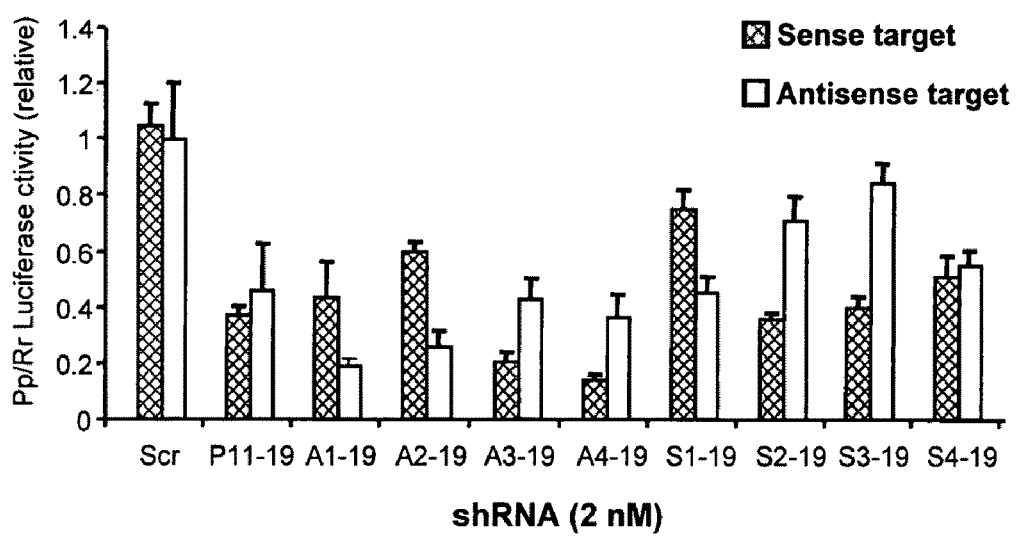

Fig. 13

A scrambled siRNA (S)(SEQ ID NO.:52)
5'-GAGuCUaGGcCAuUGaGACUG<sup>UUC</sup>A
   ******************  A
3'-UUCUCaGAuCCgGUaACuCUGAC<sub>AGA</sub>G A1-21                    (SEQ ID NO.:53)
5'-GAGACUUGGGCAAUGUGACUG<sup>UUC</sup>A
   ******************  A
3'-UUAUCUGAACCCGUUACACUGAC<sub>AGA</sub>G A2-21                    (SEQ ID NO.:54)
5'-GAGACUUGGGCAAUGUGACUG<sup>UUC</sup>A
   * ****************  A
3'-UUCACUGAACCCGUUACACUGAC<sub>AGA</sub>G A3-21                    (SEQ ID NO.:55)
5'-GAGACUUGGGCAAUGUGACUG<sup>UUC</sup>A
    **************  A
3'-UUCUAUGAACCCGUUACACUGAC<sub>AGA</sub>G A4-21                    (SEQ ID NO.:56)
5'-GAGACUUGGGCAAUGUGACUG<sup>UUC</sup>A
   * **************  A
3'-UUCUCAGAACCCGUUACACUGAC<sub>AGA</sub>G P11-21                   (SEQ ID NO.:57)
5'-GAGACUUGGGCAAUGUGACUG<sup>UUC</sup>A
   ********************  A
3'-UUCUCUGAACCCGUUACACUGAC<sub>AGA</sub>G S1-21                    (SEQ ID NO.:58)
5'-GAGACUUGGGCAAUGUGACUA<sup>UUC</sup>A
   *******************_  A
3'-UUCUCUGAACCCGUUACACUGAC<sub>AGA</sub>G S2-21                    (SEQ ID NO.:59)
5'-GAGACUUGGGCAAUGUGACAG<sup>UUC</sup>A
   ****************** *  A
3'-UUCUCUGAACCCGUUACACUGAC<sub>AGA</sub>G S3-21                    (SEQ ID NO.:60)
5'-GAGACUUGGGCAAUGUGAAUG<sup>UUC</sup>A
   ***************   A
3'-UUCUCUGAACCCGUUACACUGAC<sub>AGA</sub>G S4-21                    (SEQ ID NO.:61)
5'-GAGACUUGGGCAAUGUGUCUG<sup>UUC</sup>A
   *************** *  A
3'-UUCUCUGAACCCGUUACACUGAC<sub>AGA</sub>G

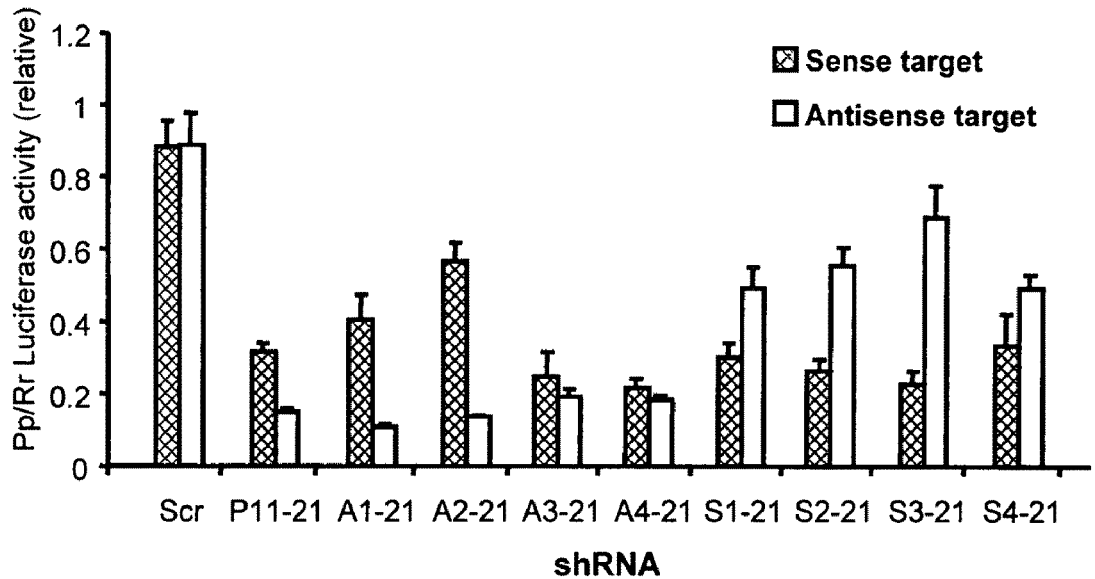

Fig. 14

A shsod1a     (SEQ ID NO.:71)
5'-GAGGCAUGUUGGAGACUUGGG$^{UUC}$A
   ******************* A
3'-UUCUCCGUACAACCUCUGAACCC$_{AGA}$G shsod1a-A2     (SEQ ID NO.:72)
5'-GAGGCAUGUUGGAGACUUGGG$^{UUC}$A
   * ***************** A
3'-UUCACCGUACAACCUCUGAACCC$_{AGA}$G shsod1a-S3     (SEQ ID NO.:73)
5'-GAGGCAUGUUGGAGACUUAGG$^{UUC}$A
   ***************  A
3'-UUCUCCGUACAACCUCUGAACCC$_{AGA}$G shsod1b     (SEQ ID NO.:74)
5'-GUUGGAGACUUGGGCAAUGUG$^{UUC}$A
   ******************* A
3'-UUCAACCUCUGAACCCGUUACAC$_{AGA}$G shsod1b-A2     (SEQ ID NO.:75)
5'-GUUGGAGACUUGGGCAAUGUG$^{UUC}$A
   * ***************** A
3'-UUCUACCUCUGAACCCGUUACAC$_{AGA}$G shsod1b-S3     (SEQ ID NO.:76)
5'-GUUGGAGACUUGGGCAAUAUG$^{UUC}$A
   ***************  A
3'-UUCAACCUCUGAACCCGUUACAC$_{AGA}$G shsod1c     (SEQ ID NO.:77)
5'-AAUGUGACUGCUGACAAAGAU$^{UUC}$A
   ******************* A
3'-UUUUACACUGACGACUGUUUCUA$_{AGA}$G shsod1c-A2     (SEQ ID NO.:78)
5'-AAUGUGACUGCUGACAAAGAU$^{UUC}$A
   * ***************** A
3'-UUUAACACUGACGACUGUUUCUA$_{AGA}$G shsod1c-S3     (SEQ ID NO.:79)
5'-AAUGUGACUGCUGACAAAUAU$^{UUC}$A
   ***************  A
3'-UUUUACACUGACGACUGUUUCUA$_{AGA}$G

B

*Fig. 16*

ALLELE-SPECIFIC RNA INTERFERENCE

STATEMENT AS TO FEDERALLY FUNDED RESEARCH

The U.S. government may have certain rights in this invention pursuant to Grant Nos: GM62862 and GM53874 awarded by the National Institute of Health (NIH) and Grant Nos: NS35750 and NS41739-01 awarded by the National Institute of Neurological Disorders and Stroke (NINDS).

BACKGROUND

Diseases caused by dominant, gain-of-function gene mutations develop in heterozygotes bearing one mutant and one wild type copy of the gene. Some of the best-known diseases of this class are common neurodegenerative diseases, including Alzheimer's disease, Huntington's disease, Parkinson's disease and amyotrophic lateral sclerosis (ALS; "Lou Gehrig's disease") (Taylor et al., 2002). In these diseases, the exact pathways whereby the mutant proteins cause cell degeneration are not clear, but the origin of the cellular toxicity is known to be the mutant protein.

Mutations in SOD1 cause motor neuron degeneration that leads to ALS, because the mutant protein has acquired some toxic property (Cleveland et al., 2001). Neither the nature of this toxic property nor the downstream pathway that leads to the eventual motor neuron degeneration is understood. In mice, only expression of the mutant SOD1, but not elimination of SOD1 by gene knockout, causes ALS. Nonetheless, the gene knockout mice develop numerous abnormalities including reduced fertility (Matzuk et al., 1990), motor axonopathy (Shefner et al., 1999), age-associated loss of cochlear hair cells (McFadden et al., 2001) and neuromuscular junction synapses (Flood et al., 1999), and enhanced susceptibility to a variety of noxious assaults, such as excitotoxicity, ischemia, neurotoxins and irradiation, on the CNS and other systems (Matz et al., 2000; Kondo et al., 1997; Kawase et al., 1999; Behndig et al., 2001). Given the toxicity of the mutant and the functional importance of the wild-type protein, the ideal therapy for this disease would selectively block the expression of the mutant protein while retaining expression of the wild type.

SUMMARY

The present invention relates to novel methods for treating dominant gain-of-function disease. In particular, the invention provides methods for the selective destruction of mutant mRNA's transcribed from gain-of-function genes, thus preventing the production of mutant proteins encoded by such genes. The invention is based in part on the discovery that both small interfering RNAs (siRNAs) and small hairpin RNAs (shRNAs) can be designed to selectively inhibit expression of a mutant allele, e.g., G85R SOD1 or G93A SOD1, while preserving expression of the wild-type protein, with single-nucleotide specificity.

The methods of the invention utilize RNA interference technology (RNAi) against selected point mutations occurring in a single allele in a mutant gene e.g., the point mutation in the copper zinc superoxide dismutase (SOD1) gene associated with amyotrophic lateral sclerosis (ALS). RNAi can mediate sequence-selective suppression of gene expression in a wide variety of eukaryotes by introducing short RNA duplexes (called small interfering RNAs or siRNAs) with sequence homologies to the target gene (Caplen et al., 2001; Elbashir et al., 2001c). siRNA duplexes or vectors expressing shRNAs of the present invention can be used to silence the expression of a toxic mutant gene selectively e.g., the SOD1 mutant protein, thereby allowing the wild-type SOD1 allele to continue functioning.

The invention is also based on the discovery of new artificial, engineered RNA precursors, that when expressed in a cell, e.g., in-vivo, are processed by the cell to produce targeted siRNAs that selectively silence mutant alleles of target genes (by targeting specific mRNAs for cleavage) using the cell's own RNAi pathway. By introducing nucleic acid molecules that encode these engineered RNA precursors into cells in-vivo with appropriate regulatory sequences (e.g., a transgene in a vector such as a plasmid), expression of the engineered RNA precursors can be selectively controlled both temporally and spatially, i.e., at particular times and/or in particular tissues, organs, or cells.

In one aspect, the invention features a method of inhibiting expression of a target allele in a cell comprising at least two different alleles of a gene by administering to the cell an siRNA specific for the target allele. In one embodiment, the target allele is correlated with a disorder associated with a dominant, gain of function mutation. In another embodiment, the disorder is amyotrophic lateral sclerosis, Huntington's disease, Alzheimer's disease, or Parkinson's disease.

In another aspect, the invention features a method of treating a subject having a disorder correlated with the presence of a dominant, gain-of-function mutant allele, the method comprising administering to the subject a therapeutically effective amount of an siRNA specific for the mutant allele. In one embodiment, the siRNA is targeted to the gain-of-function mutation. In another embodiment, the disorder is amyotrophic lateral sclerosis, Huntington's disease, Alzheimer's disease, or Parkinson's disease.

In one embodiment, the disease is amyotrophic lateral sclerosis. In a further embodiment, the allele is a SOD1 mutant allele.

In one embodiment, the siRNA targets a mutant SOD1 allele (SEQ ID NO:8) and comprises or consists of a mutant siRNA sequence as set forth in FIG. 1A with P10 (SEQ ID NO:4) being preferred, followed by P9 (SEQ ID NO:2), followed by P11 (SEQ ID NO:6).

In another embodiment, the siRNA (e.g., a control siRNA) targets a wild-type SOD1 allele and comprises or consists of a wild-type siRNA sequence as set forth in FIG. 1A with P9 (SEQ ID NO:14) or P10 (SEQ ID NO:12) being preferred, followed by P11 (SEQ ID NO:10).

In another aspect, the invention provides an siRNA comprising a sequence as set forth in FIG. 1A.

In another aspect, the invention provides a p10 mutant siRNA comprising the sequence as set forth in FIG. 1A (SEQ ID NO: 4).

In another aspect, the invention provides a p9 mutant siRNA comprising the sequence as set forth in FIG. 1A (SEQ ID NO: 2).

In another aspect, the invention provides a G93A SOD1 shRNA comprising the sequence as set forth in FIG. 3A (SEQ ID NO: 16), as well as expression constructs comprising the shRNAs of the invention.

In another aspect, the invention provides therapeutic compositions comprising the siRNAs and/or shRNAs of the invention, and a pharmaceutically acceptable carrier.

In another aspect, the invention provides asymmetric RNAi agents (e.g. asymmetric shRNAs) which are capable of mediating RNA intereference (e.g. allele-specific RNA interference) with enhanced specificity and efficacy.

Other features and advantages of the invention will be apparent from the following detailed description, and from the claims.

DESCRIPTION OF DRAWINGS

FIG. 1. siRNA duplexes can discriminate between mutant and wild-type SOD1 in-vitro. (A) siRNA duplexes used: mutant siRNA P11 (SEQ ID NO: 5, sense; SEQ ID NO: 6, anti-sense or guide), mutant siRNA P10 (SEQ ID NO: 3, sense; SEQ ID NO: 4, anti-sense or guide), mutant siRNA P9 (SEQ ID NO: 1, sense; SEQ ID NO: 2 anti-sense or guide), SOD1 wild-type target (SEQ ID NO: 7), SOD1 mutant target (SEQ ID NO: 8), wild-type siRNA P11 (SEQ ID NO: 9 sense; SEQ ID NO: 10, anti-sense or guide), wild-type siRNA P10 (SEQ ID NO: 11, sense; SEQ ID NO: 12, anti-sense or guide), wild-type siRNA P9 (SEQ ID NO: 13, sense; SEQ ID NO: 14, anti-sense or guide) (B) Mutant siRNA p10 targets mutant but not wild-type SOD1 mRNA for destruction by the RNAi pathway.

FIG. 8 is the Genbank entry for human SOD-1 mRNA, Accession No. NM_000454, showing the nucleotide sequence of wild-type SOD-1 (SEQ ID NO:17).

FIG. 9 is the SOD1 genomic sequence (SEQ ID NO: 19)

FIG. 11A depict the sense and antisense target sequences that were inserted into the 3' UTR (top left), P11 siRNA and its variations with mismatches placed at the either end of the siRNA. FIG. 11B depicts the silencing efficacy of the various siRNAs. The sense strand of the siRNA and its corresponding target sequence ("antisense target") are indicated in bold (SEQ ID NOS 20-41 are disclosed respectively in order of appearance).

FIG. 13 depicts data which demonstrates that the strand preference of shRNAs with a 19 nt stem is not predicted by the asymmetry rule. FIG. 13A depicts the sequences of shRNAs with a 19 nt stem. Mismatches were placed at the first 4 positions of either strand of the stems. The sense strand of the shRNA and its corresponding target sequence ("antisense target") are indicated in bold. FIG. 13B depicts the results of a dual luciferase assay to evaluate the relative silencing efficacy of the shRNAs against a sense or antisense target. All the targets, including both the sense and antisense strands, perfectly complemented their siRNA strands (SEQ ID NOS 42-51 are disclosed respectively in order of appearance).

FIG. 14 depicts data which demonstrates that the strand preference of shRNAs with a 21 nt is predicted by the asymmetry rule. FIG. 14A depits the sequences of shRNAs with 21 nt stem. Mismatches were placed at the first 4 positions of either strand of the stems. The sense strand of the shRNA and its corresponding target sequence ("antisense target") are indicated in bold. FIG. 14B depicts the results of a dual luciferase assay to evaluate the relative silencing efficacy of the shRNAs against a sense or antisense target. All the targets, including both the sense and antisense strands, perfectly complemented their siRNA strands (SEQ ID NOS 52-61 are disclosed respectively in order of appearance).

FIG. 15A is a schematic depicting processing of shRNA as predicted by the asymmetry rule. The thickness of the arrows indicates the degree of preference for incorporation of the siRNA strand into the RISC complex. The sense strand of the shRNA and its corresponding target sequence ("antisense target") are indicated in bold. FIG. 15B depicts a Northern blot demonstrating the presence of shRNA and processed siRNA strands. In each lane, total RNA from HEK293 cells transfected with the indicated shRNA constructs was loaded. The blots were detected using either the sense or the antisense RNA probes (SEQ ID NOS 62-70 are disclosed respectively in order of appearance).

FIG. 16 depicts data which demonstrates that a mismatch at the 3rd position of the strand distal to the loop of a shRNA results in optimized shRNAs with favorable strand preference. FIG. 16A depicts the sequences of three sets of shRNAs with either no or mismatches placed at the A2 or S3 positions. The sense strand of the shRNA and its corresponding "off-target" sequence ("antisense target") are indicated in bold. FIG. 16B depicts the results of a dual luciferase assay to evaluate the relative silencing efficacy of the shRNAs against a sense or antisense target. All the targets, including both the sense and antisense strands, perfectly complement their siRNA strands (SEQ ID NOS 71-79 are disclosed respectively in order of appearance).

DETAILED DESCRIPTION

Figure 2:
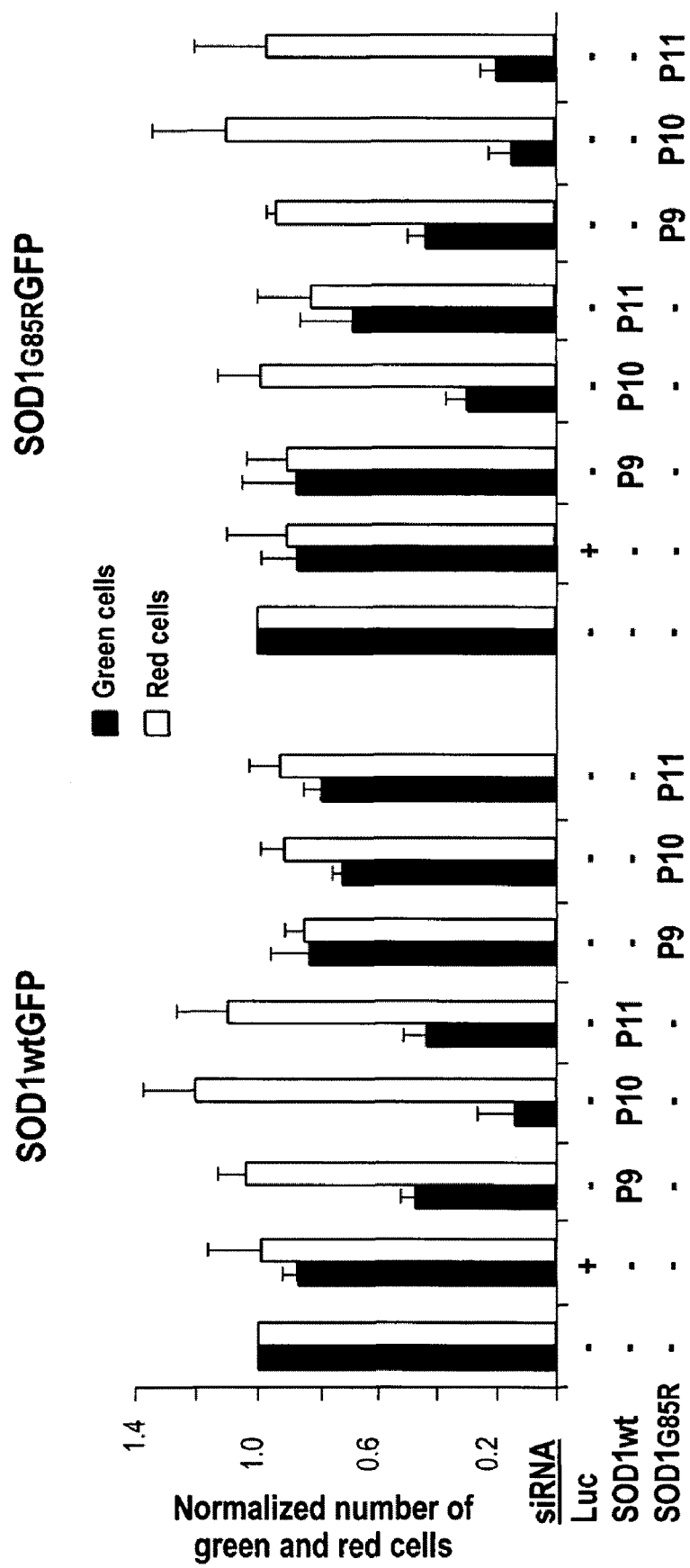
FIG. 2. Selective inhibition of mutant SOD1 G85R expression by siRNA in Hela cells. SOD1wtGFP or G85R-GFP were cotransfected with various siRNAs. DsRed was cotransfected as a transfection control. Green and red fluorescent cells were quantified using FACS. (A) Relative number of green (solid bars) and red (open bars) cells in the transfections (n=3). Error bars represent standard deviation.

Mutations in copper zinc superoxide dismutase (SOD1) gene cause a subset of amyotrophic lateral sclerosis, a neurodegenerative disease that leads to motor neuron degeneration, paralysis and death (Brown and Robberecht, 2001; Siddique and Lalani, 2002). It has been well established that mutant SOD1 causes motor neuron degeneration by acquisition of a toxic property (Cleveland and Rothstein, 2001). However, neither the molecular basis of this toxic property nor mechanism that leads to motor neuron death is understood. Because of this incomplete understanding of the disease mechanism, rational design of therapy has not produced robust efficacious outcomes. On the other hand, because the toxicity that kills motor neurons originates from the mutated protein (Cleveland and Rothstein, 2001), decrease of the mutant protein should alleviate or even prevent the disease. RNA interference (RNAi) technology can be used to achieve this goal.

The present invention is based on the discovery that siRNA and shRNA can selectively inhibit the expression of a mutant allele, even when the mutant mRNA differs from wild-type by only a single nucleotide, as is the case with certain mutations, e.g., mutations of SOD1 correlated with ALS. These methods are applicable to the treatment of diseases that are caused by dominant, gain-of-function type of gene mutations, including, but not limited to, ALS. The siRNAs of the present invention are capable of single nucleotide discrimination and selectively down-regulating expression of their target genes.

The methods of the invention utilize RNA interference technology (RNAi) against selected point mutations occurring in a single allele in the mutant gene e.g., the point mutation in the copper zinc superoxide dismutase (SOD1) gene associated with amyotrophic lateral sclerosis (ALS). RNAi can mediate sequence-selective suppression of gene expression in a wide variety of eukaryotes by introducing short RNA duplexes (called small interfering RNAs or siRNAs) with sequence homologies to the target gene (Caplen et al., 2001; Elbashir et al., 2001c). siRNA duplexes or vectors expressing shRNAs of the present invention can be used to silence the expression of a toxic mutant gene selectively e.g., the SOD1 mutant protein, thereby allowing the wild-type SOD1 allele to continue functioning.

Sequence-selective, post-transcriptional inactivation of gene expression can be achieved in a wide variety of eukaryotes by introducing double-stranded RNA corresponding to the target gene, a phenomenon termed RNAi (Hutvagner and Zamore, 2002; Hannon, G. J., 2002; McManus and Sharp, 2002). RNAi methodology has been extended to cultured mammalian cells (Caplen et al, 2001; Elbashir et al., 2001). This approach takes advantage of the discovery that siRNA, an intermediate in the RNAi pathway, can trigger the degradation of mRNA corresponding to the siRNA sequence. Furthermore, shRNA transcribed in-vivo can trigger degradation of target RNAs complementary to the sequence of the shRNA stem, because shRNA is processed into siRNA in cells (Paul et al., 2002; Lee et al., 2002; Paddison et al., 2002; Sui et al., 2002; Yu et al., 2002; McManus et al., 2002; Zeng et al., 2002; Brummelkamp et al., 2002; Miyagishi et al., 2002; Jacque et al., 2002). The present applicants demonstrate that siRNA duplexes or viruses expressing shRNA can be used to preferentially block the expression of a mutant allele, while preserving the expression of a co-expressed wild type allele.

The vast majority of ALS-associated SOD1 mutations are single nucleotide point mutations resulting in single amino acid changes (ALS online database for ALS genetic (SOD1, ALS and other) mutations). Thus, to selectively silence the expression of the mutant, but not the wild type, single nucleotide specificity is required. Applicants have now shown that single nucleotide discrimination is achievable in mammalian cells.

So that the invention maybe more readily understood, certain terms are first defined:

An "isolated nucleic acid molecule or sequence" is a nucleic acid molecule or sequence that is not immediately contiguous with both of the coding sequences with which it is immediately contiguous (one on the 5' end and one on the 3' end) in the naturally occurring genome of the organism from which it is derived. The term therefore includes, for example, a recombinant DNA or RNA that is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide sequence.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

The term "engineered," as in an engineered RNA precursor, or an engineered nucleic acid molecule, indicates that the precursor or molecule is not found in nature, in that all or a portion of the nucleic acid sequence of the precursor or molecule is created or selected by man. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising ~21 nucleotides (or nucleotide analogs), for example, 19, 20, 21 or 22 nucleotides. The term "long" siRNA refers to a siRNA comprising ~24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11 (5): 317-25, Vorobjev et al. Antisense Nucleic Acid Drug Dev. 2001 Apr. 11(2):77-85, and U.S. Pat. No. 5,684,143. Certain of the above-referenced modifications (e.g., phosphate group modifications) preferably decrease the rate of hydrolysis of, for example, polynucleotides comprising said analogs in-vivo or in-vitro.

As used herein, the term "antisense strand" of an siRNA or RNAi agent e.g., an antisense strand of an siRNA duplex or siRNA sequence, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific RNA interference (RNAi), e.g., complementarity sufficient to trigger the destruction of the desired target mRNA by the RNAi machinery or process. The term "sense strand" or "second strand" of an siRNA or RNAi agent e.g., an antisense strand of an siRNA duplex or siRNA sequence, refers to a strand that is complementary to the antisense strand or first strand. Antisense and ssense strands can also be referred to as first or second strands, the first or second strand having complementarity to the target sequence and the respective second or first strand having complementarity to said first or second strand.

As used herein, the term "guide strand" refers to a strand of an RNAi agent, e.g., an antisense strand of an siRNA duplex or siRNA sequence, that enters into the RISC complex and directs cleavage of the target mRNA.

As used herein, the term "asymmetry", as in the asymmetry of the duplex region of an RNAi agent (e.g. the stem of an shRNA), refers to an inequality of bond strength or base pairing strength between the termini of the RNAi agent (e.g., between terminal nucleotides on a first strand or stem portion and terminal nucleotides on an opposing second strand or stem portion), such that the 5' end of one strand of the duplex is more frequently in a transient unpaired, e.g, single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, Van der Waals interactions, and the like between said nucleotides (or nucleotide analogs).

As used herein, the "5' end", as in the 5' end of an antisense strand, refers to the 5' terminal nucleotides, e.g., between one and about 5 nucleotides at the 5' terminus of the antisense strand. As used herein, the "3' end", as in the 3' end of a sense strand, refers to the region, e.g., a region of between one and about 5 nucleotides, that is complementary to the nucleotides of the 5' end of the complementary antisense strand.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phophoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

A "target gene" is a gene whose expression is to be selectively inhibited or "silenced." This silencing is achieved by cleaving the mRNA of the target gene by an siRNA that is created from an engineered RNA precursor by a cell's RNAi system. One portion or segment of a duplex stem of the RNA precursor is an anti-sense strand that is complementary, e.g., fully complementary, to a section of about 18 to about 40 or more nucleotides of the mRNA of the target gene.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder "Allele specific inhibition of expression" refers to the ability to significantly inhibit expression of one allele of a gene over another, e.g., when both alleles are present in the same cell. For example, the alleles can differ by one, two, three or more nucleotides. In some cases, one allele is associated with disease causation, e.g., a disease correlated to a dominant gain-of-function mutation.

The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

The phrase "examining the function of a gene in a cell or organism" refers to examining or studying the expression, activity, function or phenotype arising therefrom.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Various aspects of the invention are described in further detail in the following subsections.

I. Gain-Of-Function Disorders

Gain-of-function disorders are a class of disease or disorders characterized by a gain-of-function mutation. The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein. In yet another embodiment, the disease or disorders of the present invention include neurodegenerative disease caused by a gain-of-function mutation. For example, Amyotrophic Lateral Sclerosis, Alzheimer's disease, Huntington's disease, and Parkinson's disease are associated with gain-of-function mutations in the genes encoding SOD1, Amyloid Precursor Protein or APP (see Ikezu et al, *EMBO J.*, (1996), 15(10):2468-75), Huntingtin or htt (see Rubinsztein, *Trends Genet.*, (2002), 18(4):202-9), and alpha-synuclein (see, for example, Cuervo et al., *Science*, (2004), 305(5688): 1292-5), respectively. In another embodiment, disease or disorders of the present invention include neurodegenerative disease caused by a gain-of-function mutation in an oncogene, e.g., cancers caused by a mutation in the ret oncogene (e.g., ret-1), for example, gastrointestinal cancers, endocrine tumors, medullary thyroid tumors, parathyroid hormone tumors, multiple endocrine neoplasia type2, and the like. In a more preferred embodiment, the disease or disorder of the present invention is Amyotrophic Lateral Sclerosis.

A. Amyotrophic Lateral Sclerosis (ALS)

Amyotrophic lateral sclerosis (ALS), also known as Lou Gehrig's disease, is a progressive, fatal neurodegenerative disorder involving the motor neurons of the cortex, brain stem, and spinal cord (Hirano, A., 1996, Neurology 47 (Suppl. 2), S63-S66). The disease is caused by a dominant, gain-of-function mutation that develops in people bearing one mutant and one wild type copy of the gene e.g., SOD1. ALS causing SOD1 mutations are single-nucleotide point mutations that alter a single amino acid in the protein. The disease is further characterized by a progressive motor neuron degeneration leading to paralysis, to total loss of motor and respiratory functions, and eventually to death two to eight years after the appearance of the first clinical signs (mean duration after onset three years). ALS is of genetic origin in 10% of the patients, and sporadic in 90% of the cases. Point mutations in the gene encoding for copper zinc superoxide dismutase (SOD1) localized on chromosome 21q22-1 are responsible for the pathology in 20% of the familial cases (Rosen et al., Mutations in Cu/Zn superoxide dismutase gene are associated with familial amyotrophic lateral sclerosis, Nature, 362, 59-62, 1993, review in Rowland, Amyotrophic lateral sclerosis: Human challenge for neuroscience, Proc. Natl. Acad. Sci. USA, 92, 1251-1253, 1995). Thus, defective SOD1 is linked to motor neuron death and carries implications for understanding and possible treatment of familial amyotrophic lateral sclerosis.

i. The SOD-1 Gene

SOD1 is a metalloenzyme that contains one copper and one zinc, and is present in the cytoplasm as a homodimer. Copper is required for enzymatic activity while zinc stabilizes the protein's structure (Fridovich, 1986). SOD1 is a expressed in all eukaryotic cells and is one of a family of three SOD enzymes, including manganese-dependent, mitochondrial SOD (SOD2) and copper/zinc extracellular SOD (SOD3) (I Fridovich, 1986, "Superoxide dismutases," Advances in Enzymology 58: 61-97). The main natural function of SOD1 is superoxide dismutation, in which superoxide ($O_2^-$) is converted to hydrogen peroxide ($H_2O_2$) and oxygen. Together with the downstream enzymes catalase and glutathione peroxidase (which convert $H_2O_2$ to water and oxygen), SOD1 detoxifies cellular free radicals. The importance of this function is underscored by numerous abnormalities in mice lacking the SOD1 gene, including reduced fertility (Matzuk et al., 1998), motor axonopathy (Shefner et al., 1999), increased age-associated loss of cochlear hair cells (McFadden et al., 2001) and neuromuscular junction synapses (Flood et al., 1999), and enhanced susceptibility to a variety of noxious assaults on the nervous system, such as axonal injury (Reaume et al., 1996), ischemia (Kondo et al., 1997; Kawase et al., 1999), hemolysate exposure (Matz et al., 2000) and irradiation (Behndig et al., 2001). Given the toxicity of the mutant protein and the functional importance of the wild-type, the ideal therapy for ALS would be to selectively block expression of the mutant SOD1 protein while retaining expression of the wild-type SOD1 protein.

The present invention, targets mutant SOD1 using RNAi. The method utilized in RNAi comprises one strand of double-stranded RNA (siRNA) which complements a region containing a point mutation within the mutant SOD1 mRNA. After introduction of siRNA into neurons, the siRNA partially unwinds, binds to the region containing the point mutation within the SOD1 mRNA in a site-specific manner, and activates an mRNA nuclease. This nuclease cleaves the SOD1 mRNA, thereby halting translation of the mutant SOD1. Cells rid themselves of partially digested mRNA, thus precluding translation, or cells digest partially translated proteins. Neurons survive on the wild-type SOD1 (from the normal allele); this approach prevents the ravages of mutant SOD1 by eliminating its production.

The amino acid sequence of human wild-type SOD1 protein is set forth in FIG. 1 (SEQ ID NO:18). A consensus nucleotide sequence of human wild-type SOD1 gene (cDNA) is set forth in FIG. 2 (SEQ ID NO:17)

ii. SOD-1 Mutant Gene

More than 100 SOD1 mutations have been identified. Most of these mutations produce a single amino acid replacement in the superoxide dismutase enzyme's chain of amino acids. The most common substitution, which occurs in 50 percent of American patients with type 1 amyotrophic lateral sclerosis, is the replacement of arginine with valine at position 4 in the amino acid chain (also written as Arg4Val).

SOD1 mutations affect the age when symptoms of type 1 amyotrophic lateral sclerosis begin and how fast the disease progresses. The Arg4Val mutation, for example, results in an aggressive form of the disorder with a survival time of less than 2 years after disease onset. The replacement of glycine with arginine at position 37 (Gly37Arg) is associated with early onset of the disease but a longer survival time. In addition, other factors in combination with SOD1 mutations probably vary the course of type 1 amyotrophic lateral sclerosis. For example, mutations in both the SOD1 gene and a gene known as CNTF appear to accelerate the onset of the disease. The CNTF mutation alone has no ill effects, but in combination with the SOD1 mutation, disease symptoms appear decades earlier compared to other affected family members.

It remains unclear how SOD1 mutations lead to the selective death of motor neurons, which are the specialized nerve cells in the brain and spinal cord that control muscle movement. The superoxide dismutase enzyme is thought to gain a new (but still undefined) toxic function as a result of changes in the SOD1 gene. The malfunctioning enzyme may cause the death of motor neurons through an accumulation of harmful superoxide radicals, abnormal production of other types of toxic radicals, promotion of cell suicide (apoptosis), clumping of the enzyme with other cell proteins, or continued stimulation of motor neurons that cause them to burn out and die (excitotoxicity).

TABLE 1

| SOD 1 mutations | | | | | |
|---|---|---|---|---|---|
| Location | nt | aa | | | |
| exon 1 | 93 | 4 | Ala4Ser | Ala4Thr | Ala4Val |
| exon 1 | 99 | 6 | Cys6Gly | Cys6Phe | |

TABLE 1-continued

SOD 1 mutations

| Location | nt | aa | | | |
|---|---|---|---|---|---|
| exon 1 | 103 | 7 | Val7Glu | | |
| exon 1 | 105 | 8 | Leu8Val | Leu8Gln | |
| exon 1 | 112 | 10 | Gly10Val | Gly10Gly | |
| exon 1 | 117 | 12 | Gly12Arg | | |
| exon 1 | 123 | 14 | Val14Met | Val14Gly | |
| exon 1 | 129 | 16 | Gly16Ser | Gly16Ala | |
| exon 1 | 142 | 20 | Phe20Cys | | |
| exon 1 | 144 | 21 | Glu21Lys | Glu21Gly | |
| exon 1 | 148 | 22 | Gln22Leu | | |
| intron 1 | 319 | | 319t > a | | |
| exon 2 | 466 | 37 | Gly37Arg | | |
| exon 2 | 469 | 38 | Leu38Val | Leu38Arg | |
| exon 2 | 478 | 41 | Gly41Ser | Gly41Asp | |
| exon 2 | 485 | 43 | His43Arg | | |
| exon 2 | 491 | 45 | Phe45Cys | | |
| exon 2 | 494 | 46 | His46Arg | | |
| exon 2 | 496 | 47 | Val47Phe | | |
| exon 2 | 500 | 48 | His48Arg | His48Gln | |
| exon 2 | 502 | 49 | Glu49Lys | | |
| exon 2 | 518 | 54 | Thr54Arg | | |
| exon 3 | 645 | 59 | Ser59Ile | Ser59Ser | |
| exon 3 | 663 | 65 | Asn65Ser | | |
| exon 3 | 669 | 67 | Leu67Arg | | |
| exon 3 | 683 | 72 | Gly72Cys | Gly72Ser | |
| exon 3 | 695 | 76 | Asp76Tyr | Asp76Val | |
| exon 4 | 1048 | 80 | His80Arg | | |
| exon 4 | 1059 | 84 | Leu84Val | Leu84Phe | |
| exon 4 | 1062 | 85 | Gly85Arg | | |
| exon 4 | 1066 | 86 | Asn86Ser | | |
| exon 4 | 1068 | 87 | Val87Met | Val87Ala | |
| exon 4 | 1071 | 88 | Thr88delACTGCTGAC | | |
| exon 4 | 1074 | 89 | Ala89Thr | Ala89Val | |
| exon 4 | 1078 | 90 | Asp90Ala | Asp90Val | |
| exon 4 | 1086 | 93 | Gly93Cys | Gly93Arg | Gly93Ser |
| | | | Gly93Asp | Gly93Ala | Gly93Val |
| exon 4 | 1092 | 95 | Ala95Thr | | |
| exon 4 | 1095 | 96 | Asp96Asn | | |
| exon 4 | 1098 | 97 | Val97Met | | |
| exon 4 | 1107 | 100 | Glu100Lys | Glu100Gly | |
| exon 4 | 1110 | 101 | Asp101Asn | Asp101Gly | |
| exon 4 | 1119 | 104 | Ile104Phe | | |
| exon 4 | 1122 | 105 | Ser105delTCACTC | Ser105Leu | |
| exon 4 | 1125 | 106 | Leu106Val | | |
| exon 4 | 1132 | 108 | Gly108Val | | |
| exon 4 | 1144 | 112 | Ile112Thr | Ile112Met | |
| exon 4 | 1146 | 113 | Ile113Phe | Ile113Thr | |
| exon 4 | 1150 | 114 | Gly114Ala | | |
| exon 4 | 1152 | 115 | Arg115Gly | | |
| exon 4 | 1161 | 118 | Val118Leu | Val118insAAAAC | |
| intron 4 | 1415 | | 1415t > g | | |
| exon 5 | 1441 | 124 | Asp124Gly | Asp124Val | |
| exon 5 | 1443 | 125 | Asp125His | | |
| exon 5 | 1446 | 126 | Leu26delTT | Leu26STOP | Leu26Ser |
| exon 5 | 1450 | 127 | Gly127insTGGG | | |
| exon 5 | 1465 | 132 | Glu132insTT | | |
| exon 5 | 1467 | 133 | Glu133del | | |
| exon 5 | 1471 | 134 | Ser134Asn | | |
| exon 5 | 1487 | 139 | Asn139Asn | Asn139Lys | |
| exon 5 | 1489 | 140 | Ala140Gly | Ala140Ala | |
| exon 5 | 1491 | 141 | Gly141STOP | | |
| exon 5 | 1501 | 144 | Leu144Ser | Leu144Phe | |
| exon 5 | 1503 | 145 | Ala145Thr | Ala145Gly | |
| exon 5 | 1506 | 146 | Cys146Arg | | |
| exon 5 | 1509 | 147 | Gly147Arg | | |
| exon 5 | 1512 | 148 | Val148Ile | Val148Gly | |
| exon 5 | 1516 | 149 | Ile149Thr | | |
| exon 5 | 1522 | 151 | Ile151Thr | Ile151Ser | |
| exon 5 | 1529 | 153 | Gln153Gln | | |

IV. RNA Interference

The present invention features methods for suppressing or knocking down expression of proteins (e.g., gain-of-function mutant proteins). The methods of the invention employ novel RNAi agents which selectively target the mutant allele of a gain-of-function gene (e.g. SOD1) using a sequence-specific RNA silencing mechanisms such as RNA interference (Hutvagner et al., 2002). After introduction of RNAi agent into cells, the agent binds to target site sequence in a site-specific manner (e.g., by RNAi) thereby halting expression of both forms of the target gene.

RNAi is a remarkably efficient process whereby double-stranded RNA (dsRNA) induces the sequence-specific degradation of homologous mRNA in animals and plant cells (Hutvagner and Zamore (2002), Curr. Opin. Genet. Dev., 12, 225-232; Sharp (2001), Genes Dev., 15, 485-490). In mammalian cells, RNAi can be triggered by a variety of RNAi agents including 21-nucleotide (nt) duplexes of small interfering RNA (siRNA) (Chiu et al. (2002), Mol. Cell., 10, 549-561; Elbashir et al. (2001), Nature, 411, 494-498), or by micro-RNAs (mRNA), functional small-hairpin RNA (shRNA), or other dsRNAs which are expressed in-vivo using DNA templates with RNA polymerase III promoters (Zeng et al. (2002), Mol. Cell, 9, 1327-1333; Paddison et al. (2002), Genes Dev., 16, 948-958; Lee et al. (2002), Nature Biotechnol., 20, 500-505; Paul et al. (2002), Nature Biotechnol., 20, 505-508; Tuschl, T. (2002), Nature Biotechnol., 20, 440-448; Yu et al. (2002), Proc. Natl. Acad. Sci. USA, 99(9), 6047-6052; McManus et al. (2002), RNA, 8, 842-850; Sui et al. (2002), Proc. Natl. Acad. Sci. USA, 99(6), 5515-5520.)

The molecular mechanism of RNAi is remarkably conserved among eurakaryotic organsims. The dsRNA or hairpin RNA structure of an RNAi agent is recognized and processed by Dicer, an enzyme of the RNase III family, into 21-25 nucleotide small interfering RNAs (siRNAs). The siRNAs interact with the cellular proteins Dicer and R2D2, to form a complex (RISC-loading complex or RLC) which in turn facilitates the formation of a siRNA/multi-protein complex called RISC(RNA-induced silencing complex). The RLC then interacts with additional other proteins including Ago2 to form the active RISC that contains one of the two siRNA strands termed the guide strand. The active RISC complex is capable of recognizing the target RNA via Watson-Crick base pairing with the guide strand. The RISC complex then cleaves the target RNA, which is then released, thereby regenerating a RISC complex which is free to catalyze a new cycle of target recognition and cleavage (Tomari & Zamore, 2005).

RNA intereference can also be triggered by micro RNAs (miRNAs). miRNAs are generated from long transcripts, called pri-miRNA, which are synthesized by RNA polymerase II (BRACHT et al., 2004; CAI et al., 2004; Lee et al., 2004). Pri-miRNA is processed by RNase III enzyme Drosha and its partner Pasha to form pre-miRNA, which is ~70 nt long and folds into a hairpin structure (Lee et al., 2003; Denli et al., 2004). It is then exported by Exportin 5 from the nucleus to the cytoplasm (Yi et al., 2003; BOHNSACK et al., 2004; Lund et al., 2004; Zeng & Cullen, 2004), where it is further processed by Dicer to form single stranded miRNA (Grishok et al., 2001; Hutvagner et al., 2001; Ketting et al., 2001). This processing step may be tightly coupled with loading of the miRNA into the RISC, which is then capable of either cleaving the target RNA via RNAi (if the target perfectly complements the miRNA in sequence) or mediating translational silencing of the target RNA (if the miRNA contains mismatches multiple sequences in the target RNA). This process has been mimicked by shRNAs synthesized from either Pol III or Pol II promoters (Xia et al., 2002; Shi, 2003; Zeng & Cullen, 2003; Zhou et al., 2005).

Because of its sequence specificity, RNAi has become an important therapeutic strategy. However, in certain instances, the efficacy of an RNAi agent may be sub-optimal (Khvorova et al., 2003; Hsieh et al., 2004; Reynolds et al., 2004) or its specificity may be imperfect (Jackson et al., 2003). This may be particularly problematic for the treatment of gain-of-function disorders where allele-specific RNA silencing is desired. To accomplish this, RNAi agents targeting the mutation site must be used (Ding et al., 2003; Miller et al., 2003). Consequently, due to the limited number of RNAi agents with sufficient sequence complementarity, one may be forced to select an RNAi agent with sub-optimal potency or selectivity.

Two causes for reduced efficacy of RNAi agents have been proposed: one is the inaccessibility of the target region (Brown et al., 2005; Heale et al., 2005) and the other is unfavorable strand asymmetry of the siRNA (Khvorova et al., 2003; Schwarz et al., 2003). The strand asymmetry is defined as follows: For each siRNA that is generated, only one of the two strands, the guide strand, will be loaded into the RISC and execute RNAi. The other strand, called passenger strand, will be destroyed. The thermodynamic stability of base pairing at the two ends of the siRNA predicts the likelihood of which strand will become the guide or the passenger strand. The strand with its 5' base pairing less stable then its 3' base pairing is more probable to enter RISC and vise versa. If the base pairing at the two ends has similar stability, then both strands may enter RISC with similar probabilities and mediate RNAi with similar potencies. Therefore, those siRNAs with stability of their end base pairing favoring the sense strands (as opposed to the antisense strand that is complementary to the intended target) to enter the RISC will have poor RNAi efficacy, thus having unfavorable asymmetry.

Strand asymmetry can also affect RNAi specificity. RNAi can silence unintended targets, albeit to a lesser degree than the intended one. This is called off target effects (Jackson et al., 2003). Because the critical binding energy of the RISC to the target RNA resides in the 5' half of the guide strand (Haley & Zamore, 2004), homology between this region of the guide strand and other unintended RNAs leads to off-target silencing (Jackson et al., 2003). This implies that, if both strands of the siRNA can enter the RISC, the probability of off-target silencing will increase. Accordingly, in certain aspects, the invention provides RNAi agents which are modified such that guide strand generated from said agent is preferentially incorporated into RISC. The modified RNAi agents of the invention therefore have improved efficacy and specificity in mediating RNAi.

V. RNAi Agents

The present invention features RNAi agents (e.g., siRNA and shRNAs), methods of making said RNAi agents, and methods (e.g., research and/or therapeutic methods) for using said RNAi agents (or portions thereof). The RNAi agents of the invention are duplex molecules (or molecules having duplex-like structure) comprising a sense strand and a complementary antisense strand (or portions thereof), wherein the antisense strand has sufficient complementary to a target sequence (e.g. target mRNA) to mediate RNAi. In certain embodiments, the target sequence may be an allelic polymorphism or point mutation which is unique to the mutant allele. In other embodiments, the target sequence is shared by both mutant and wild type alleles.

a) siRNA Molecules

An siRNA molecule of the invention is a duplex consisting of a sense strand and complementary antisense strand, the antisense strand having sufficient complementary to a target mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target region e.g., a gain-of-function gene target region, and the other strand is identical or substantially identical to the first strand.

Generally, siRNAs can be designed by using any method known in the art, for instance, by using the following protocol:

1. Beginning with the AUG start codon of, look for AA dinucleotide sequences; each AA and the 3' adjacent 16 or more nucleotides are potential siRNA targets. The siRNA should be specific for a target region that differs by at least one base pair between the wild type and mutant allele, e.g., a target region comprising the gain of function mutation. The first strand should be complementary to this sequence, and the other strand is identical or substantially identical to the first strand. In one embodiment, the nucleic acid molecules are selected from a region of the target allele sequence beginning at least 50 to 100 nt downstream of the start codon, e.g., of the sequence of SOD1. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to ellicit an interferon or PKR response in certain mammalian cells which may be undesirable. Preferably the RNAi agents of the invention do not ellicit a PKR response (i.e., are of a sufficiently short length). However, longer RNAi agents may be useful, for example, in cell types incapable of generating a PRK response or in situations where the PKR response has been downregulated or dampened by alternative means.

The siRNA molecules of the invention have sufficient complementarity with the target site such that the siRNA can mediate RNAi. Accordingly, in a preferred embodiment, the sense strand of the siRNA is designed have to have a sequence sufficiently identical to a portion of the target. For example, the guide strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. In another embodiment, the sense strand of the siRNA has perfect identity with the target site. In another embodiment, the sense strand has 4, 3, 2, 1, or 0 mismatched nucleotide(s) with a target region, such as a target region that differs by at least one base pair between the wild type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi.

Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut für Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

siRNA's having single nucleotide specificity can be designed as follows:

1. A target mRNA is selected (e.g., a mutant allele or mRNA) having a mismatch (e.g., a single nucleotide mismatch, for example a point mutation) as compared to a reference mRNA sequence (e.g., a wild type allele or mRNA sequence).

2. siRNAs are designed such that perfect complementarity exists between the siRNA and the target mRNA (e.g., the mutant mRNA) at the single nucleotide (e.g., the point mutation), there thus being a mismatch if the siRNA is compared (e.g., aligned) to the reference sequence (e.g., wild type allele or mRNA sequence). Preferably the siRNA is designed such that the single nucleotide (e.g., the point mutation) is at or near the intended site of cleavage. Preferably, the siRNA is designed such that single nucleotide (e.g., the point mutation) being targeted is perfectly or exactly centered in the siRNA (e.g., in the antisense strand of the siRNA). The phrase perfectly centered means that there are the same number of nucleotides flanking (i.e., 8, 9, 10, 11 or 12) the single nucleotide (e.g., the point mutation), but for any overhang, for example, a dTdT tail. For example, if a 21-nucleotide siRNA is chosen having a 2-nucleotide 3' overhang (e.g., overhang at the 3' end of the antisense strand), there are 9 nucleotides flanking the single nucleotide (e.g., point mutation). For a 22-nucleotide siRNA having a 2-nucleotide 3' overhang (e.g., overhang at the 3' end of the antisense strand) there are 9 and 10 nucleotides flanking the single nucleotide (e.g., point mutation). For a 23-nucleotide siRNA, there are 10 nucleotides flanking the single nucleotide (e.g., point mutation). For a 24-nucleotide siRNA, there are 10 and 11 nucleotides flanking the single nucleotide (e.g., point mutation). The numbers exemplified are for siRNAs having 2-nucleotide 3' overhangs but can be readily adjusted for siRNAs having longer or shorter overhangs or no overhangs. Designing the siRNA such that the single nucleotide (e.g., point mutation is off-center with respect to the siRNA may, in some instances, reduce efficiency of cleavage by the siRNA.

3. siRNAs with single nucleotide specificity are preferably designed such that base paring at the single nucleotide in the corresponding reference (e.g., wild type) sequence is disfavored. For example, designing the siRNA such that purine: purine paring exists between the siRNA and the wild type mRNA at the single nucleotide enhances single nucleotide specificity. The purine:purine paring is selected, for example, from the group G:G, A:G, G:A and A:A pairing. Moreover, purine pyrimidine pairing between the siRNA and the mutant mRNA at the single nucleotide enhances single nucleotide specificity. The purine:pyrimidine paring is selected, for example, from the group G:C, C:G, A:U, U:A, C:A, A:C, U:A and A:U pairing.

Figures 3A, 3B:
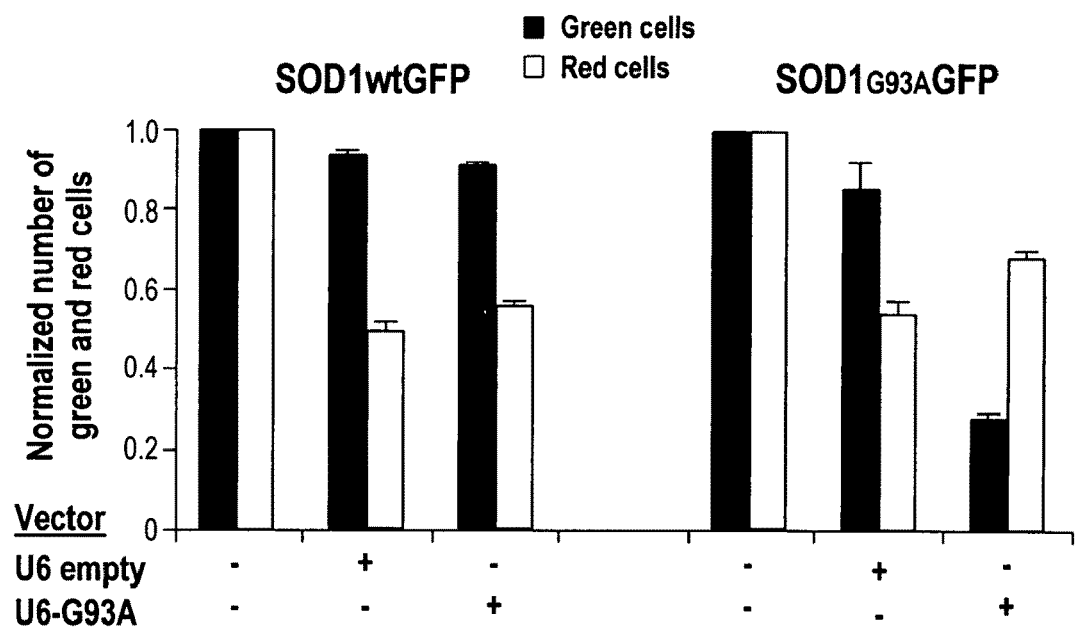
FIG. 3. Selective inhibition of mutant SOD1 G93A expression by U6-G93A vector in Hela cells. (A) Design of the G93A shRNA (SEQ ID NO: 16) and wild type SOD1 (SEQ ID NO: 15). (B) SOD1wtGFP or SOD1 G93A-GFP were cotransfected with U6-empty or U6-G93A. DsRed was cotransfected as a transfection control. Green and red fluorescent cells were quantified using FACS. Results from four experiments were averaged. Error bars represent standard deviation.

In certain embodiments, an siRNA molecule of the invention may comprise a sequence with sufficient complementarity to any of the point mutations listed in Table 1 supra. The siRNA molecules of the present invention can comprise or consists of the sequences as listed in FIG. 1A including mutant siRNA P11 (SEQ ID NO: 5, sense; SEQ ID NO: 6, anti-sense or guide), mutant siRNA P10 (SEQ ID NO: 3, sense; SEQ ID NO: 4, anti-sense or guide), mutant siRNA P9 (SEQ ID NO: 1, sense; SEQ ID NO: 2 anti-sense or guide), SOD1 wild-type target (SEQ ID NO: 7), SOD1 mutant target (SEQ ID NO: 8), wild-type siRNA P11 (SEQ ID NO: 9 sense; SEQ ID NO: 10, anti-sense or guide), wild-type siRNA P10 (SEQ ID NO: 11, sense; SEQ ID NO: 12, anti-sense or guide), wild-type siRNA P9 (SEQ ID NO: 13, sense; SEQ ID NO: 14, anti-sense or guide); FIG. 3A including G93A SOD1 siRNA (SEQ ID NO:16), and allelic variants thereof.

b) Short Hairpin RNA (shRNA) Molecules

In certain featured embodiments, the instant invention provides shRNAs capable of mediating RNAi of a gain-of-function target mRNA. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNAi agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that, has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs, or engineered precursor RNAs, of the instant invention, one portion of the duplex stem is a nucleic acid sequence that is complementary (or anti-sense) to the target mRNA. Thus, engineered RNA precursors include a duplex stem with two portions and a loop connecting the two stem portions. The two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 micleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

One strand of the stem portion of the shRNA is further sufficiently complementary (e.g., antisense) to a target RNA (e.g., mRNA) sequence to mediate degradation or cleavage of said target RNA via RNA interference (RNAi). The antisense portion can be on the 5' or 3' end of the stem. The stem portions of a shRNA are preferably about 15 to about 50 nucleotides in length. Preferably the two stem portions are about 18 or 19 to about 25, 30, 35, 37, 38, 39, or 40 or more nucleotides in length. When used in mammalian cells, the length of the stem portions should be less than about 30 nucleotides to avoid provoking non-specific responses like the interferon pathway. In non-mammalian cells, the stem can be longer than 30 nucleotides. In fact, a stem portion can include much larger sections complementary to the target mRNA (up to, and including the entire mRNA). The two portions of the duplex stem must be sufficiently complementary to hybridize to form the duplex stem. Thus, the two portions can be, but need not be, fully or perfectly complementary.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., SOD1 mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR, provided said portion is distant from the site of the gain-of-function muation. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

In certain embodiments, shRNAs of the invention include the sequences of a desired RNA silencing agent (e.g. siRNA or siRNA-like duplex). The desired RNA silencing duplex (e.g. siRNA or siRNA-like duplex), and thus both of the two stem portions in the engineered RNA precursor, are selected by methods known in the art. These include, but are not limited to, selecting an 18, 19, 20, 21 nucleotide, or longer, sequence from the target gene mRNA sequence from a region 100 to 200 or 300 nucleotides on the 3' side of the start of translation. In general, the sequence can be selected from any portion of the mRNA from the target gene, such as the 5' UTR (untranslated region), coding sequence, or 3' UTR. This sequence can optionally follow immediately after a region of the target gene containing two adjacent AA nucleotides. The last two nucleotides of the 21 or so nucleotide sequence can be selected to be UU (so that the anti-sense strand of the siRNA begins with UU). This 21 or so nucleotide sequence is used to create one portion of a duplex stem in the engineered RNA precursor. This sequence can replace a stem portion of a wild-type pre-stRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-stRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor, and to maximize the efficacy of the resulting siRNA in targeting the corresponding mRNA for translational repression or destruction by RNAi in vivo and in vitro.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor, and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. *The miRNA Registry; Griffiths-Jones S. Nuc. Acids Res.,* 2004). Over one thousand natural miRNAs have been identified to date and together they are thought to comprise ~1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (*The miRNA Registry at the Sanger Institute website; Griffiths-Jones S. Nuc. Acids Res.* 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania*, mouse, and rat as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex but only one strand is taken up by the RISC complex to direct gene silencing. Certain miRNAs, e.g. plant miRNAs, have perfect or near-perfect complementarity to their target mRNAs and, hence, direct cleavage of the target mRNAs. Other miRNAs have less than perfect complementarity to their target mRNAs and, hence, direct translational repression of the target miRNAs. The degree of complementarity between an miRNA and its target miRNA is believed to determine its mechanism of action. For example, perfect or near-perfect complementarity between a miRNA and its target mRNA is predictive of a cleavage mechanism (Yekta et al., *Science,* 2004), whereas less than perfect complementarity is predictive of a translational repression mechanism. In particular embodiments, the miRNA sequence is that of a naturally-occurring miRNA sequence, the aberrant expression or activity of which is correlated with a miRNA disorder.

Another defining feature of these engineered RNA precursors is that as a consequence of their length, sequence, and/or structure, they do not induce sequence non-specific responses, such as induction of the interferon response or apoptosis, or that they induce a lower level of such sequence non-specific responses than long, double-stranded RNA (>150 bp) that has been used to induce post-transcriptional gene silencing (e.g. RNAi). For example, the interferon response is triggered by dsRNA longer than 30 base pairs.

In one embodiment, the shRNA molecule of the invention may comprise a sequence with sufficient complementarity to any of the point mutations listed in Table 1 supra. In other embodiments the shRNA molecules of the present invention are capable of generated any of the siRNA sequences listed in FIG. 1A including mutant siRNA P11 (SEQ ID NO: 5, sense; SEQ ID NO: 6, anti-sense or guide), mutant siRNA P10 (SEQ ID NO: 3, sense; SEQ ID NO: 4, anti-sense or guide), mutant siRNA P9 (SEQ ID NO: 1, sense; SEQ ID NO: 2 anti-sense or guide), SOD1 wild-type target (SEQ ID NO: 7), SOD1 mutant target (SEQ ID NO: 8), wild-type siRNA P11 (SEQ ID NO: 9 sense; SEQ ID NO: 10, anti-sense or guide), wild-type siRNA P10 (SEQ ID NO: 11, sense; SEQ ID NO: 12, anti-sense or guide), wild-type siRNA P9 (SEQ ID NO: 13, sense; SEQ ID NO: 14, anti-sense or guide); FIG. 3A including G93A SOD1 siRNA (SEQ ID NO: 16), and allelic variants thereof.

c. Modified RNAi Agents

In certain aspects of the invention, an RNAi agent (or any portion thereof) of the invention as described supra may be modified such that the in vivo activity of the agent is improved without compromising the agent's RNA silencing activity. The modifications can, in part, serve to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) RNAi Agents with Enhanced Efficacy and Specificity

In certain embodiments, the RNAi agents of the invention have been altered to facilitate enhanced efficacy and specificity in mediating RNAi according to asymmetry design rules (see International Publication No. WO 2005/001045, US Publication No. 2005-0181382 A1). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the aymmetry of an RNAi agent is enhanced by lessening the base pair strength between the antisense strand 5' end (AS 5') and the sense strand 3' end (S 3') of the RNAi agent relative to the bond strength or base pair strength between the antisense strand 3' end (AS 3') and the sense strand 5' end (S 5') of said RNAi agent.

In one embodiment, the asymmetry of an RNAi agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNAi agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNAi agent of the invention may be enhanced such that there is at least one wobble base pair, e.g., G:U, between the 5' end of the first or antisense strand and the 3' end of the sense strand portion. In another embodiment, the asymmetry of an RNAi agent of the invention may be enhanced such that there is at least one base pair comprising a rare nucleotide, e.g., inosine (I). Preferably, the base pair is selected from the group consisting of an I:A, I:U and I:C. In yet another embodiment, the the asymmetry of an RNAi agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

In certain featured aspects, the instant invention provides modified asymmetric shRNAs which are capable of mediating enhanced efficacy and specificity of RNAi relative to an unmodified shRNA. The modified shRNA feature antisense stem portions that are least 21 nucleotides in length (e.g. about 21, 22, 23, 24, 25, 30, 35, 37, 38, 39, or 40 or more nucleotides in length) ("21 nt stem shRNA"). The asymmetric shRNA differs from an unmodifed shRNA in that a silencing duplex produced from the new shRNA has less base pair strength between the 5' end of the antisense strand or first strand and the 3' end of the sense strand or second strand than the base pair strength between the 3' end of the antisense strand or first strand and the 5' end of the sense strand or second strand.

In certain preferred embodiments, the modified 21 nt stem shRNAs of the invention have base pair strength at position 3 from the 5' end of the antisense strand. Accordingly, in one embodiment, the modified 21 nt stem shRNAs comprises a mismatched base pair at position 3 from the 5' end of the first or antisense strand and the 3' end of the sense strand portion. Preferably, the mismatched base pair is selected from the group consisting of G:A, C:A, C:U, G:G, A:A, C:C and U:U.

In another embodiment, the modified 21 nt stem shRNA comprises a wobble base pair, e.g., G:U, at position 3 from the 5' end of the first or antisense strand and the 3' end of the sense strand portion. In another embodiment, the modified 21 nt stem shRNA comprises a rare nucleotide, e.g., inosine (I) at position 3 from the 5' end of the first or antisense strand or the 3' end of the sense strand portion. Preferably, the base pair is selected from the group consisting of an I:A, I:U and I:C. In yet another embodiment, the modified 21nt stem shRNA comprises a modified nucleotide at position 3 from the 5' end of the first or antisense strand or the 3' end of the sense strand portion. In preferred embodiments, the modified nucleotide is selected from the group consisting of 2-amino-G, 2-amino-A, 2,6-diamino-G, and 2,6-diamino-A.

In certain exemplary embodiments, the modified shRNA of the invention is a modified variant of an shRNA capable of expressing siRNA P11 (SEQ ID NO: 5, sense; SEQ ID NO: 6, anti-sense or guide), mutant siRNA P10 (SEQ ID NO: 3, sense; SEQ ID NO: 4, anti-sense or guide), mutant siRNA P9 (SEQ ID NO: 1, sense; SEQ ID NO: 2 anti-sense or guide), or G93A SOD1 siRNA. Said modified shRNAs are asymmetric since the base strength at the 5' end of the antisense strand of said modified variants is less than the base pair strength at the 3' end of the sense strand of said modified variants.

2) RNAi Agents with Enhanced Stability

The RNAi agents of the present invention can be modified to improve stability in serum or in growth medium for cell cultures. In order to enhance the stability, the 3'-residues may be stabilized against degradation, e.g. they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNAi agents that include first and second strands wherein the second strand and/or first strand is modified by the substitution of internal nucleotides with modified nucleotides, such that in vivo stability is enhanced as compared to a corresponding unmodified RNAi agent. As defined herein, an "internal" nucleotide is one occurring at any position other than the 5' end or 3' end of nucleic acid molecule, polynucleotide or oligonucleoitde. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention the RNAi agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moieties of the instant invention. Additional modified residues include, deoxy-abasic, inosine, N3-methyl-uridine, N6, N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., *Nucleic Acids Res.*, (2005), 33(1): 439-447; Braasch et al. (2003) *Biochemistry* 42:7967-7975, Petersen et al. (2003) *Trends Biotechnol* 21:74-81). These molecules have 2'-O,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby preorganizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., *Science*, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNAi agent, for example, to increase half-life in the body. Thus, the invention includes RNAi agents having two complementary strands of nucleic acid, wherein the two strands are crosslinked. The invention also includes RNAi agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The RNAi agents of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the agent can be radiolabeled, e.g., using $^3H$, $^{32}P$, or other appropriate isotope.

d. Production of RNAi Agents

RNAi agents may (e.g., siRNAs) be produced enzymatically or by partial/total organic synthesis.

In one embodiment, a RNAi agent is prepared chemically. Methods of synthesizing RNA molecules are known in the art, in particular, the chemical synthesis methods as described in Verma and Eckstein (1998) *Annul Rev. Biochem.* 67:99-134.

In one embodiment, a RNAi agent is prepared enzymatically. For example, a siRNA molecule can be prepared by enzymatic processing of a long ds RNA having sufficient complementarity to the desired target mRNA. Processing of long ds RNA can be accomplished in vitro, for example, using appropriate cellular lysates and siRNA can be subsequently purified by gel electrophoresis or gel filtration. siRNA can then be denatured according to art-recognized methodologies. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

Certain RNAi agents of the invention, in particular siRNA molecules of the invention, can also be prepared in vivo by enzymatic processing of a long dsRNA molecule (>30 b.p.) which has sufficient complementarity to the desired target mRNA. Preferably, in vivo processing of the long dsRNA molecule occurs in a non-mammalian cell or a mammalian cell which is deficient in the interferon-mediated inflammatory response to dsRNA. In one embodiment, the cell capable of dsRNA enzymatic processing may be present within an organism such that dsRNA processing can be induced in vivo to trigger gene silencing of a target gene within the organism. Alternatively, the cell (i.e. a host cell) containing endogenous machinery for dsRNA processing (e.g. DICER) or transformed with heterologous genes to enable dsRNA processing) be cultured and induced to process dsRNA in vitro. RNA silencing agents may then be purified from the host cell following dsRNA processing for administration to an organism containing the target gene to be silenced.

In another embodiment, RNAi are synthesized directly either in vivo, in situ, or in vitro. An endogenous RNA polymerase in the cell may mediate transcription of the RNAi agent in vivo or in situ, or a cloned RNA polymerase can be used for transcription of the RNAi agent in vivo or in vitro. For transcription from a transgene in vivo or an expression construct, a regulatory region (e.g., promoter, enhancer, silencer, splice donor and acceptor, polyadenylation) may be used to transcribe the RNAi agent (e.g. siRNA or or shRNA). Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses a RNAi agent (e.g. siRNA or or shRNA) from a recombinant construct may be produced by introducing the construct into a zygote, an embryonic stem cell, or another multipotent cell derived from the appropriate organism.

e. Detection of RNAi Agents

In certain aspects of the invention, it may be important to detect the generation or expression of RNAi agents (e.g. siRNAs and shRNAs), target mRNAs and/or the gene products encoded by said target RNAs. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, Genomics 4: 560-569 (1989); Landren et al., Proc. Natl. Acad. Sci. 87: 8923-8927 (1990); Barany, F., Proc. Natl. Acad. Sci. 88: 189-193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., PCR Methods and Applications 1: 5-16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

Detection oligonucleotide probes range in size between 10-1,000 bases. In order to obtain the required target discrimination using the detection oligonucleotide probes, the hybridization reactions are generally run between 20°-60° C., and most preferably between 30°-50° C. As known to those skilled in the art, optimal discrimination between perfect and mismatched duplexes is obtained by manipulating the temperature and/or salt concentrations or inclusion of formamide in the stringency washes.

Detection of proteins may be carried out using specific antibodies, e.g., monoclonal or polyclonal antibodies, or fragments thereof.

Preferred detection reagents are labeled, e.g., fluorescents, coloro-metrically or radio-iso-typically labeled to facilitate visualization and/or quantitation.

IV. Constructs and Host Cells

Another aspect of the invention pertains to constructs, preferably expression constructs, encoding an RNAi agent (e.g. an siRNA or shRNA) or a portion thereof. Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include facilitate one or both strands of the RNAi agent. Expression constructs expressing both strands can also include loop structures linking both strands, or each strand can be separately transcribed from separate promoters within the same construct. Each strand can also be transcribed from a separate expression construct. (Tuschl (2002), supra).

In one embodiment, the construct is a transgene. In another embodiment, the construct is a vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The vectors described herein can be introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by reference. See, also, Ausubel et al., Current Protocols in Molecular Biology, John Wiley and Sons, Baltimore, Md. (1989); Hitt et al, "Construction and propagation of human adenovirus vectors," in Cell Biology: A Laboratory Handbook, Ed. J. E. Celis., Academic Press. 2.sup.nd Edition, Volume 1, pp: 500-512, 1998; Hitt et al, "Techniques for human adenovirus vector construction and characterization," in Methods in Molecular Genetics, Ed. K. W. Adolph, Academic Press, Orlando, Fla., Volume 7B, pp: 12-30, 1995; Hitt, et al., "Construction and propagation of human adenovirus vectors," in Cell Biology: A Laboratory Handbook," Ed. J. E. Celis. Academic Press. pp: 479-490, 1994, also hereby incorporated by reference. The methods include, for example, stable or transient transfection, lipofection (e.g., cationic liposome transfection), electroporation and infection with recombinant viral vectors.

In certain embodiments, the expression constructs of the invention comprise a nucleic acid (DNA or RNA) operably linked to one or more regulatory sequences (e.g., promoter sequences). The phrase "operably linked" is intended to mean that the nucleotide sequence of interest (e.g., a sequence encoding an RNAi agent (e.g. shRNA)) is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences).

Other elements included in the design of a particular expression vector can depend on such factors as the choice of the host cell to be transformed, the level of expression of protein desired, etc. The expression vectors of the invention can be introduced into host cells to thereby produce miRNA, proteins or peptides, including fusion proteins or peptides, encoded by nucleic acids as described herein.

Constructs can be constructed by recombinant DNA technology methods known in the art. The nucleic acid sequences encoding the RNAi agents can be prepared using known techniques. For example, two synthetic DNA oligonucleotides can be synthesized to create a novel gene encoding an entire RNAi agent. The DNA oligonucleotides, which will pair, leaving appropriate 'sticky ends' for cloning, can be inserted into a restriction site in a plasmid that contains a promoter sequence (e.g., a Pol II or a Pol III promoter) and appropriate terminator sequences 3' to the engineered RNA precursor sequences (e.g., a cleavage and polyadenylation signal sequence from SV40 or a Pol III terminator sequence).

The constructs described herein can be introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by reference. See, also, Ausubel et al., Current Protocols in Molecular Biology, John Wiley and Sons, Baltimore, Md. (1989); Hitt et al, "Construction and propagation of human adenovirus vectors," in Cell Biology: A Laboratory Handbook, Ed. J. E. Celis., Academic Press. 2.sup.nd Edition, Volume 1, pp: 500-512, 1998; Hitt et al, "Techniques for human adenovirus vector construction and characterization," in Methods in Molecular Genetics, Ed. K. W. Adolph, Academic Press, Orlando, Fla., Volume 7B, pp: 12-30, 1995; Hitt, et al., "Construction and propagation of human adenovirus vectors," in Cell Biology: A Laboratory Handbook," Ed. J. E. Celis. Academic Press. pp: 479-490, 1994, also hereby incorporated by reference. The methods include, for example, stable or transient transfection, lipofection (e.g., cationic liposome transfection), electroporation and infection with recombinant viral vectors.

a. RNAi Agent Expression Constructs

In certain embodiments, the invention provides DNA expression constructs which facilitate the expression of the RNAi agents (e.g. siRNAs and shRNAs) of the invention.

To achieve intracellular concentrations of the RNAi agent sufficient to suppress expression of target mRNAs, one can use, for example, such expression constructs can include one or more inducible promoters, RNA Pol III promoter systems such as U6 snRNA promoters or H1 RNA polymerase III promoters, or other promoters known in the art. The use of such a construct to transfect target cells in vitro or in vivo will result in the transcription of sufficient amounts of the RNAi agent that can target a corresponding mRNA sequence for cleavage (i.e. RNAi). For example, a vector can be introduced in vivo such that it is taken up by a cell and directs the transcription of an RNAi agent. Such a vector can remain episomal or become chromosomally integrated, as long as it can be transcribed to produce the desired stRNA precursor.

In certain embodiments, the expression constructs of the invention encode an siRNA. The expression constructs preferably encode or both strands of an siRNA. Expression constructs expressing both strands can also include loop structures linking both strands. Alternatively, each strand can be separately transcribed from separate promoters within the same construct. Each strand can also be transcribed from a separate expression construct. (Tuschl (2002), supra).

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides. Brummelkamp et al., Science 296:550-553 (2002); Lee et al, (2002). supra; Miyagishi and Taira, Nature Biotechnol. 20:497-500 (2002); Paddison et al. (2002), supra; Paul (2002), supra; Sui (2002) supra; Yu et al. (2002), supra. shRNAs so generated are processed under appropriate conditions (e.g., in an appropriate in vitro reaction or in a cell) by RNAi machinery (i.e., Dicer and/or RISC complexes) to generate siRNAs. shRNAs can be synthesized exogenously or can be transcribed in vivo from an RNA polymerase (e.g., a Pol II or Pol III polymerase), thus permitting the construction of continuous cell lines or transgenic animals in which the desired gene silencing is stable and heritable.

A single construct may contain multiple sequences coding for RNAi agents (e.g. siRNAs), such as multiple regions of the gene encoding mutant SOD1, targeting the same gene or multiple genes, and can be driven, for example, by separate PolIII promoter sites.

Viral-mediated delivery mechanisms can also be used to induce specific silencing of targeted genes through expression of RNAi agents, for example, by generating recombinant adenoviruses expression RNAi agents under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the RNAi agent results in in-vivo reduction of target gene expression. Id. In an animal model, whole-embryo electroporation can efficiently deliver synthetic nucleic acids into post-implantation mouse embryos (Calegari et al., Proc. Natl. Acad. Sci. USA 99(22): 14236-40 (2002)). In adult mice, efficient delivery of nucleic acid agents can be accomplished by "high-pressure" delivery technique, a rapid injection (within 5 seconds) of a large volume of nucleic acid agent containing solution into animal via the tail vein (Liu (1999), supra; McCaffrey (2002), supra; Lewis, Nature Genetics 32:107-108 (2002)).

b. Host Cells

Another aspect of the invention pertains to host cells into which a host construct of the invention has been introduced, i.e., a "recombinant host cell." It is understood that the term "recombinant host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell, although eukaryotic cells are preferred. Exemplary eukaryotic cells include mammalian cells (such as Chinese hamster ovary cells (CHO) or COS cells). Other suitable host cells are known to those skilled in the art.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders, such as disease and disorders associated with mutant or aberrant gene expression, gain-of-function mutants and neurological diseases and disorders.

The present invention is also not limited to the use of the cell types and cell lines used herein. Cells from different tissues or different species (human, mouse, etc.) are also useful in the present invention.

V. Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the miRNA to be targeted by the siRNA generated from the engineered RNA precursor will be depleted from the cell or organism, leading to a decrease in the concentration of the protein encoded by that miRNA in the cell or organism.

VI. Methods of Introducing Nucleic Acids, Vectors, and Host Cells

Physical methods of introducing nucleic acids include injection of a solution containing the nucleic acid, bombardment by particles covered by the nucleic acid, soaking the cell or organism in a solution of the nucleic acid, or electroporation of cell membranes in the presence of the nucleic acid. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. The nucleic acid may be introduced along with other components that perform one or more of the following activities: enhance nucleic acid uptake by the cell or other-wise increase inhibition of the target gene.

Nucleic acids may be directly introduced into the cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of RNAi agent material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNAi agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

Synthetic siRNAs can be delivered into cells by methods known in the art, including cationic liposome transfection and electroporation. However, these exogenous siRNA generally show short term persistence of the silencing effect (4~5 days in cultured cells), which may be beneficial in only certain embodiments. To obtain longer term suppression of the target genes (i.e., mutant genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expressing T7 RNA polymerase (Jacque (2002), supra). A single construct may contain multiple sequences coding for siRNAs, such as multiple regions of the gene encoding mutant SOD1, targeting the same gene or multiple genes, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific miRNA targets in mammalian cells (Zeng (2002), supra). When expressed by DNA vectors containing polymerase III promoters, micro-RNA designed hairpins can silence gene expression (McManus (2002), supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in-vivo reduction of target gene expression. Id. In an animal model, whole-embryo electroporation can efficiently deliver synthetic siRNA into post-implantation mouse embryos (Calegari et al., Proc. Natl. Acad. Sci. USA 99(22):14236-40 (2002)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, Nature Genetics 32:107-108 (2002)). Nanoparticles and liposomes can also be used to deliver siRNA into animals.

The nucleic acid compositions of the invention include both unmodified siRNAs and modified siRNAs as known in the art, such as crosslinked siRNA derivatives or derivatives having non nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that miRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis)

generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25): 14428-33. Epub 2001 Nov. 27).

VII. Pharmaceutical Compositions and Methods of Administration

The RNAi agents of the invention can be incorporated into pharmaceutical compositions. Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The compounds can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a nucleic acid molecule (i.e., an effective dosage) depends on the nucleic acid selected. For instance, if a plasmid encoding shRNA is selected, single dose amounts in the range of approximately 1:g to 1000 mg may be administered; in some embodiments, 10, 30, 100 or 1000:g may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), supra.

The pharmaceutical compositions can be included in a container, pack, or dispenser together with instructions for administration.

VIII. Methods of Treatment

The present invention provides for both prophylactic and therapeutic methods of treating a subject at risk of (or susceptible to) a disease or disorder caused, in whole or in part, by a gain-of-function mutant protein. In one embodiment, the disease or disorder is a dominant gain-or-function disease. In a preferred embodiment, the disease or disorder is a disorder associated with the an alteration of SOD1 gene, specifically a point mutation in the SOD1 mutant allele, leading to a defect in SOD 1 gene (structure or function) or SOD1 protein (structure or function or expression), such that clinical manifestations include those seen in ALS disease patients.

"Treatment", or "treating" as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., a RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for a mutation within the gene, such that sequence specific interference with the gene is achieved. These methods can be performed in vitro (e.g., by culturing the cell with the agent) or, alternatively, in vivo (e.g., by administering the agent to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

EXAMPLES

The following materials, methods, and examples are illustrative only and not intended to be limiting.

Materials And Methods
 RNA and DNA Constructs
 Single strand RNAs (e.g. see FIG. 1A) were purchased from Dharmacon Research, deprotected according to manufacturer's instructions, and annealed as described (Nykanen et al., 2001).

Figures 6, 7:
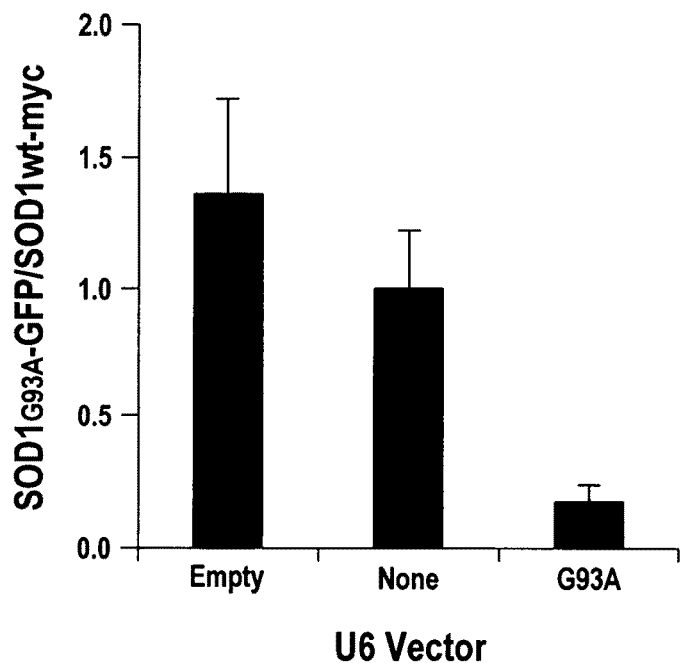
FIG. 6. Selective inhibition of mutant SOD1 expression by U6-G93A vector in vivo. (A) SOD1 G93A-GFP were co-transfected with a C-terminal myc tagged wild-type human SOD1 in mice using the hydrodynamic transfection method. The relative band intensities on SDA-PAGE were quantified. The ratio of SOD1 G93A-GFP to wild type SOD1myc are shown. Eight animals were used in each group. The U6-G93A group is significantly different from the other two groups ($p<0.05$).
FIG. 7 is the Genbank entry for human SOD-1 protein, Accession No. NP_000445, showing the deduced amino acid sequence of wild-type SOD-1 (SEQ ID NO:18).

To create wild type and mutant SOD1-GFP fusion proteins, SOD1wt (Genbank Accession No. NP_000445; FIG. 7; SEQ ID NO: 18), SOD1 G85R and SOD1 G93A (SEQ ID NO:16) cDNAs were PCR cloned between the PmlI and PstI sites of pCMV/myc/mito/GFP (Invitrogen). This cloning step deleted the mitochondrial targeting sequence.

To create myc tagged wild type SOD1, SOD1wt cDNA (SEQ ID NO:17) was PCR cloned between the PstI and XhoI sites of pCMV/myc/mito/GFP. The mitochondrial targeting sequence was then deleted by digestion with BssHII and PmlI and blunt ligation.

To construct the shRNA vectors, the two strands of synthetic DNA oligonucletides were annealed, and subcloned into a RNA polymerase III promoter (U6) driven vector using the restriction sites Pme I and Pst I (Sui et al. 2002). The DNA strands contained 19 or 21 nt sense and antisense strands (that matches the target sequences) linked by a nine-nucleotide loop (UUCAAGAGA). The sense strand terminates with 5 consecutive Thymidines (TTTTT).

All constructs were verified by sequencing. DsRed (pDsRed2-$C_1$) was purchased from Clontech (Palo Alto, Calif.). U6-G93A was constructed as described (Sui et al., 2002). The 3'-block siRNA was synthesized by standard techniques.

In-Vitro RNAi Assay

Five hundred and sixty nucleotide human SOD1 target RNAs containing either wild-type or mutant SOD1 coding sequence were prepared as described previously (Zamore et al., 2000). Target cleavage was determined by incubating a ~5 nM concentration of the 5', $^{32}$P-cap-radiolabeled target RNA with 25-100 nM siRNA in a standard in-vitro RNAi reaction containing *Drosophila* embryo lysate (Tuschl et al., 1999; Zamore et al., 2000).

Cell Culture and Transfection

Hela cells were cultured in DMEM and N2A cells in DMED and Opti-MEM (1:1), both supplemented with 10% fetal bovine serum (FBS), 100 units $ml^{-1}$ penicillin, and 100 ug $ml^{-1}$ streptomycin. Twenty-four hours before transfection, cells (70-90% confluency) detached by trituration, transfered to 6-well plates and cultured in fresh medium without antibiotics. Transfection was carried out using Lipofectamine® 2000 (Invitrogen) according to manufacturer's instructions. The amount of the constructs used in transfections are 4 μg each of mutant or wild type SOD1-GFP and DsRed plasmids, $4 \times 10^{-11}$ or $4 \times 10^{-12}$ mole siRNAs, and 20 or 8 μg U6-G93A.

In-Vivo Transfection

Twenty-four mice 6-8 weeks old were divided into three groups. The first group received no shRNA vector, the second group received 20 μg empty vector and the third group received 20 μg U6-hpRNA vector against SOD1 G93A (SEQ ID NO:16). All groups received both 20 μg of myc tagged human wild type SOD1 (SEQ ID NO: 7) and 20 μg GFP tagged SOD1. The vectors were diluted in Ringer's solution so that the total volume equaled 2.5 ml per mouse. Mice were anaesthetized with avertin (240 mg/kg) and the vectors were injected into the tail vein using a 26-gauge needle in less than 10 seconds. Forty-eight hours following injection animals were perfused with 5 ml PBS in order to remove blood from the liver. Livers were dissected and quickly frozen on dry ice. Samples were placed in 25 mM PBS buffer (pH 7.2) containing 1% SDS, 1 mM DTT, 1 mM phenylmethylsufonyl fluoride (PMSF), and protease inhibitor cocktail (Sigma, diluted 1:100) and homogenized using a hand held polytrone (Proscientific).

Western Blot Analysis

In Examples I-IX, protein concentrations were determined using a BCA protein assay kit (Pierce; Rockville Ill.). Twenty five μg Hela cell proteins or 100 μg liver proteins were separated on a 15% SDS-PAGE gel and transferred onto Genescreen Plus membrane (Perkin Elmer). Rabbit anti-SOD1 (Biodesign) or Sheep anti-SOD1 was the primary and HRP-labeled goat anti-rabbit IgG (Amersham) or donkey anti-sheep IgG was the secondary antibodies. The protein bands were visualized using SuperSignal kit (Pierce) and Kodak Digital Image Station 440CF. The intensity of the bands was quantified using Kodak 1D software.

In Examples X-XI

Two nM siRNAs were transfected into HEK 293 cells in 96-well plates on day 1. Cells were detached by pipetting gently and transferred into a 24-well plate on day 2. The second transfection was carried out on day 3 and cells were eventually harvested on day 4. Proteins were extracted by homogenization in a 25 mM phosphate buffer (PH 7.2) containing 1% SDS, 1 mM DTT, 1 mM PMSF, and Protease inhibitor cocktail (Sigma) and the concentrations were determined using the BCA assay (Pierce). Fiften ug protein was loaded onto a 15% SDS-PAGE gel. After the transfer onto a Genescreen Plus membrane (Perkin Elmer), SOD1 was detected using rabbit anti-SOD1 (Biodesign) as the primary antibody and HRP-labeled goat anti-rabbit IgG (Amersham) as the secondary antibody. As controls the membrane was stripped using a buffer containing 0.1 M Glycine (PH 3.0) and reprobed using an antibody against GAPDH. The protein bands were visualized by Chemiluminescent SuperSignal kit (Pierce) and quantified using the Kodak Digital Image System 440CF.

Dual Luciferase Assay

A modified dual luciferase system (Promega) was used to quantify RNAi efficiency in cell culture. To generate a specific luciferase report target for this study, two restriction sites (Nde I and Spe I) were engineered into the 3' UTR of the firefly luciferase vector (pGL2 control vector, Promega). A 39 nt fragment of human Cu Zn superoxide dismutase (sod1) gene (sense strand 5'-AGGCATGTTGGAGACT-TGGGCAATGTGA-CTGCTGACAAA-3'(SEQ ID NO: 80), antisense strand 5'-TTTGTCAGCAGTCACATTGC-CCAAGTCT-CCAACATGCCT-3') (SEQ ID NO: 81) was synthesized, annealed and cloned into 3' UTR region of firefly luciferase vector using the Nde I and Spe I sites. This firefly luciferase vector was co-transfected with Renilla luciferase vector (pRL-TK, Promega) plus siRNA or the shRNA-synthesizing vectors into the HEK293 cells in 96 well plates using Lipofectamine 2000 reagent (Invitrogen). Twenty four hours after the transfection, cells were lysed with 20 ul Passive Lysis Buffer (Promega). Ten ul lysate from each well was transfer into a well in a Microlite strip (Thermo labsystems) and measured with a Veritas microplate luminometer (Turner Biosystem). The luminescence intensity ratio (Firefly/Renilla luciferase) was used for measuring the RNAi efficacy.

Northern Blot

One ug of each of the shRNAs was transfected into HEK293 cells in 6-well plates. Cells were harvested 24 hours post-transfection and the total RNA was extracted with Tri Reagent (Molecular Research Center). Ten ug of total RNA was loaded onto a mini 15% denaturing polyacrylamide gel. The separated RNAs were transferred onto a BrightStar-Plus nylon membrane (Ambion) and cross-linked with UV. $^{32}$P labeled sense or antisense 21 nt synthetic RNAs were used as probes for detecting its complementary RNA strands. The radioactive RNA bands were read with Fuji Phosphor Imaging system FLA-5000 (Fuji Medical Systems).

Example I

Examples I-VIII show that siRNAs were designed to have single-nucleotide selectivity by first testing siRNA activity in a cell-free RNAi reaction containing *Drosophila* embryo lysate, then analyzing active, single-nucleotide-selective siRNAs in cultured mammalian cells. Results showed that both 21 nucleotide siRNAs and shRNA can be designed that selectively inhibit the expression of the mutant (SEQ ID NO:8), but not of the wild type SOD1 (SEQ ID NO:7), even though the two mRNAs differ by only a single nucleotide and are present in the same cells. Thus, RNAi is useful as a therapy for diseases caused by dominant, gain-of-function type of mutations, inter alia.

Example II siRNA Duplexes can Discriminate for Mutant SOD1

Two sets of three siRNAs, each targeting either wild type or mutant SOD1 mRNA (FIG. 1A; SEQ ID NO:8) were designed to test whether mismatches at or near the site of target cleavage would disrupt the required A-form *Helix*. An allele of SOD1 in which guanosine 256 (G256; relative to the start of translation, e.g., of Genbank Accession No. K00056:) is mutated to cytosine, generating a glycine-to-arginine mutation (G85R) was selected. The mutated nucleotide was positioned near the predicted site of SOD1 mRNA cleavage, i.e., position 9 (P9), 10 (P10), or 11 (P11) relative to the 5' end of the antisense strand of the siRNA (FIG. 1A). This predicted site of SOD1 mRNA cleavage would place a mismatch between the siRNA and its non-cognate target RNA in or near the active site of the RNAi endonuclease. These siRNAs were tested in an established *Drosophila* embryo lysate reaction that recapitulates RNA in-vitro (Zamore et al., 2000; Tuschl et al., 1999). As expected, each of the six siRNAs cleaved the corresponding target RNA, although with dramatically different efficacy. For example, the P11 mutant and wild type siRNAs (SEQ ID NO: 6, 10) did not cut their respective target RNA efficiently. On the other hand, the P10 mutant siRNA (SEQ ID NO:4) efficiently cleaved the mutant target RNA. The destruction of the full-length mutant SOD1 target mRNA was accompanied by a corresponding accumulation of 5' cleavage product of approximately 288 nucleotides, a result indicative of RNAi, rather than non-specific degradation of the target mRNA. In the absence of siRNA or in the presence of an siRNA against the luciferase, the mutant SOD1 target RNA (SEQ ID NO:8) was stable in the *Drosophila* embryo lysate (data not shown). Data for both the destruction of target RNA and the accumulation of 5' cleavage product fit well to a single exponential equation, indicating that the reaction follows pseudo first-order kinetics (FIG. 1B).

Example III siRNA Duplexes can Discriminate for Wild-Type SOD1

To determine the specificity of the six siRNAs, each siRNA corresponding to the mutant SOD1 sequence (SEQ ID NO:8) was tested for its ability to cleave the wild-type SOD1RNA (SEQ ID NO:7), and each wild-type siRNA was tested for its ability to cleave mutant RNA. Some, but not all of the siRNA duplexes effectively discriminated between the target to which they are matched completely and the target with which they have a single nucleotide mismatch (FIG. 1A). For example, P11 of both mutant and wild type siRNAs (SEQ ID NO:6,10) did not trigger effective cleavage of either the perfectly matched or mismatched target RNA (FIG. 1A). Thus, these siRNA sequences are inherently poor triggers of RNAi. On the other hand, P9 (SEQ ID NO: 14) and P10 wild type (SEQ ID NO:12) siRNAs triggered rapid cleavage of their corresponding the wild type target, but also produced significant cleavage of the mutant RNA (FIG. 1A). These siRNAs are good triggers of RNAi, but show poor selectivity. P10 mutant siRNA (SEQ ID NO:4) showed efficient and robust discrimination between mutant and wild type SOD1RNAs (SEQ ID NO:7,8), cleaving the mutant RNA far more efficiently than the wild type (FIG. 1A). Most importantly, P10 mutant siRNA (SEQ ID NO:4) showed virtually complete discrimination between mutant and wild type SOD1 mRNA targets (FIG. 1A). This P10 mutant siRNA mediated efficient cleavage of the mutant SOD1 target but nearly no cleavage of the wild-type SOD1 mRNA (FIG. 1B), suggesting that this siRNA is ideal for therapeutic application.

Example IV

Selective Inhibition of Mutant SOD1 G85R Expression in Hela Cells

To test whether cell-free reactions accurately predict siRNA efficiently and selectivity in mammalian cells, plasmid constructs that expressed the wild type or the mutant SOD1 G85R with GFP fused to their carboxyl termini were made. Each construct was transfected into Hela cells with a dsRed-expressing vector as a transfection control. The expression of either mutant or wild-type SOD1 (SEQ ID NO:7,8) was monitored by fluorescence-activated cell sorting (FACS) quantification of the green and red cells. Transfection of P9, P10 and P11 siRNAs with their corresponding mutant or wild type targets suppressed gene expression, although with different efficiencies and selectivites (FIG. 2). In contrast, co-transfection with a siRNA complementary to firefly luciferase did not suppress either the mutant or the wild type SOD1 expression (FIG. 2). All siRNAs did not suppress the mRNA targets with a single nucleotide mismatch except the siRNA p10 against wild type, which suppressed both the wild type and the mutant SOD1 expression effectively (FIG. 2). This result in general agrees with the in-vitro data (FIG. 1) and indicated that some, but not all siRNAs can efficiently discriminate the mRNA targets with a single-nucleotide difference.

Example V

Selective Inhibition of Mutant SOD1 G93A Expression by U6-G93A Vector in Hela Cells Recently it has been shown that shRNA can trigger RNAi in-vivo. To test whether shRNA against mutant SOD1 can selectively block the expression of the mutant but not the wild-type SOD1 expression, a plasmid was constructed that synthesized an shRNA homologous to another disease-causing mutant SOD1 G93A (nucleotide change from G to C at nucleotide position 281; placing a G:G mismatch at selective sites between the shRNA and wild-type SOD1; SEQ ID NO:16) under the control of a RNA polymerase III (U6) promoter (Sui et al., 2002). Results showed that when co-transfected with either wild-type or mutant SOD1-GFP plasmids, this construct can be used to trigger single-nucleotide selective RNAi of mutant SOD1 in cultured cells (FIG. 3).

Example VI

Figure 4A:
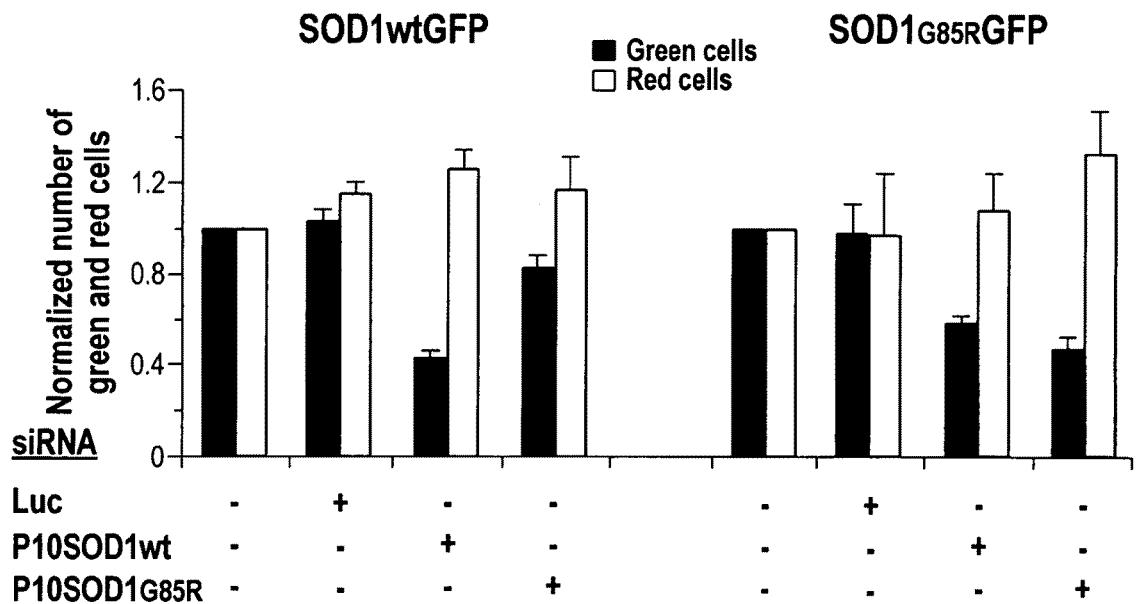
FIG. 4. Selective inhibition of mutant SOD1 expression by siRNA and U6-G93A vector in neuroblastoma N2a cells. (A) siRNA against G85R (n=4), (B) U6-G93A vector (n=3). Error bars represent standard deviation.

Selective Inhibition of Mutant SOD1 Expression by siRNA and U6-G93A Vector In-Vivo To test whether mutant selective inhibition can be achieved in neuronal cells, wild-type and mutant SOD1-GFP constructs were co-transfected the with either siRNA P10 against SOD1 G85R or shRNA-synthesizing vector against SOD G93A (SEQ ID NO:16) into a neuroblastoma cell line N2a. Similar to Hela cells, both synthetic siRNA and shRNA constructs directed the selective inhibition of mutant SOD1 expression in N2a cells (FIG. 4A, B).

Example VII

Selective Inhibition of Mutant SOD1 G85R In-Vivo

Figure 5:
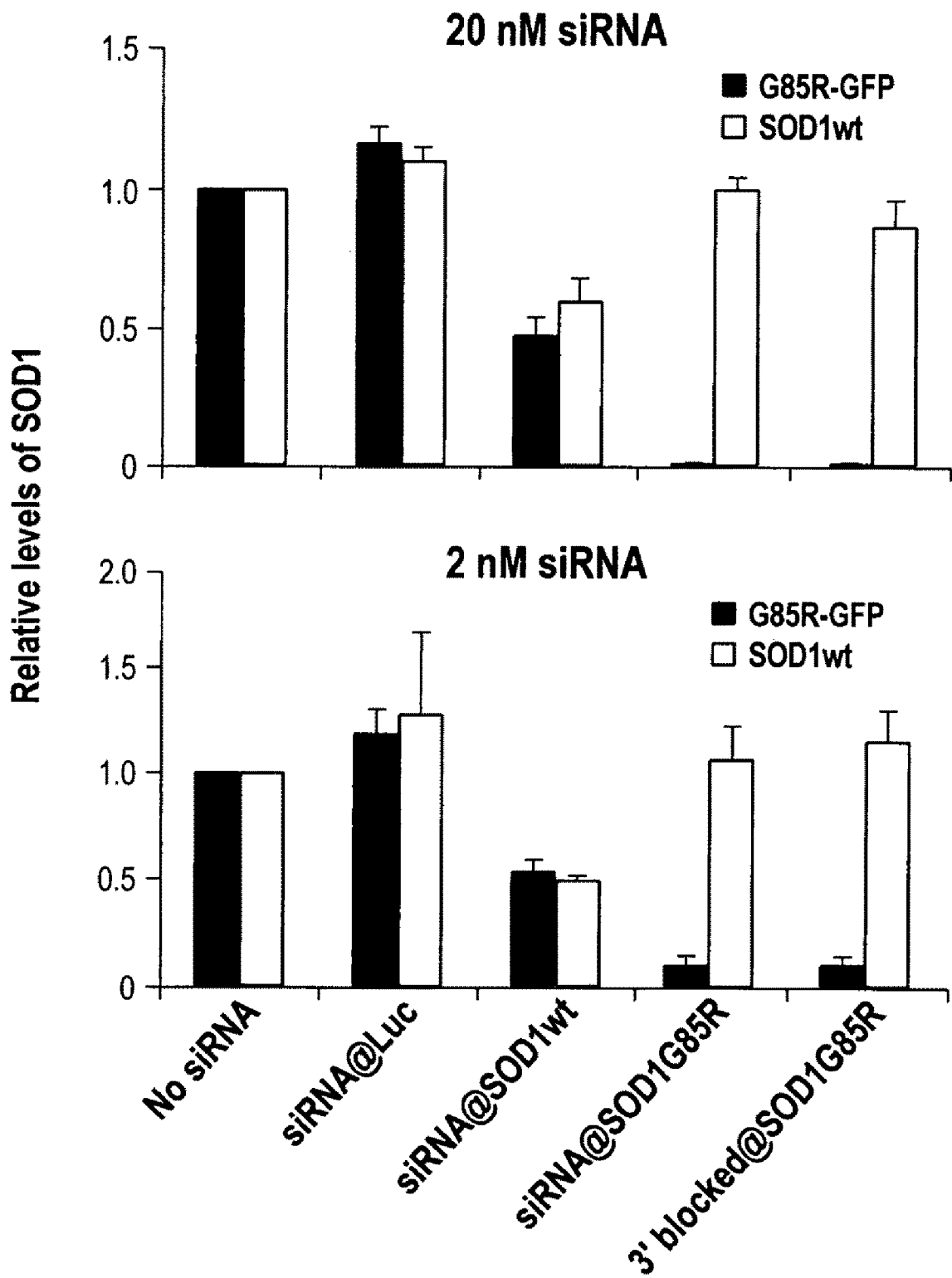
FIG. 5. Selective inhibition of mutant SOD1 G85R but not the wild type SOD1 expression by siRNA in the same cells. (A) Relative levels of SOD1 measured from protein blots of transfected Hela cells detecting mutant SOD1 G85R-GFP (average of 4 transfections). Error bars are standard error.

To determine whether single-nucleotide selective siRNA can discriminate between the mutant and the wild-type SOD1 when both mRNA's are present in the same cell, Hela cells were transfected with P10 siRNAs and mutant SOD1 G85R-GFP. Immunoblotting with anti-SOD1 antibodies were performed, which allowed for the detection of both the transfected fusion SOD1-GFP and the endogenous wild type human SOD1. The near 50% inhibition of the endogenous wild-type SOD1 expression reflected the transfection efficiency, which was ~50%. In contrast to the P10 wild-type siRNA, at two different doses, P10 siRNA against the mutant inhibited expression of the mutant, but had no effect on the expression of endogenous wild-type SOD1 (FIG. 5).

Example VIII

Selective Inhibition of Mutant SOD1 Expression by U6-G93A Vector In-Vivo

To test whether selective inhibition can occur in-vivo, transfection of SOD1 reporters and shRNA plasmid into mice using a hydrodynamic transfection protocol was performed. The mutant SOD1 G93A-GFP plasmid and a wild type human SOD1 tagged with myc (which allowed better separation of the transfected human SOD1 from the endogenous mouse SOD1 on gels) were co-transfected with either U6 empty vector or U6-G93A vector. Liver expression of SOD1 G93A-GFP and SOD1myc was examined by Western blot. Results showed that only co-transfection with U6-G93A selectively decreased G93A expression (FIG. 6).

Example IX shRNA Suppression of Mutant SOD1 In-Vivo Using Transgenic Mice

To determine whether shRNA against mutant SOD1 can suppress mutant SOD1 expression in vivo, transgenic mice expressing shRNAs against SOD1 G93A under the control of a RNA polymerase III (Pol III) promoter U6 (U6-G93A mice) were made in a C57BL/6J and SJL hybrid background.

The plasmid synthesizing shRNA homologous mutant SOD1 93A (shG93A) under the control of mouse U6 promoter was made according to the published protocol (Sui et al., 2002 *Proc Natl Acad Sci USA* 99:5515-5520). To make the mice, the transgene was linearized by digestion using Kpn I and Sac I, purified and injected into fertilized mouse eggs at University of Massachusetts Medical School (UMMS) transgenic core.

To screen for U6-G93A transgenic mice, PCR primers that selectively amplify the transgene sequence were designed and used to identify the transgenic mice. A total of seven founders (F0) were identified. These founders have been crossed with mice transgenic for mutant SOD1$^{G93A}$ in an FVB background.

F1 mice were analyzed for transgene copy numbers using Southern blot as described previously (Xu et al., 1993 *Cell* 73:23-33). Tail DNA was digested with Bam H1, which generated a transgene fragment of 388 nucleotides. Because the endogenous mouse U6 promoter has only one BamHI site, the BamHI digestion produced a larger fragment from the endogenous mouse U6 gene. $^{32}$P-labeled RNA oligonucleotide probes complementary to the U6 promoter region were used for hybridization. The U6 region was used as the target because the endogenous mouse U6 band can be detected together with the transgene on the same blot, therefore, the endogenous band can be used as the reference for quantifying the transgene copy number.

Figure 4B:
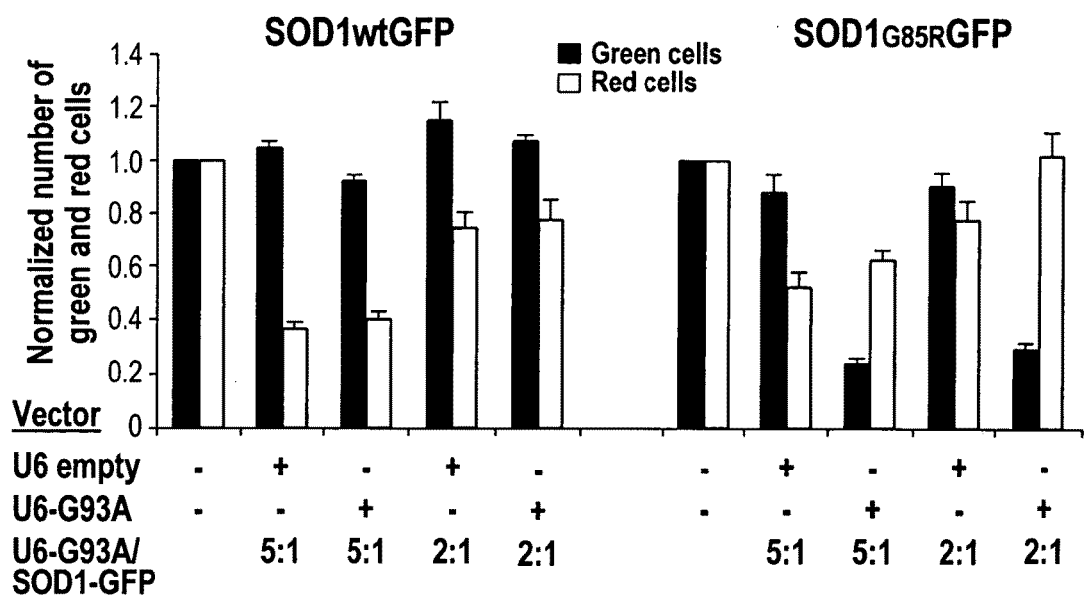

The U6-G93A shRNA construct was expressed in cells from the double transgenic mice as measured using Northern blots. The U6-G93A shRNA construct was found to silence expression of mutant SOD1$^{G93A}$ in the double transgenic mice (expressing the U6-G93A shRNA construct and mutant SOD1$^{G93A}$) as measured using Western blots Discussion of Results Examples I-VIII The possibility of using RNAi to selectively silence a dominant mutant ALS gene was investigated. Using multiple siRNAs matching either wild-type or mutant SOD1, results showed that siRNAs against mutant SOD1G85R cleave the mutant, but not the wild-type SOD1 RNA efficiently in-vitro (FIG. 1). In addition, these siRNAs selectively inhibited the mutant but not the wild-type SOD1 protein expression in mammalian cell (FIG. 2), even when both the mutant and the wild type proteins were present in the same cells (FIG. 4). A vector expressing a hairpin that is processed in-vivo into an siRNA also selectively inhibited mutant but not wild-type SOD1 expression in mouse liver (FIGS. 3, 4, 6). These results demonstrated that selective inhibition of a dominant mutant allele can be achieved using RNAi and optimal siRNA and shRNA sequences can be identified by a pre-clinical screen in-vitro or in-vivo.

Although SOD1 single nucleotide discrimination can be achieved in mammalian cells, this discrimination is not guaranteed. Some siRNAs are capable of discrimination between alleles that differ at a single nucleotide while others cannot. Results point to two different types of deficiencies for siRNA designed to target mutant, disease causing alleles. First, while siRNAs perfectly matched to their target can cleave their target and inhibit the protein expression from the target gene, all siRNAs do not silence with the same efficiency. For example, among the siRNAs against the wild type, P9 and P10 cleaved their target more efficiently than P11 in-vitro (FIG. 1). P10 also inhibited target gene expression most efficiently in mammalian cells (FIG. 2). Similarly, among the siRNAs against the mutant SOD1 G85R, P9 and P10 cleaved the mutant RNA more efficiently than P11 (FIG. 1). P10 was also the most efficient in inhibiting the mutant SOD1 expression in mammalian cells (FIG. 2). It is intriguing that a single nucleotide shift of the siRNA sequence against the target results in such a significant change in silencing efficiency.

Second, differences in selectivity between the perfectly matched target RNA and the RNA bearing a single nucleotide mismatch were observed among six siRNAs used. For example, wild-type P10 siRNA conferred poor selectivity. Wild-type P10 cleaved both wild type and mutant SOD1 RNA in the cell-free assay and inhibited the expression of both alleles in mammalian cells with high efficiency (FIGS. 1, 2, 4, 5). On the other hand, P10 siRNA directed against mutant SOD1 conferred the highest selectivity. It cleaved the mutant SOD1 RNA and inhibited the mutant SOD1 expression in cell-free assay and inhibited mutant but not wild-type SOD1 expression in mammalian cells (FIGS. 1-6).

An explanation for the different selectivity between the mutant and the wild type P10 siRNAs is the following: the mismatch between the mutant P10 siRNA and the wild type SOD1 mRNA created a G:G clash, while the mismatch between the wild type P10 siRNA and the mutant G85R mRNA resulted in a C:C clash (see FIG. 1A). Thus, in designing an siRNA that selectively acts on one allele of a given sequence, the following are considered. Without wishing to be bound by theory, a purine:purine mismatch disrupts the A-form helix that is required between the antisense strand of the siRNA and its mRNA target (Chiu et al., 2002). In contrast, a pyrimidine:pyrimidine mismatch may more readily be accommodated within an A-form helix. Thus, the G:G clash between the siRNA and the wild-type target RNA discriminates against the wild-type target, producing greater selectivity for the mutant target. Noticeably, the siRNA hairpin vector against G93A, which showed a good selectivity for mutant SOD1, also created a G:G clash with the wild-type SOD1 mRNA. These results suggested that purine:purine mismatches confer greater selectivity than pyrimidine:pyrimidine mismatches. In addition to designing siRNAs for use in the present method that contain pyrimidine:pyrimidine mismatches, the siRNAs are designed using methods known in the art.

Example X

Figure 10:
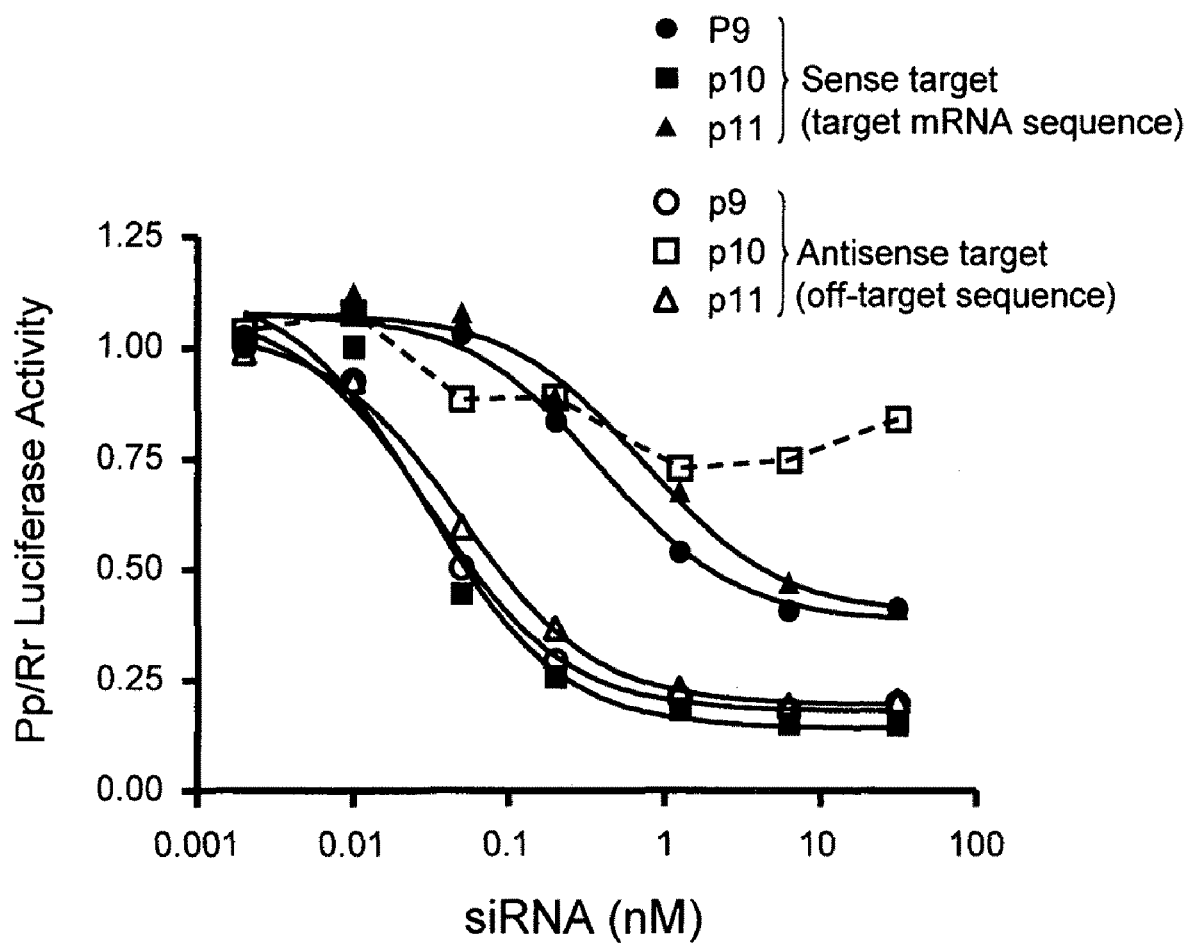
FIG. 10 depicts asymmetric siRNAs (P9, P10 and P11) capable of targeting the same region of human SOD1 mRNA. The sequence of P11 is shown in FIG. 11A. P9 and P10 target sod1 sequences that are shifted toward the 5' end of the sod1 mRNA by 2 and 1 nucleotide(s) respectively. Even though the three siRNAs target sequences only 1nt shifted from each other, their strand preference are very different, with P9 and P11 favoring the anti-sense strand target and P10 favoring the sense strand target.

Designed Asymmetry Switches Strand Preference and Enhances the RNAi Efficacy of the Desired Strand Natural siRNAs may have unfavorable strand asymmetry. For example, of the three anti-SOD1 siRNAs described in Examples I-IX, one siRNA (P10) silenced its intended sod1 mRNA target sequence, a sod1 mRNA sequence (referred to herein is as the "sense strand target" or "coding strand target" (ss-target)), better than an its reverse complement or "off-target" sequence (referred to herein as the "antisense strand target" or "non-coding strand target" (as-target)). The other two siRNAs (P9, P11) actually silenced the as-target better than the ss-target (FIG. 10). As expected, the siRNAs that preferentially silenced the as-target silenced the ss-target relatively inefficiently, with the IC50 against the ss-target at 0.39 nM for the P9 and 0.75 nM for the P11, compared with those against the as-target at 0.03 nM and 0.05 nM, respectively. Thus, P9 and P11 were poor candidates of natural siRNAs.

Figure 11:
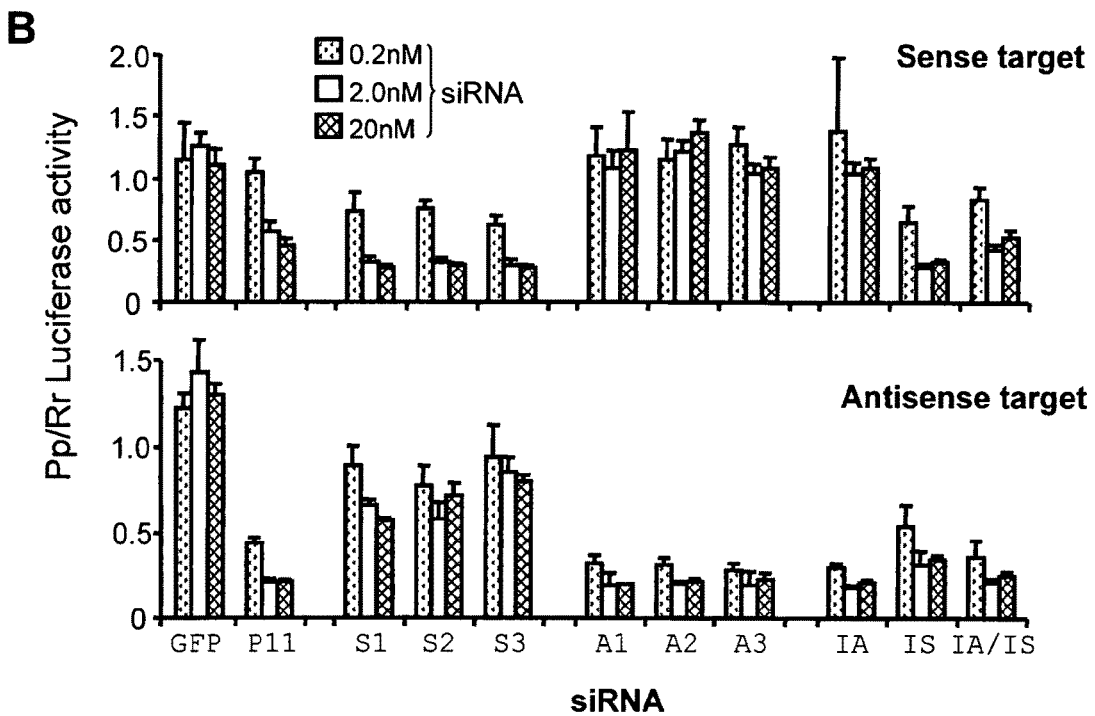
FIG. 11 depicts asymmetric siRNA which have been engineered for natural strand preference by placing mismatches at the 5' end of the siRNA strand which is desired to be the preferred strand to go into the RISC.

To determine whether the inefficient siRNAs can be converted to efficient ones, we took one of the inefficient siRNAs, the P11 (FIG. 11A), as a test case. Based on the asymmetry rule, we weakened the base pairing at the 5' of the anti-sense strand of the siRNA (as-siRNA) by placing mismatches or the A:U pair at that end (FIG. 11A, S1-S3). Although P11 naturally favored the as-target (FIG. 11B, see P11), weakening the base pairing at the 5' of the as-siRNA converted it to favoring the sense target (FIG. 11B, S1-S3). In contrast, weakening base pairing at the 5' of the sense strand of the siRNA (ss-siRNA) accentuated the preference for silencing the as-target as compared to unmodified P11 siRNA (FIG. 11B, A1-A3). Furthermore, weakening base pairing by replacing GC with I:C at one end or the other similarly switched strand preferences (FIG. 11B, IA, IS). If G:C at both ends was converted to I:C, the strand preference returned to the pattern of the P11 (FIG. 11B, IS/IA). These changes are consistent with the predictions by the asymmetry rule.

Figure 12:
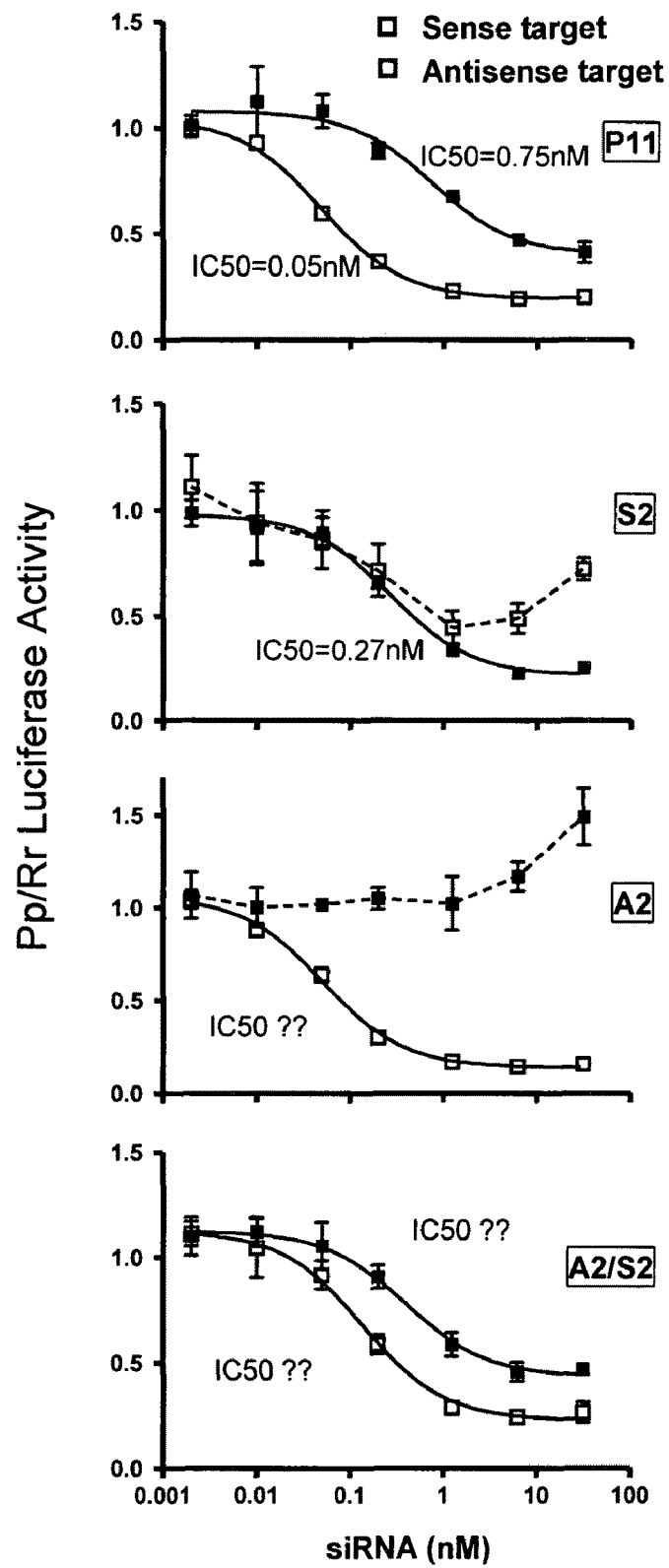
FIG. 12 depicts aymmetric siRNA designs that improve the RNAi efficacy of the desired strand and worsen the RNAi efficacy of the undesired strand. The sequences of P11, S2 and A2 siRNAs are shown in FIG. 11A. The siRNA A2/S2 were generated by annealing the sense strand of A2 siRNA with the antisense strand of the S2 siRNA (see FIG. 11A).

To characterize the effects of the designed asymmetry quantitatively, we transfected the ss- and as-targets with different doses of siRNAs. The original P11 silenced the as-target maximally by 81%, with the IC50 at 0.05 nM. In contrast, it silenced the sense target maximally by only 61%, with IC50 at 0.75 nM (FIG. 12, P11). By weakening the base pairing at the 5' of the as-siRNA, the siRNA silenced the as-target maximally by only 56%, with an atypical dose response curve that reached the maximal silencing at 2 nM of siRNA and poorer silencing at the higher concentrations; in contrast, this siRNA silenced the sense target maximally by 78%, with the IC50 at 0.27 nM (FIG. 12, S2), a significant improvement compared with the original P11. Thus, compared with the original P11, weakening the base pairing at the 5' of the as-siRNA reduced the RNAi efficiency against the as-target and enhanced the RNAi efficiency against the ss-target. Conversely, weakening the base pairing at the other end produced the reverse effect, enhancing the maximal silencing of the as-target while preventing silencing of the sense target completely (FIG. 12, A2). If base pairing was weakened at both ends of the siRNA, the silencing pattern of the target reverted to the original P11 (FIG. 12, S2/A2). These results confirm the predictions by the asymmetry rule and indicate that asymmetry rule can be applied to increase the repertoire of siRNA targeting sites.

Example XI

Application of Asymmetry Rule to shRNAs Enhances the Strand Specificity and Efficacy Thereof To find the optimal strategy to incorporate the asymmetry rule in the design of an shRNA, we first tested shRNAs with 19 nucleotide stems ("19 nt stem shRNAs") and further comprising a mismatch placed within the first four nucleotides of either end of shRNA stem (FIG. 13A). The shRNA with two strands of the stem perfectly matched demonstrated symmetrical silencing efficacy (FIG. 13B, P11-19). Mismatches at positions 1 and 2 from the 5' end of the sense strand (FIG. 13A, A1-19, A2-19) enhanced the silencing of the as-target while mildly weakening the silencing of the ss-target (FIG. 13B, A1-19, A2-19), as predicted by the asymmetry rule. However, mismatches at positions 3 and 4 from the 5' end of the sense strand (FIG. 13A, A3-19, A4-19) enhanced silencing efficacy against the ss-target but did not change the silencing efficacy against the as-target (FIG. 13B, A3-19, A4-19), suggesting that mismatches in these two positions of 19 nt-stem shRNAs do not follow the asymmetry rule.

Mismatch at position 1 from the 5' end of the as-shRNA stem (FIG. 13A, S1-19) also does not conform to the asymmetry rule. While it did not change the silencing efficiency of the as-target, it actually compromised silencing of the ss-target (FIG. 13B, S1-19)—contrary to what was expected by the asymmetry rule. Mismatches at positions 2 and 3 from the 5' of the as shRNA stem (FIG. 13A, S2-19, S3-19) did not enhance the silencing efficacy against the ss-target, but diminished the silencing of as-target (FIG. 13B, S2-19, S3-19). Mismatches at position 4 from the 5' of the as shRNA stem (FIG. 13A, S4-19) did not affect the silencing efficacy against either ss- or as-target (FIG. 13B, S4-19). Overall, most of the mismatches created at either end of the stem poorly conform to the asymmetry rule in their silencing efficacy.

shRNAs mimic pre-miRNAs in structure, processing and function. Most pre-miRNAs have stems longer than 21-nt in length (Griffiths-Jones, 2004). From these stems miRNA duplexes, including those that are asymmetric, are produced (Kim, 2005). Thus, shRNAs with stems 21-nt or longer might be processed better after incorporation of the asymmetry rule. To test this we designed shRNAs with 21-nt stems and with weakened base pairing (mismatches) at each of the positions 1-4 at both ends of the stem (FIG. 13A). We cotransfected each of these plasmids that synthesize the shRNAs with the plasmids that synthesize the sense or antisense targets and determined their RNAi efficacy.

The P11 shRNA had similar strand preference as the P11 siRNA. It silenced the as-target better than the ss-target (FIG. 14B, P11-21). When the mismatched base pairs were placed at the 5' end of the ss-shRNA, the strand preference to the as-target was accentuated at positions 1 and 2 (FIG. 14B, A1-21, A2-21), but reduced at position 3 and 4 (FIG. 14B, A3-21, A4-21). Conversely, when the mismatches were placed at the 5' of the as-shRNA at positions 1-4, the strand preference is reversed from the original P11-21—the shRNA silenced the ss-target better than the as-target (FIG. 14B, S1-21 to S4-21), although at the position 4, the strand preference diminished. We conclude that the best weak base pairing position for generating favorable strand preference is at the position 2 of the sense strand (A2-favoring antisense target) and the position 3 of the antisense strand (S3-favoring sense target), because mismatches at these positions generated largest strand asymmetry.

Figure 15:
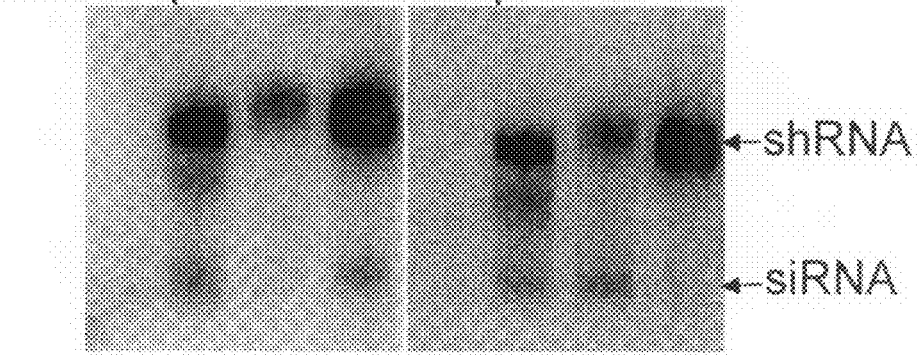
FIG. 15 depicts data which demonstrates that the designed asymmetric shRNAs were processed as predicted by the asymmetry rule.

Previous studies in *drosophila* embryo extracts demonstrated that the fate of the two strands in siRNA is different during RISC assembly. R2D2 acts as a sensor for the asymmetry of the siRNA duplexes and binds to the thermodynamically stable end. Dicer then binds the other end that is less stable in its base pairing (Tomari et al., 2004). This results in the favored strand being incorporated into RISC and mediating RNAi, and the opposite strand being destroyed (Schwarz et al., 2003). The switch of the RNAi efficacy of the two strands depending on the strand asymmetry in the shRNAs suggested that this might also be the case in mammalian cells (FIG. 15A). To experimentally test this we performed a Northern blot using RNA extracted from the cells transfected with the shRNA-expressing vectors. We detected the shRNAs produced by all three constructs (FIG. 15B). The shRNAs were processed to siRNA. Both strands of siRNA from the P11 construct were detected. However, only the favored strand was detected from the S2 and A3 constructs (FIG. 15B). This result is consistent with those from the *drosophila* embryo extracts (Tomari et al., 2004). It is not yet clear what the sensor for shRNA asymmetry is. However, a recent experiment demonstrated that in *Drosophila*, Loquacious (Loqs) binds to miRNA and this binding is required for Dicer-1 processing of miRNAs (Forstemann et al., 2005). Loqs is a dsRNA binding protein similar to R2D2, and thus, could act as an asymmetry sensor for miRNAs or shRNAs.

Can the strategy of placing mismatches at position 2 of the sense strand or position 3 of the antisense strand of shRNA generate favorable strand preference in other shRNAs? To answer this question, we constructed three additional shRNAs and placed mismatches at the A2 and S3 positions (FIG. 16A). The original shRNAs silenced the sense strand slightly better than the antisense strand (FIG. 16B, Or). Placing a mismatch at the position A2 increased the silencing efficacy against the as-target and decreased the silencing efficacy against the ss-target for all three shRNAs, although the quantities of this change were small for two of the shRNAs, shsod1a and shsod1c (FIG. 16B, A2). On the other hand, placing a mismatch at S3 increased the silencing efficacy against the ss-target and decreased the silencing efficacy against the as-target (FIG. 16B, S3). Based on these results, we conclude that mismatch placed at S3 position most consistently enhanced the strand specificity and RNAi efficacy.

REFERENCES

1. Amarzguioui, M., Holen, T., Babaie, E., and Prydz, H. (2003). Tolerance for mutations and chemical modifications in a siRNA. Nucleic Acids Res 31, 589-595.
2. Behndig, A., Karlsson, K., Reaume, A. G., Sentman, M. L. & Marklund, S. L. In vitro photochemical cataract in mice lacking copper-zinc superoxide dismutase. Free Radic Biol Med 31, 738-44. (2001).
3. Bohnsack, M. T., Czaplinski, K., Gorlich, D. (2004). Exportin 5 is a RanGTP-dependent dsRNA-binding protein that mediates nuclear export of pre-miRNAs. RNA 10:185-191.
3. Boutla, A., Delidakis, C., Livadaras, I., Tsagris, M. & Tabler, M. Short 5'-phosphorylated double-stranded RNAs induce RNA interference in Drosophila. Curr Biol 11, 1776-80. (2001).
4. Bracht, J., et al., (2004). Trans-splicing and polyadenylation of let-7 microRNA primary transcripts. RNA 10:1586-1594.
5. Brown, K M, Chu C-y, Rana T M. (2005). Target accessibility dictates the potency of human RISC. 12:469-470
6. Brummelkamp, T. R., Bernards, R. & Agami, R. A system for stable expression of short interfering RNAs in mammalian cells. Science 296, 550-3. (2002).
7. Brummelkamp, T., Bernards, R. & Agami, R. Stable suppression of tumorigenicity by virus-mediated RNA interference. Cancer Cell 2, 243. (2002).
8. Cai, X, et al., (2004). Human microRNAs are processed from capped, polyadenylated transcripts that can also function as mRNAs. RNA 10:1957-1966
9. Caplen, N. J., Parrish, S., Imani, F., Fire, A. & Morgan, R. A. Specific inhibition of gene expression by small double-stranded RNAs in invertebrate and vertebrate systems. Proc Natl Acad Sci USA 98, 9742-7. (2001).
10. Caplen, N. J. et al. Rescue of polyglutamine-mediated cytotoxicity by double-stranded RNA-mediated RNA interference. Hum Mol Genet 11, 175-84. (2002).
11. Chalk, A. M., et al., (2005). siRNAdb: a database of siRNA sequences. Nucl Acids Res 33:D131-134.
12. Chiu, Y.-L. & Rana, T. M. RNAi in human cells: basic structural and functional features of small interfering RNA. Molecular Cell 10, 549-561 (2002).
13. Cleveland, D. W. & Rothstein, J. D. From Charcot to Lou Gehrig: deciphering selective motor neuron death in ALS. Nat Rev Neurosci 2, 806-19. (2001).
14. Denli A M, Tops B B J, Plasterk R H A, Ketting R F, Hannon G J. (2004). Processing of primary microRNAs by the Microprocessor complex. 432:231-235.
15. Devroe, E. & Silver, P. A. Retrovirus-delivered siRNA. BMC Biotechnol 2, 15. (2002).
16. Ding H, Schwarz D S, Keene A, Affar el B, Fenton L, Xia X, Shi Y, Zamore P D, Xu Z. (2003). Selective silencing by RNAi of a dominant allele that causes amyotrophic lateral sclerosis. Aging Cell 2:209-217.
17. Elbashir, S. M., Lendeckel, W. & Tuschl, T. RNA interference is mediated by 21- and 22-nucleotide RNAs. Genes Dev 15, 188-200. (2001).
18. Elbashir, S. M. et al. Duplexes of 21-nucleotide RNAs mediate RNA interference in cultured mammalian cells. Nature 411, 494-8. (2001).
19. Elbashir, S. M., Martinez, J., Patkaniowska, A., Lendeckel, W. & Tuschl, T. Functional anatomy of siRNAs for mediating efficient RNAi in Drosophila melanogaster embryo lysate. Embo J 20, 6877-88. (2001).
20. Flood, D. G. et al. Hindlimb motor neurons require Cu/Zn superoxide dismutase for maintenance of neuromuscular junctions. Am J Pathol 155, 663-72. (1999).
21. Forstemann K, Tomari Y, Du T, Vagin V V, Denli A M, Bratu D P, Klattenhoff C, Theurkauf W E, Zamore P D. (2005). Normal microRNA Maturation and Germ-Line Stem Cell Maintenance Requires Loquacious, a Double-Stranded RNA-Binding Domain Protein. PLoS Biology 3.
22. Griffiths-Jones S. (2004). The microRNA Registry. Nucl Acids Res 32:D109-111.
23. Grishok A, Pasquinelli A E, Conte D, Li N, Parrish S, Ha I, Baillie D L, Fire A, Ruvkun G, Mello C C. (2001). Genes and Mechanisms Related to RNA Interference Regulate Expression of the Small Temporal RNAs that Control C. elegans Developmental Timing. Cell 106:23-34.
24. Haley B, Zamore P D. (2004). Kinetic analysis of the RNAi enzyme complex. 11:599-606.
25. Hamilton, A. J. & Baulcombe, D. C. A species of small antisense RNA in posttranscriptional gene silencing in plants. Science 286, 950-2. (1999).
26. Hammond, S. M., Bernstein, E., Beach, D. & Hannon, G. J. An RNA-directed nuclease mediates post-transcriptional gene silencing in Drosophila cells. Nature 404, 293-6. (2000).
27. Hannon, G. J. RNA interference. Nature 418, 244-51. (2002).
28. Heale B S E, Soifer H S, Bowers C, Rossi J J. (2005). siRNA target site secondary structure predictions using local stable substructures. Nucl Acids Res 33:e30-.
29. Hohjoh H. (2004). Enhancement of RNAi activity by improved siRNA duplexes. FEBS Lett 557:193-198.
30. Hsieh A C, Bo R, Manola J, Vazquez F, Bare O, Khvorova A, Scaringe S, Sellers W R. (2004). A library of siRNA duplexes targeting the phosphoinositide 3-kinase pathway: determinants of gene silencing for use in cell-based screens. Nucl Acids Res 32:893-901.
31. Hutvagner G, McLachlan J, Pasquinelli A E, Balint E, Tuschl T, Zamore P D. (2001). A Cellular Function for the RNA-Interference Enzyme Dicer in the Maturation of the let-7 Small Temporal RNA. Science 293:834-838
32. Hutvagner, G. & Zamore, P. D. RNAi: nature abhors a double-strand. Curr Opin Genet Dev 12, 225-32. (2002).
33. Jackson A L, Bartz S R, Schelter J, Kobayashi S V, Burchard J, Mao M, Li B, Cavet G, Linsley P S. (2003). Expression profiling reveals off-target gene regulation by RNAi. Nat Biotechnol 21:635-637.
34. Jacque, J. M., Triques, K. & Stevenson, M. Modulation of HIV-1 replication by RNA interference. Nature 418, 435-8. (2002).
35. Kawase, M. et al. Exacerbation of delayed cell injury after transient global ischemia in mutant mice with CuZn superoxide dismutase deficiency. Stroke 30, 1962-8. (1999).
36. Ketting R F, Fischer S E J, Bernstein E, Sijen T, Hannon G J, Plasterk R H A. (2001). Dicer functions in RNA interference and in synthesis of small RNA involved in developmental timing in C. elegans. Genes Dev 15:2654-2659.
37. Khvorova A, Reynolds A, Jayasena S D. (2003). Functional siRNAs and miRNAs exhibit strand bias. Cell 115:209-216.

38. Kim V N. (2005). MicroRNA BIOGENESIS: COORDINATED CROPPING AND DICING. *Nat Rev Mol Cell Biol* 6:376-385.
39. Kondo, T. et al. Reduction of CuZn-Superoxide Dismutase Activity Exacerbates Neuronal Cell Injury and Edema Formation after Transient Focal Cerebral Ischemia. Journal of Neuroscience 17, 4180-9 (1997).
40. Lee, N. S. et al. Expression of small interfering RNAs targeted against HIV-1 rev transcripts in human cells. Nat Biotechnol 20, 500-5. (2002).
41. Lee Y, Ahn C, Han J, Choi H, Kim J, Yim J, Lee J, Provost P, Radmark O, Kim S, Kim V N. (2003). The nuclear RNase III Drosha initiates microRNA processing. *Nature* 425:415-419.
42. Lee Y, Kim M, Han J, Yeom K H, Lee S, Baek S H, Kim V N. (2004). MicroRNA genes are transcribed by RNA polymerase II. *EMBO J* 23:4051-4060. Epub 2004 September 4016.
43. Lipardi, C., Wei, Q. & Paterson, B. M. RNAi as random degradative PCR: siRNA primers convert miRNA into dsRNAs that are degraded to generate new siRNAs. Cell 107, 297-307. (2001).
44. Lund E, Guttinger S, Calado A, Dahlberg J E, Kutay U. (2004). Nuclear Export of MicroRNA Precursors. *Science* 303:95-98.
45. Matz, P. G., Copin, J. C. & Chan, P. H. Cell death after exposure to subarachnoid hemolysate correlates inversely with expression of CuZn-superoxide dismutase. Stroke 31, 2450-9. (2000).
46. Matzuk, M. M., Dionne, L., Guo, Q., Kumar, T. R. & Lebovitz, R. M. Ovarian function in superoxide dismutase 1 and 2 knockout mice. Endocrinology 139, 4008-11. (1998).
47. McFadden, S. L., Ding, D. & Salvi, R. Anatomical, metabolic and genetic aspects of age-related hearing loss in mice. Audiology 40, 313-21. (2001).
48. McManus, M. T. & Sharp, P. A. Gene silencing in mammals by small interfering RNAs. Nat Rev Genet 3, 737-47. (2002).
49. McManus, M. T., Petersen, C. P., Haines, B. B., Chen, J. & Sharp, P. A. Gene silencing using micro-RNA designed hairpins. Rna 8, 842-50. (2002).
50. Miller V M, Xia H, Marrs G L, Gouvion C M, Lee G, Davidson B L, Paulson H L. (2003). Allele-specific silencing of dominant disease genes. *PNAS* 100:7195-7200.
51. Miyagishi, M. & Taira, K. U6 promoter-driven siRNAs with four uridine 3' overhangs efficiently suppress targeted gene expression in mammalian cells. Nat Biotechnol 20, 497-500. (2002).
52. Nykanen, A., Haley, B. & Zamore, P. D. ATP requirements and small interfering RNA structure in the RNA interference pathway. Cell 107, 309-21. (2001).
53. Paddison, P. J., Caudy, A. A., Bernstein, E., Hannon, G. J. & Conklin, D. S. Short hairpin RNAs (shRNAs) induce sequence-specific silencing in mammalian cells. Genes Dev 16, 948-58. (2002).
54. Paul, C. P., Good, P. D., Winer, I. & Engelke, D. R. Effective expression of small interfering RNA in human cells. Nat Biotechnol 20, 505-8. (2002).
55. Reynolds A, Leake D, Boese Q, Scaringe S, Marshall W S, Khvorova A. (2004). Rational siRNA design for RNA interference. *Nat Biotechnol* 22:326-330.
56. Schwarz D S, Hutvagner G, Du T, Xu Z, Aronin N, Zamore P D. (2003). Asymmetry in the assembly of the RNAi enzyme complex. *Cell* 115:199-208.
57. Schwarz, D. S., Hutvagner, G., Haley, B. & Zamore, P. D. Evidence that siRNAs function as guides, not primers, in the *Drosophila* and human RNAi pathways. Molecular Cell 10, 537-548 (2002).
58. Shefner, J. M. et al. Mice lacking cytosolic copper/zinc superoxide dismutase display a distinctive motor axonopathy. Neurology 53, 1239-46. (1999).
59. Shi Y. (2003). Mammalian RNAi for the masses. *Trends Genet* 19:9-12.
60. Sui, G. et al. A DNA vector-based RNAi technology to suppress gene expression in mammalian cells. Proc Natl Acad Sci USA 99, 5515-20. (2002).
61. Taylor, J. P., Hardy, J. & Fischbeck, K. H. Toxic proteins in neurodegenerative disease. Science 296, 1991-5. (2002).
62. Tomari Y, Matranga C, Haley B, Martinez N, Zamore P D. (2004). A protein sensor for siRNA asymmetry. *Science in press.*
63 Tomari Y, Zamore P D. (2005). Perspective: machines for RNAi. *Genes Dev* 19:517-529.
64. Tuschl, T., Zamore, P. D., Lehmann, R., Bartel, D. P. & Sharp, P. A. Targeted mRNA degradation by double-stranded RNA in vitro. Genes Dev 13, 3191-7. (1999).
65. Xia, H., Mao, Q., Paulson, H. L. & Davidson, B. L. siRNA-mediated gene silencing in vitro and in vivo. Nat Biotechnol 20, 1006-10. (2002).
66. Xu, P., Vernooy, S. Y., Guo, M., and Hay, B. A. (2003). The *Drosophila* MicroRNA Mir-14 Suppresses Cell Death and Is Required for Normal Fat Metabolism. Curr Biol 13, 790-795.
67. Yi R, Qin Y, Macara I G, Cullen B R. (2003). Exportin-5 mediates the nuclear export of pre-microRNAs and short hairpin RNAs. *Genes Dev* 17:3011-3016.
68. Yu, J. Y., DeRuiter, S. L. & Turner, D. L. RNA interference by expression of short-interfering RNAs and hairpin RNAs in mammalian cells. Proc Natl Acad Sci USA 99, 6047-52. (2002).
69. Zamore, P. D., Tuschl, T., Sharp, P. A. & Bartel, D. P. RNAi: double-stranded RNA directs the ATP-dependent cleavage of mRNA at 21 to 23 nucleotide intervals. Cell 101, 25-33. (2000).
70. Zeng, Y., Wagner, E. J. & Cullen, B. R. Both natural and designed micro RNAs can inhibit the expression of cognate mRNAs when expressed in human cells. Mol Cell 9, 1327-33. (2002).
71. Zeng Y, Cullen B R. (2003). Sequence requirements for micro RNA processing and function in human cells. *Rna* 9:112-123.
72. Zeng Y, Cullen B R. (2004). Structural requirements for pre-microRNA binding and nuclear export by Exportin 5. *Nucl Acids Res* 32:4776-4785.
73. Zhou H, Xia X G, Xu Z. (2005). An RNA polymerase II construct synthesizes short-hairpin RNA with a quantitative indicator and mediates highly efficient RNAi. *Nucl Acids Res* 33:e62-.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

In addition, the contents of all patent publications discussed supra are incorporated in their entirety by this reference.

What is claimed is:

1. A method of enhancing the ability of a shRNA to mediate RNA interference (RNAi) comprising (i) providing a shRNA comprising a duplex stem comprising an antisense stem portion having a length of 21 nucleotides and a sense stem portion, wherein said shRNA is targeted to a gain-of-function mutant allele, and (ii) enhancing the asymmetry of said stem, such that the ability of the shRNA to mediate RNAi is enhanced, wherein the asymmetry is enhanced by lessening the base pair strength between base pairs at the 5' end of the antisense strand stem portion and corresponding base pairs in the 3' end of the sense stem portion, wherein the base pair strength is less due to introduction of a single mismatched base pair between the 5' end of the antisense stem portion and the 3' end of the sense stem portion at position 3 from the 5' end of the antisense strand portion.

2. The method of claim 1, wherein the allele is correlated with a disorder associated with a dominant gain of function mutation.

3. The method of claim 2, wherein the disorder is selected from the group of amyotrophic lateral sclerosis, Huntington's disease, Alzheimer's disease, and Parkinson's disease.

4. The method of claim 3, wherein the disorder is amyotrophic lateral sclerosis.

5. The method of claim 4, wherein the allele is SOD1.

6. The method of claim 1, wherein the allele comprises a point mutation.

7. The method of claim 6, wherein the point mutation is a guanine: cytosine mutation.

8. The method of claim 6, wherein the allele is SOD1.

9. The method of claim 8, wherein the mutation is G256C.

10. The method of claim 8, wherein the mutation is G281C.

* * * * *

UNITED STATES PATENT AND TRADEMARK OFFICE
CERTIFICATE OF CORRECTION

| | | |
|---|---|---|
| PATENT NO. | : 7,892,793 B2 | Page 1 of 1 |
| APPLICATION NO. | : 11/241873 | |
| DATED | : February 22, 2011 | |
| INVENTOR(S) | : Zuoshang Xu | |

It is certified that error appears in the above-identified patent and that said Letters Patent is hereby corrected as shown below:

Please replace the paragraph at column 1, lines 3-10 with the following paragraph:

Statement as to Federally Sponsored Research

--This invention was made with government support under grant nos. GM062862 and GM053874 awarded by the National Institutes of Health, as well as grant nos. NS035750 and NS041739 awarded by the National Institute of Neurological Disorders and Stroke [NINDS]. The government has certain rights in the invention.--

Signed and Sealed this
Seventeenth Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,892,793 B2 | Page 1 of 1 |
| APPLICATION NO. | : 11/241873 | |
| DATED | : February 22, 2011 | |
| INVENTOR(S) | : Xu | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 345 days.

Signed and Sealed this

Twenty-eighth Day of June, 2011

David J. Kappos
*Director of the United States Patent and Trademark Office*

SEQUENCE LISTING

<160> NUMBER OF SEQ ID NOS: 81

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
uggagacuug cgcaaugugt t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
cacauugcgc aagucuccat t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
ggagacuugc gcaaugugat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
ucacauugcg caagucucct t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
-continued

<400> SEQUENCE: 5
gagacuugcg caaugugact t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
gucacauugc gcaagucuct t                                              21

<210> SEQ ID NO 7
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gagaggcaug uuggagacuu gggcaaugug acugcugaca aagauggu                 48

<210> SEQ ID NO 8
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gagaggcaug uuggagacuu gcgcaaugug acugcugaca aagauggu                 48

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
gagacuuggg caaugugact t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
gucacauugc ccaagucuct t                                              21
```

```
<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
ggagacuugg gcaaugugat t                                            21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
ucacauugcc caagucucct t                                            21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
uggagacuug gcaaugugt t                                             21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
cacauugccc aagucuccat t                                            21

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actgctgaca aagatggtgt ggccgatgtg tctat                             35

<210> SEQ ID NO 16
```

<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gacaaagaug cuguggccga uaagcuuauc ggccacagca ucuuugucuu uu         52

<210> SEQ ID NO 17
<211> LENGTH: 459
<212> TYPE: DNA
<213> ORGANISM: Homo sapiens

<400> SEQUENCE: 17
gcgacgaagg ccgtgtgcgt gctgaagggc gacggcccag tgcagggcat catcaatttc    60
gagcagaagg aaagtaatgg accagtgaag gtgtggggaa gcattaaagg actgactgaa   120
ggcctgcatg gattccatgt tcatgagttt ggagataata cagcaggctg taccagtgca   180
ggtcctcact ttaatcctct atccagaaaa cacggtgggc caaggatgaa agagaggcat   240
gttggagact tgggcaatgt gactgctgac aaagatggtg tggccgatgt gtctattgaa   300
gattctgtga tctcactctc aggagaccat tgcatcattg ccgcacact ggtggtccat    360 gaaaaagcag atgacttggg caaggtgga atgaagaaa gtacaaagac aggaaacgct    420
ggaagtcgtt tggcttgtgg tgtaattggg atcgcccaa                         459

<210> SEQ ID NO 18
<211> LENGTH: 153
<212> TYPE: PRT
<213> ORGANISM: Homo sapiens

<400> SEQUENCE: 18

Ala Thr Lys Ala Val Cys Val Leu Lys Gly Asp Gly Pro Val Gln Gly
 1               5                  10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 19
<211> LENGTH: 2288
<212> TYPE: DNA
<213> ORGANISM: Homo sapiens

<400> SEQUENCE: 19

```
gtaccctgtt tacatcattt tgccattttc gcgtactgca accggcgggc cacgccgtga      60
aaagaaggtt gttttctcca cagtttcggg gttctggacg tttcccggct gcggggcggg     120
gggagtctcc ggcgcacgcg gccccttggc ccgccccagt cattcccggc cactcgcgac     180
ccgaggctgc cgcaggggc gggctgagcg cgtgcgaggc cattggtttg gggccagagt     240
gggcgaggcg cggaggtctg gcctataaag tagtcgcgga gacggggtgc tggtttgcgt     300
cgtagtctcc tgcaggtctg gggtttccgt tgcagtcctc ggaaccagga cctcggcgtg     360
gcctagcgag ttatggcgac gaaggccgtg tgcgtgctga agggcgacgg cccagtgcag     420
ggcatcatca atttcgagca gaaggcaagg gctgggaccg ggaggcttgt gttgcgaggc     480
cgctcccgac ccgctcgtcc ccccgcgacc ctttgcatgg acgggtcgcc cgccagggct     540
agagcagtta agcagcttgc tggaggttca ctggctagaa agtggtcagc ctgggattgc     600
atggacggat ttttccactc ccaagtctgg ctgcttttta cttcactgtg agggggtaaag    660
gtaaatcagc tgttttcttt gttcagaaac tctctccaac tttgcacttt tcttaaagga     720
aagtaatgga ccagtgaagg tgtggggaag cattaaagga ctgactgaag gcctgcatgg     780
attccatgtt catgagtttg gagataatac agcaggtggg tcataattta gcttttttt      840
cttcttctta taaataggct gtaccagtgc aggtcctcac tttaatcctc tatccagaaa     900
acacggtggg ccaaggatg aagagaggta acaagatgct taactcttgt aatcaatggc      960
gatacgtttc tggagttcat atggtatact acttgtaaat atgtgcctaa gataattccg    1020
tgtttccccc acctttgctt tgaacttgc tgactcatgt gaaaccctgc tcccaaatgc     1080
tggaatgctt ttacttcctg ggcttaaagg aattgacaaa tgggcactta aaacgatttg    1140
gttttgtagc atttgattga atatagaact aatacaagtg ccaaggggga actaatacag    1200
gaaatgttca tgaacagtac tgtcaaccac tagcaaaatc aatcatcatt tgatgctttt    1260
catataggca tgttggagac ttgggcaatg tgactgctga caaagatggt gtggccgatg    1320
tgtctattga agattctgtg atctcactct caggagacca ttgcatcatt ggccgcacac    1380
tggtggtaag ttttcataaa ggatatgcat aaaacttctt ctaacagtac agtcatgtat    1440
ctttcacttt gattgttagt cgcgaattct aagatccaga taaactgtgt ttctgctttt    1500
aaactactaa atattagtat atctctctac taggattaat gttattttc taatattatg    1560
aggttcttaa acatcttttg ggtattgttg ggaggaggta gtgattactt gacagcccaa    1620
agttatcttc ttaaaatttt ttacaggtcc atgaaaaagc agatgacttg ggcaaaggtg    1680
gaaatgaaga agtacaaag acaggaaacg ctggaagtcg tttggcttgt ggtgtaattg     1740
ggatcgccca ataaacattc ccttggatgt agtctgaggc cccttaactc atctgttatc    1800
ctgctagctg tagaaatgta tcctgataaa cattaaacac tgtaatctta aaagtgtaat    1860
tgtgtgactt tttcagagtt gctttaaagt acctgtagtg agaaactgat ttatgatcac    1920
ttggaagatt tgtatagttt tataaaactc agttaaaatg tctgtttcaa tgacctgtat    1980
tttgccagac ttaaatcaca gatgggtatt aaacttgtca gaatttcttt gtcattcaag    2040
cctgtgaata aaaaccctgt atggcactta ttatgaggct attaaaagaa tccaaattca    2100
aactaaatta gctctgatac ttatttatat aaacagcttc agtggaacag atttagtaat    2160
actaacagtg atagcatttt attttgaaag tgttttgaga ccatcaaaat gcatacttta    2220
aaacagcagg tcttttagct aaaactaaca caactctgct tagacaaata ggctgtcctt    2280
tgaagctt                                                             2288
```

<210> SEQ ID NO 20
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 20
cauguuggag acuugggcaa ugugacugcu ca                                32

<210> SEQ ID NO 21
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 21
ugagcaguca cauugcccaa gucuccaaca ug                                32

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic oligonucleotide

<400> SEQUENCE: 22
gagacuuggg caaugugact t                                            21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic oligonucleotide

<400> SEQUENCE: 23
gucacauugc ccaagucuct t                                            21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic oligonucleotide

<400> SEQUENCE: 24
gagacuuggg caaugugact t                                            21

<210> SEQ ID NO 25
<211> LENGTH: 21
<212> TYPE: DNA

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
gucacauugc ccaagucuat t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
uagacuuggg caaugugact t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
gucacauugc ccaagucuct t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
uagacuuggg caaugugact t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 29
gucacauugc ccaagucuat t                                              21

<210> SEQ ID NO 30
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 30
gagacuuggg caaugugaat t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31
gucacauugc ccaagucuct t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
gagacuuggg caaugugact t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
uucacauugc ccaagucuct t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 34
gagacuuggg caaugugaat t                                              21

<210> SEQ ID NO 35
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
uucacauugc ccaagucuct t                                             21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: inosine

<400> SEQUENCE: 36
nagacuuggg caaugugact t                                             21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
gucacauugc ccaagucuct t                                             21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 38
gagacuuggg caaugugact t                                             21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)
<223> OTHER INFORMATION: inosine

<400> SEQUENCE: 39
nucacauugc ccaagucuct t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: inosine

<400> SEQUENCE: 40
nagacuuggg caaugugact t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: inosine

<400> SEQUENCE: 41
nucacauugc ccaagucuct t                                              21

<210> SEQ ID NO 42
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gagucuaggc cauugagacu ucaagagagu cucaauggcc uagacucuu                49

<210> SEQ ID NO 43
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gagacuuggg caaugugacu ucaagagagu cacauugccc aagucuauu                49

<210> SEQ ID NO 44
<211> LENGTH: 49
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 44
gagacuuggg caaugugacu ucaagagagu cacauugccc aagucacuu         49

<210> SEQ ID NO 45
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gagacuuggg caaugugacu ucaagagagu cacauugccc aaguaucuu         49

<210> SEQ ID NO 46
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gagacuuggg caaugugacu ucaagagagu cacauugccc aagacucuu         49

<210> SEQ ID NO 47
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gagacuuggg caaugugacu ucaagagagu cacauugccc aagucucuu         49

<210> SEQ ID NO 48
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gagacuuggg caaugugaau ucaagagagu cacauugccc aagucucuu         49

<210> SEQ ID NO 49
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gagacuuggg caaugugucu ucaagagagu cacauugccc aagucucuu         49

<210> SEQ ID NO 50
<211> LENGTH: 49
<212> TYPE: RNA
<213> ORGANISM: Artificial Sequence
<220> FEATURE:
<223> OTHER INFORMATION: Description of Artificial Sequence: Synthetic
```

```
oligonucleotide

<400> SEQUENCE: 50
gagacuuggg caauguaacu ucaagagagu cacauugccc aagucucuu          49

<210> SEQ ID NO 51
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gagacuuggg caaugagacu ucaagagagu cacauugccc aagucucuu          49

<210> SEQ ID NO 52
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gagucuaggc cauugagacu guucaagaga cagucucaau ggccuagacu cuu     53

<210> SEQ ID NO 53
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gagacuuggg caaugugacu guucaagaga cagucacauu gcccaagucu auu     53

<210> SEQ ID NO 54
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gagacuuggg caaugugacu guucaagaga cagucacauu gcccaaguca cuu     53

<210> SEQ ID NO 55
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gagacuuggg caaugugacu guucaagaga cagucacauu gcccaaguau cuu     53

<210> SEQ ID NO 56
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 56
gagacuuggg caaugugacu guucaagaga cagucacauu gcccaagacu cuu          53

<210> SEQ ID NO 57
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gagacuuggg caaugugacu guucaagaga cagucacauu gcccaagucu cuu          53

<210> SEQ ID NO 58
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gagacuuggg caaugugacu auucaagaga cagucacauu gcccaagucu cuu          53

<210> SEQ ID NO 59
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
gagacuuggg caaugugaca guucaagaga cagucacauu gcccaagucu cuu          53

<210> SEQ ID NO 60
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gagacuuggg caaugugaau guucaagaga cagucacauu gcccaagucu cuu          53

<210> SEQ ID NO 61
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gagacuuggg caaugugucu guucaagaga cagucacauu gcccaagucu cuu          53

<210> SEQ ID NO 62
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 62
gagacuuggg caaugugacu guucaagaga cagucacauu gcccaagucu cuu      53

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gagacuuggg caaugugacu g                                         21

<210> SEQ ID NO 64
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cagucacauu gcccaagucu cuu                                       23

<210> SEQ ID NO 65
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65 gagacuugggg caaugugacu guucaagaga cagucacauu gcccaaguca cuu     53

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66 gagacuugggg caaugugacu g                                        21

<210> SEQ ID NO 67
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
cagucacauu gcccaagucu cuu                                       23

<210> SEQ ID NO 68
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
```
gagacuuggg caaugugaauu guucaagaga cagucacauu gcccaagucu cuu            53

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gagacuuggg caaugugacu g                                                21

<210> SEQ ID NO 70
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cagucacauu gcccaagucu cuu                                              23

<210> SEQ ID NO 71
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gaggcauguu ggagacuugg guucaagaga cccaagucuc caacaugccu cuu             53

<210> SEQ ID NO 72
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gaggcauguu ggagacuugg guucaagaga cccaagucuc caacaugcca cuu             53

<210> SEQ ID NO 73
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gaggcauguu ggagacuuag guucaagaga cccaagucuc caacaugccu cuu             53

<210> SEQ ID NO 74
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74

-continued guuggagacu ugggcaaugu guucaagaga cacauugccc aagucuccaa cuu         53

<210> SEQ ID NO 75
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
guuggagacu ugggcaaugu guucaagaga cacauugccc aagucuccau cuu         53

<210> SEQ ID NO 76
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
guuggagacu ugggcaauau guucaagaga cacauugccc aagucuccaa cuu         53

<210> SEQ ID NO 77
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
aaugugacug cugacaaaga uuucaagaga aucuuuguca gcagucacau uuu         53

<210> SEQ ID NO 78
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aaugugacug cugacaaaga uuucaagaga aucuuuguca gcagucacaa uuu         53

<210> SEQ ID NO 79
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
aaugugacug cugacaaaua uuucaagaga aucuuuguca gcagucacau uuu         53

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80

```
aggcatgttg gagacttggg caatgtgact gctgacaaa                                 39

<210> SEQ ID NO 81
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tttgtcagca gtcacattgc ccaagtctcc aacatgcct                                 39
```